US012611134B2

(12) United States Patent
Toth et al.

(10) Patent No.: US 12,611,134 B2
(45) Date of Patent: Apr. 28, 2026

(54) DEVICES, SYSTEMS, AND METHODS FOR DIAGNOSIS AND TREATMENT OF OVERACTIVE BLADDER

(71) Applicant: Autonomix Medical, Inc., Ivyland, PA (US)

(72) Inventors: Landy Toth, Doylestown, PA (US); Robert S. Schwartz, Inver Grove Heights, MN (US); David Robins, Congers, NY (US)

(73) Assignee: Autonomix Medical, Inc., Ivyland, PA (US)

( * ) Notice: Subject to any disclaimer, the term of this patent is extended or adjusted under 35 U.S.C. 154(b) by 563 days.

(21) Appl. No.: 18/079,361

(22) Filed: Dec. 12, 2022

(65) Prior Publication Data

US 2024/0090820 A1 Mar. 21, 2024

Related U.S. Application Data

(63) Continuation of application No. 16/229,004, filed on Dec. 21, 2018, now Pat. No. 11,564,616, which is a (Continued)

(51) Int. Cl.
*A61B 5/391* (2021.01)
*A61B 5/00* (2006.01)
(Continued)

(52) U.S. Cl.
CPC ............ *A61B 5/391* (2021.01); *A61B 5/0036* (2018.08); *A61B 5/0538* (2013.01); *A61B 5/11* (2013.01);
(Continued)

(58) Field of Classification Search
CPC ..... A61B 5/391; A61B 5/0036; A61B 5/0538; A61B 5/11; A61B 5/1459; A61B 5/202;
(Continued)

(56) References Cited

U.S. PATENT DOCUMENTS

| 5,957,920 A | 9/1999 | Baker |
| 6,053,913 A | 4/2000 | Tu et al. |

(Continued)

FOREIGN PATENT DOCUMENTS

| AU | 2010207062 B2 | 5/2015 |
| AU | 2014233285 A1 | 9/2015 |

(Continued)

OTHER PUBLICATIONS

Canadian Patent Application No. 3,184,524, Office Action, May 30, 2024, 5 pages.

(Continued)

*Primary Examiner* — Mark W. Bockelman
(74) *Attorney, Agent, or Firm* — Ryan, Mason & Lewis, LLP

(57) ABSTRACT

A system for modulating bladder function is disclosed. A system for evaluating the electrophysiological function of a bladder is disclosed. Methods for performing a controlled surgical procedure on a bladder are disclosed. A system for performing controlled surgical procedures in a minimally invasive manner is disclosed. An implantable device for monitoring and/or performing a neuromodulation procedure on a bladder is disclosed.

20 Claims, 16 Drawing Sheets

Related U.S. Application Data continuation of application No. 14/407,416, filed as application No. PCT/US2013/045605 on Jun. 13, 2013, now Pat. No. 10,206,616.

(60) Provisional application No. 61/659,463, filed on Jun. 14, 2012.

(51) Int. Cl.

| | |
|---|---|
| A61B 5/0538 | (2021.01) |
| A61B 5/11 | (2006.01) |
| A61B 5/1459 | (2006.01) |
| A61B 5/20 | (2006.01) |
| A61B 5/388 | (2021.01) |
| A61B 5/395 | (2021.01) |
| A61B 17/00 | (2006.01) |
| A61B 18/00 | (2006.01) |
| A61B 18/14 | (2006.01) |
| A61B 90/00 | (2016.01) |
| A61N 1/36 | (2006.01) |
| A61N 7/00 | (2006.01) |

(52) U.S. Cl.
CPC ............ *A61B 5/1459* (2013.01); *A61B 5/202* (2013.01); *A61B 5/205* (2013.01); *A61B 5/388* (2021.01); *A61B 5/395* (2021.01); *A61B 5/4875* (2013.01); *A61B 5/6848* (2013.01); *A61B 18/1485* (2013.01); *A61N 1/36007* (2013.01); *A61N 7/00* (2013.01); *A61B 2017/00057* (2013.01); *A61B 2018/0016* (2013.01); *A61B 2018/0022* (2013.01); *A61B 2018/00226* (2013.01); *A61B 2018/00267* (2013.01); *A61B 2018/00517* (2013.01); *A61B 2018/00791* (2013.01); *A61B 2018/00839* (2013.01); *A61B 2018/1465* (2013.01); *A61B 2018/1475* (2013.01); *A61B 2090/065* (2016.02)

(58) Field of Classification Search
CPC ........... A61B 5/205; A61B 5/24; A61B 5/389; A61B 5/4875; A61B 5/6848; A61B 18/1485; A61B 2017/00057; A61B 2018/00166; A61B 2018/0022; A61B 2018/00226; A61B 2018/00267; A61B 2018/00517; A61B 2018/00791; A61B 2018/00839; A61B 2018/1465; A61B 2018/1475; A61B 2090/065; A61B 5/4836; A61N 1/36007; A61N 7/00
See application file for complete search history.

(56) References Cited

U.S. PATENT DOCUMENTS

| | | |
|---|---|---|
| 6,319,208 B1 | 11/2001 | Abita et al. |
| 6,466,817 B1 | 10/2002 | Kaula et al. |
| 7,054,689 B1 | 5/2006 | Whitehurst et al. |
| 7,177,677 B2 | 2/2007 | Kaula et al. |
| 7,430,450 B2 | 9/2008 | Imran |
| 7,865,236 B2 | 1/2011 | Cory et al. |
| 7,885,700 B2 | 2/2011 | Clark et al. |
| 8,097,926 B2 | 1/2012 | De Graff et al. |
| 8,320,990 B2 | 11/2012 | Vij |
| 8,536,667 B2 | 9/2013 | De Graff et al. |
| 8,702,857 B2 | 4/2014 | Venema et al. |
| 8,706,219 B2 | 4/2014 | Feldman et al. |
| 8,712,549 B2 | 4/2014 | Zdeblick et al. |
| 9,186,060 B2 | 11/2015 | De Graff et al. |
| 9,295,842 B2 | 3/2016 | Ghaffari et al. |
| 9,326,816 B2 | 5/2016 | Srivastava |
| 9,339,332 B2 | 5/2016 | Srivastava |
| 9,629,586 B2 | 4/2017 | Ghaffari et al. |
| 9,662,069 B2 | 5/2017 | De Graff et al. |
| 9,750,421 B2 | 9/2017 | Ghaffari et al. |
| 9,801,557 B2 | 10/2017 | Ghaffari et al. |
| 9,820,673 B2 | 11/2017 | Feldman et al. |
| 9,931,047 B2 | 4/2018 | Srivastava |
| 10,186,546 B2 | 1/2019 | De Graff et al. |
| 10,271,898 B2 | 4/2019 | Cao et al. |
| 10,292,610 B2 | 5/2019 | Srivastava |
| 10,426,545 B2 | 10/2019 | Asirvatham et al. |
| 10,737,123 B2 | 8/2020 | Sullivan et al. |
| 10,918,298 B2 | 2/2021 | Rogers et al. |
| 11,058,484 B2 | 7/2021 | Asirvatham et al. |
| 11,515,029 B2 | 11/2022 | Sullivan et al. |
| 11,540,775 B2 | 1/2023 | Shachar et al. |
| 2001/0020162 A1 | 9/2001 | Mosel et al. |
| 2002/0138075 A1 | 9/2002 | Edwards et al. |
| 2002/0161422 A1 | 10/2002 | Swanson et al. |
| 2004/0044277 A1 | 3/2004 | Fuimaono et al. |
| 2004/0186468 A1* | 9/2004 | Edwards ............ A61B 18/1492<br>606/41 |
| 2005/0203604 A1 | 9/2005 | Brabec et al. |
| 2005/0245840 A1 | 11/2005 | Christopherson et al. |
| 2005/0288730 A1 | 12/2005 | Deem et al. |
| 2006/0129125 A1* | 6/2006 | Copa .................. A61M 5/3007<br>604/509 |
| 2006/0190047 A1 | 8/2006 | Gerber et al. |
| 2006/0206189 A1 | 9/2006 | Furst et al. |
| 2007/0135875 A1 | 6/2007 | Demarais et al. |
| 2009/0137952 A1 | 5/2009 | Ramamurthy et al. |
| 2009/0192571 A1 | 7/2009 | Stett et al. |
| 2010/0215834 A1 | 8/2010 | Nesbitt |
| 2010/0298895 A1 | 11/2010 | Ghaffari et al. |
| 2011/0301662 A1 | 12/2011 | Bar-Yoseph et al. |
| 2012/0017804 A1 | 1/2012 | Venema et al. |
| 2012/0157804 A1 | 6/2012 | Rogers et al. |
| 2012/0191079 A1 | 7/2012 | Moll et al. |
| 2013/0172717 A1 | 7/2013 | Halpern et al. |
| 2014/0088612 A1* | 3/2014 | Bartol .................. A61B 5/6852<br>606/130 |
| 2014/0275993 A1 | 9/2014 | Ballakur |
| 2015/0190194 A1 | 7/2015 | Weber et al. |
| 2017/0188942 A1 | 7/2017 | Ghaffari et al. |
| 2018/0078169 A1 | 3/2018 | Feldman et al. |
| 2019/0069949 A1 | 3/2019 | Vrba et al. |
| 2020/0337765 A1 | 10/2020 | Smith |
| 2020/0375541 A1 | 12/2020 | Shachar et al. |
| 2021/0307824 A1 | 10/2021 | Asirvatham et al. |
| 2022/0047202 A1 | 2/2022 | Shachar et al. |
| 2023/0057437 A1 | 2/2023 | Sullivan et al. |

FOREIGN PATENT DOCUMENTS

| | | |
|---|---|---|
| AU | 2013230893 B2 | 12/2015 |
| AU | 2013305279 B2 | 7/2017 |
| AU | 2015358385 B2 | 9/2020 |
| CA | 2934245 A1 | 7/2015 |
| CA | 2969129 A1 | 6/2016 |
| CA | 2749024 C | 10/2016 |
| CN | 203138452 U | 8/2013 |
| CN | 102292395 B | 7/2014 |
| CN | 103284693 B | 12/2014 |
| CN | 103271766 B | 8/2015 |
| CN | 105328709 A | 8/2016 |
| CN | 106068105 A | 11/2016 |
| CN | 105120785 B | 11/2017 |
| CN | 107802341 B | 7/2020 |
| CN | 105658163 B | 8/2020 |
| CN | 111700677 A | 9/2020 |
| DK | 2389415 T3 | 11/2014 |
| EP | 1187653 A2 | 3/2002 |
| EP | 1187653 B1 | 3/2002 |
| EP | 1451595 B1 | 7/2009 |
| EP | 2389415 B1 | 8/2014 |
| EP | 2513953 B1 | 10/2017 |
| EP | 3038555 B1 | 7/2018 |
| EP | 2986243 B1 | 6/2020 |
| EP | 3226795 B1 | 8/2020 |
| EP | 2887900 B1 | 12/2020 |

(56)    References Cited

FOREIGN PATENT DOCUMENTS

| EP | 2967713 | B1 | 12/2020 |
|----|---------|----|---------|
| EP | 3799815 | A1 | 4/2021 |
| EP | 3038556 | B1 | 5/2021 |
| EP | 3884897 | A1 | 9/2021 |
| EP | 4144294 | A1 | 3/2023 |
| ES | 2329773 | T3 | 12/2009 |
| ES | 2523498 | T3 | 11/2014 |
| JP | 2000325328 | A | 11/2000 |
| JP | 2002017743 | A | 1/2002 |
| JP | 2002113036 | A | 4/2002 |
| JP | 2002517300 | A | 6/2002 |
| JP | 2002-369810 | | 12/2002 |
| JP | 2002369810 | A | 12/2002 |
| JP | 2003510126 | A | 3/2003 |
| JP | 2004507290 | A | 3/2004 |
| JP | 2006505322 | A | 2/2006 |
| JP | 2006509547 | A | 3/2006 |
| JP | 20070521914 | A | 8/2007 |
| JP | 2008-537535 | | 9/2008 |
| JP | 2008537535 | A | 9/2008 |
| JP | 2011513038 | A | 4/2011 |
| JP | 2011152449 | A | 8/2011 |
| JP | 5405706 | B2 | 2/2014 |
| JP | 5681117 | B2 | 3/2015 |
| JP | 5694947 | B2 | 4/2015 |
| JP | 2016534842 | A | 11/2016 |
| JP | 2017502752 | A | 1/2017 |
| JP | 6109863 | B2 | 4/2017 |
| JP | 2017148514 | A | 8/2017 |
| JP | 6204616 | B2 | 9/2017 |
| JP | 2017536187 | A | 12/2017 |
| JP | 6574134 | B2 | 9/2019 |
| KR | 101590005 | B1 | 1/2016 |
| KR | 20160106582 | A | 9/2016 |
| KR | 101743628 | B1 | 6/2017 |
| NL | 2002442 | C2 | 7/2010 |
| WO | 00062696 | A1 | 10/2000 |
| WO | 2001022897 | A1 | 4/2001 |
| WO | 2001093759 | A1 | 12/2001 |
| WO | 0074763 | A2 | 3/2002 |
| WO | 2003048789 | A2 | 6/2003 |
| WO | 2004052182 | A2 | 6/2004 |
| WO | 2006044868 | A1 | 4/2006 |
| WO | 20090114689 | A1 | 9/2009 |
| WO | 2010030373 | A2 | 3/2010 |
| WO | 2010067360 | A2 | 6/2010 |
| WO | 2010082993 | A2 | 7/2010 |
| WO | 2010085140 | A1 | 7/2010 |
| WO | 2011059331 | A2 | 5/2011 |
| WO | 2011084450 | A1 | 7/2011 |
| WO | 2011093991 | A1 | 8/2011 |
| WO | 2013134479 | A1 | 9/2013 |
| WO | PCT/US2013/045605 | A1 | 11/2013 |
| WO | 2014029355 | A1 | 2/2014 |
| WO | 2014172398 | A1 | 10/2014 |
| WO | 2015031643 | A1 | 3/2015 |
| WO | 2015031648 | A1 | 3/2015 |
| WO | 2015061457 | A1 | 4/2015 |
| WO | 2015102951 | A2 | 7/2015 |
| WO | 2015103541 | A1 | 7/2015 |
| WO | 2016090175 | A1 | 6/2016 |
| WO | 2020242753 | A1 | 12/2020 |
| WO | 2023038682 | A1 | 3/2023 |
| WO | 2023038748 | A1 | 3/2023 |

OTHER PUBLICATIONS

Canadian Patent Application No. 2,876,080, Office Action, May 22, 2020, 5 pages.
Canadian Patent Application No. 2,876,080, Office Action, Aug. 19, 2021, 4 pages.
Canadian Patent Application No. 2,876,080, Office Action, Feb. 13, 2019, 3 pages.
Australian Patent Application No. 2013274158, Office Action, Oct. 15, 2017, 4 pages.
Australian Patent Application No. 2013274158, Office Action, May 3, 2017, 4 pages.
European Patent Application No. 13804 720.4-1115, Office Action, Jul. 11, 2018, 8 pages.
Indian Patent Application No. 194/CHENP/2015, Office Action, Oct. 14, 2020, 8 pages.
Indian Patent Application No. 194/CHENP/2015, Office Action, Feb. 13, 2024, 2 pages.
Indian Patent Application No. 194/CHENP/2015, Office Action, Mar. 14, 2024, 2 pages.
Japanese Patent Application No. 2015-517417, Office Action, Apr. 4, 2017, 5 pages.
Japanese Patent Application No. 2015-517417, Office Action, Mar. 30, 2017, 5 pages.
Japanese Patent Application No. 2018-087942, Office Action, Dec. 24, 2019, 2 pages.
Singapore Written Opinion No. 11201408219T, Jun. 21, 2017, 6 pages.
Singapore Written Opinion No. 11201408219T, Sep. 16, 2016, 6 pages.
Singapore Written Opinion No. 11201408219T, Mar. 3, 2016, 7 pages.

* cited by examiner

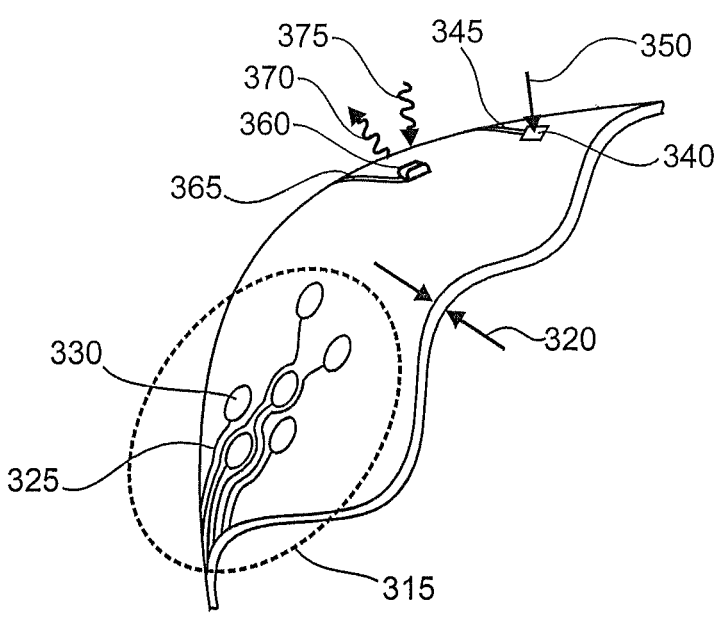
*Fig 3*
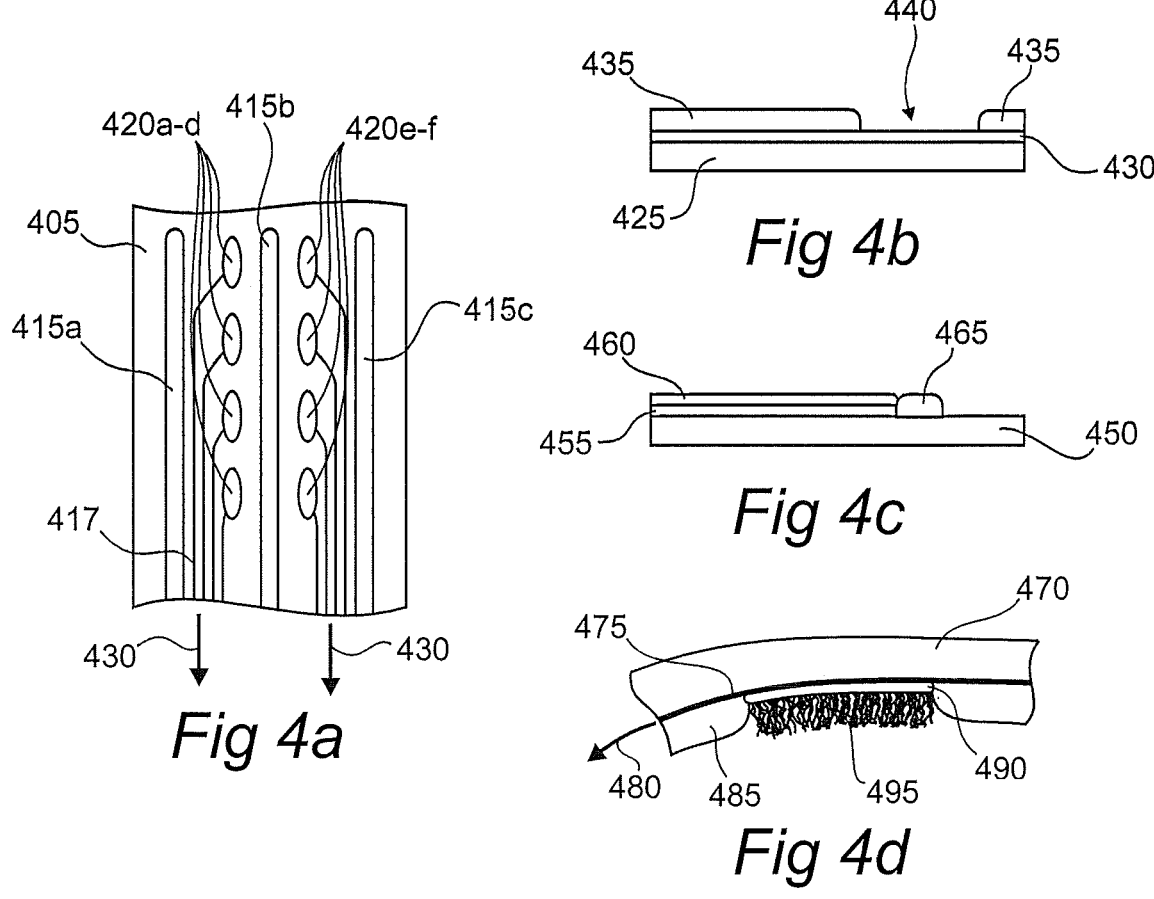
*Fig 4a*
*Fig 4b*
*Fig 4c*
*Fig 4d*

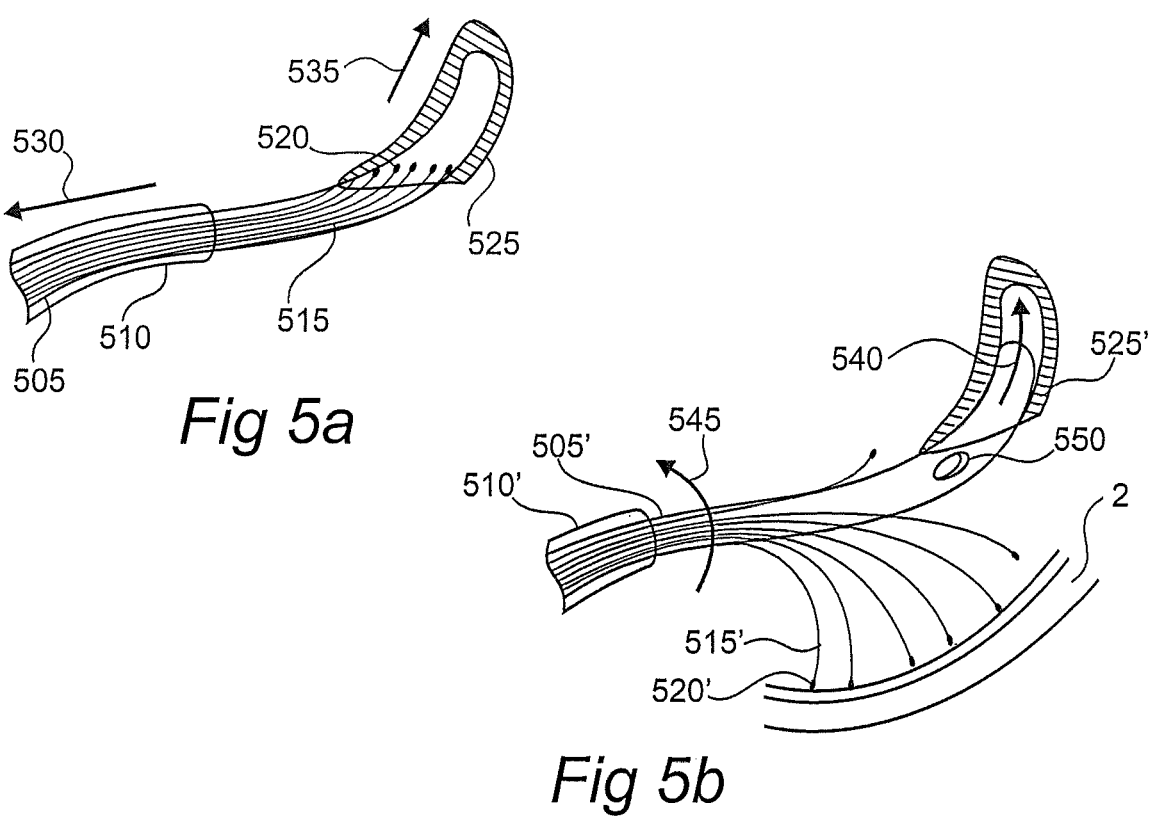
*Fig 5a*
*Fig 5b*
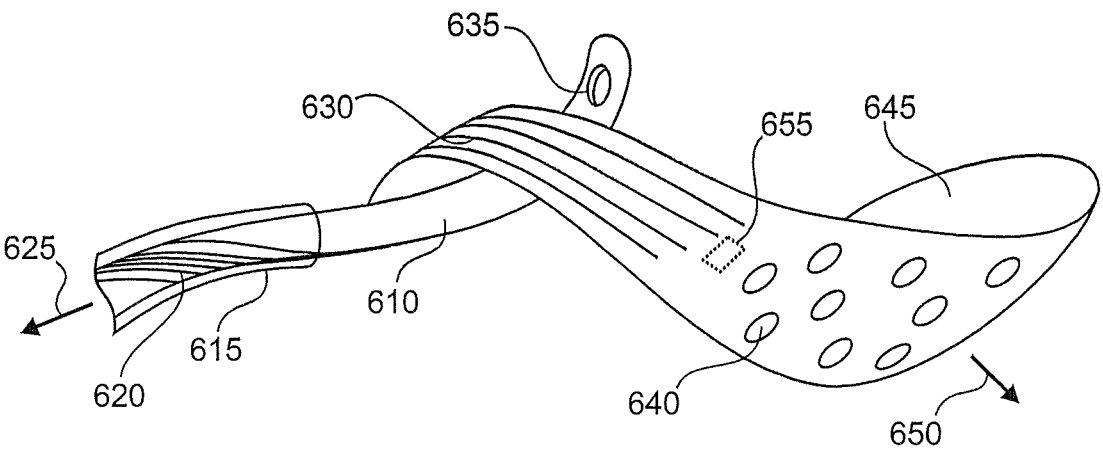
*Fig 6*

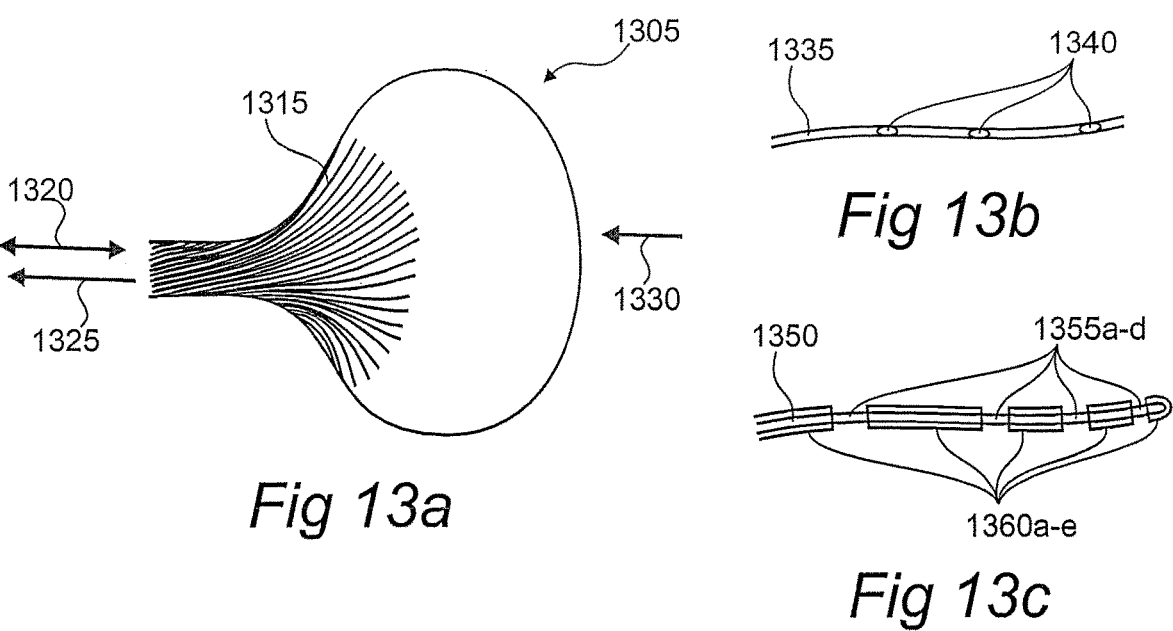
*Fig 13a*
*Fig 13b*
*Fig 13c*
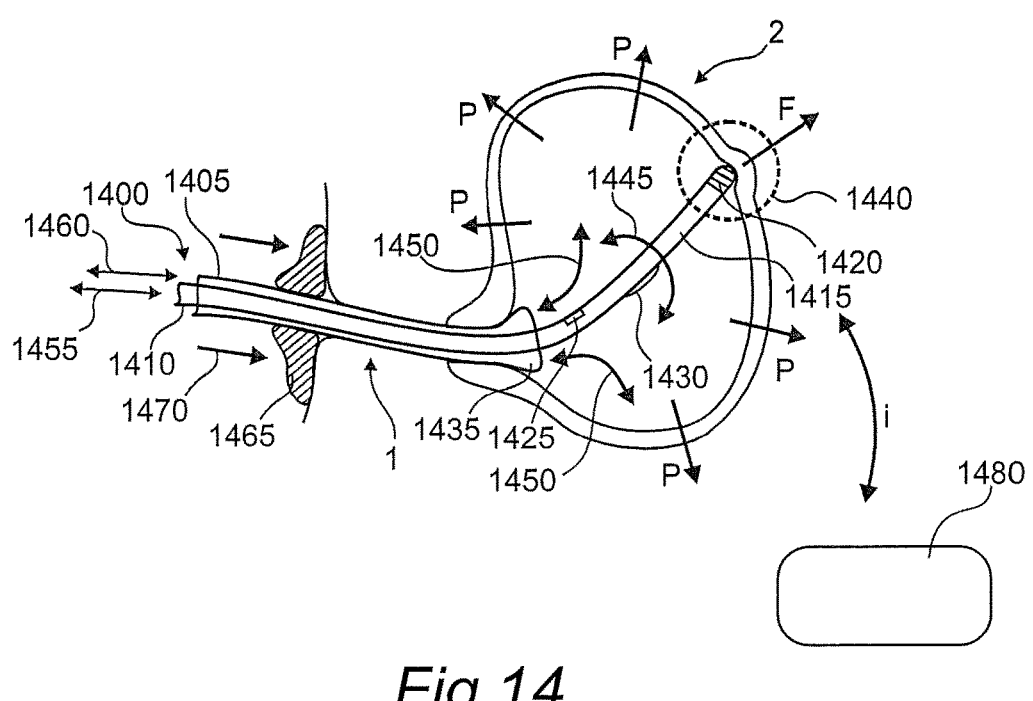
*Fig 14*

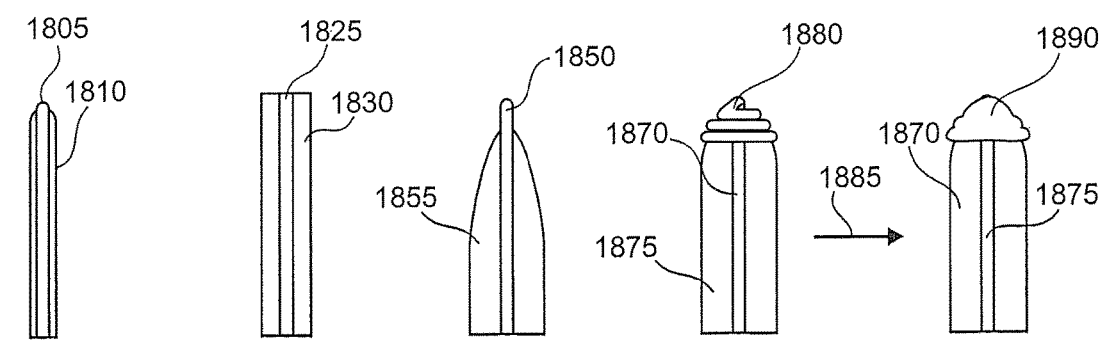
*Fig 18a*     *Fig 18b*     *Fig 18c*     *Fig 18d*     *Fig 18e*
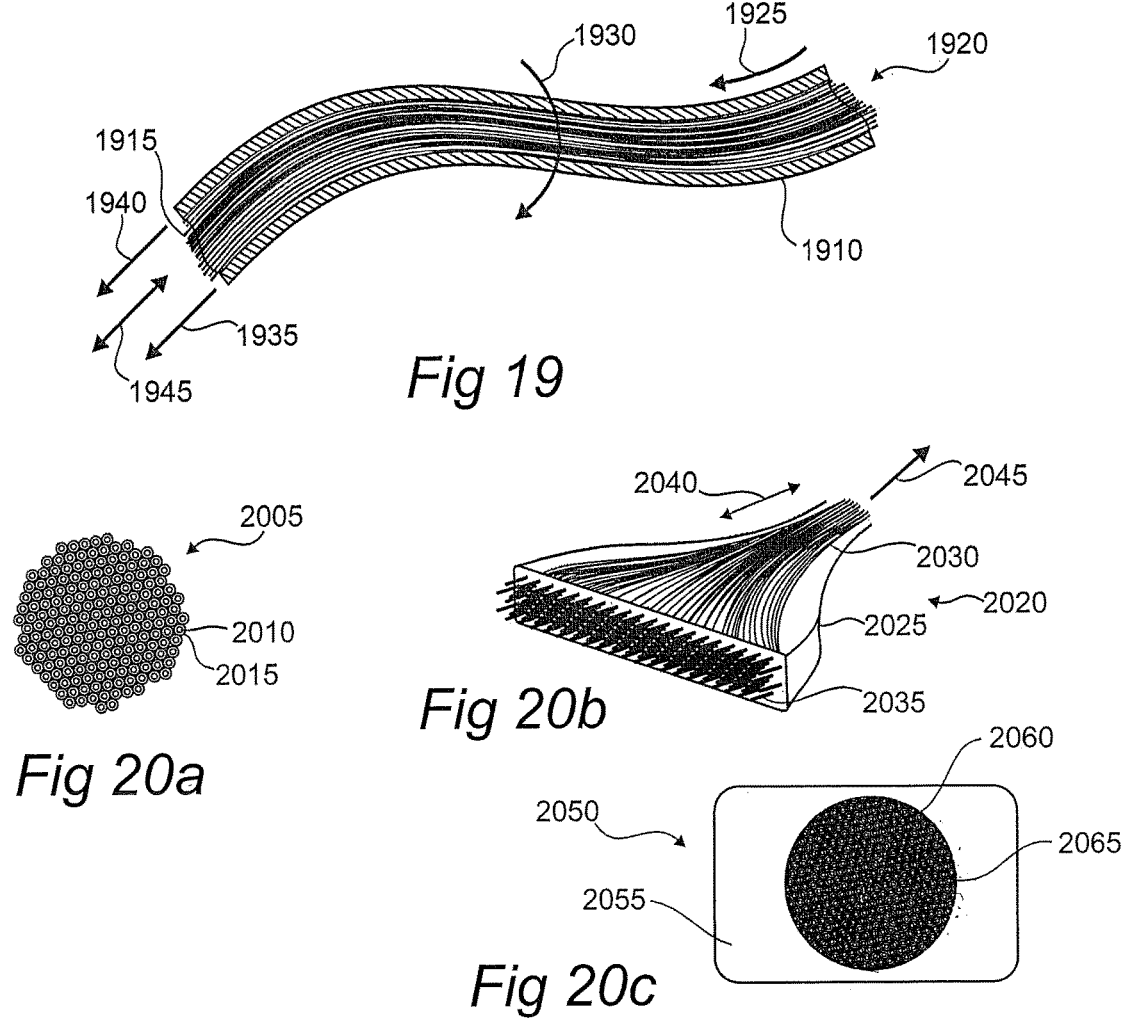
*Fig 19*
*Fig 20a*
*Fig 20b*
*Fig 20c*

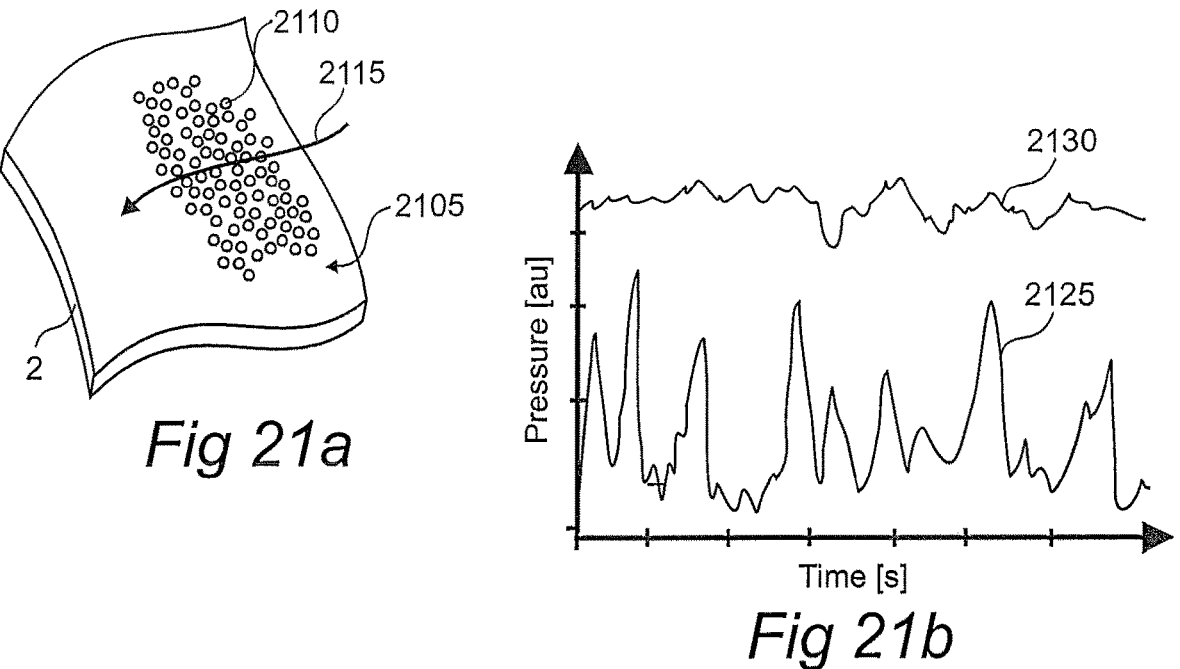
*Fig 21a*
*Fig 21b*
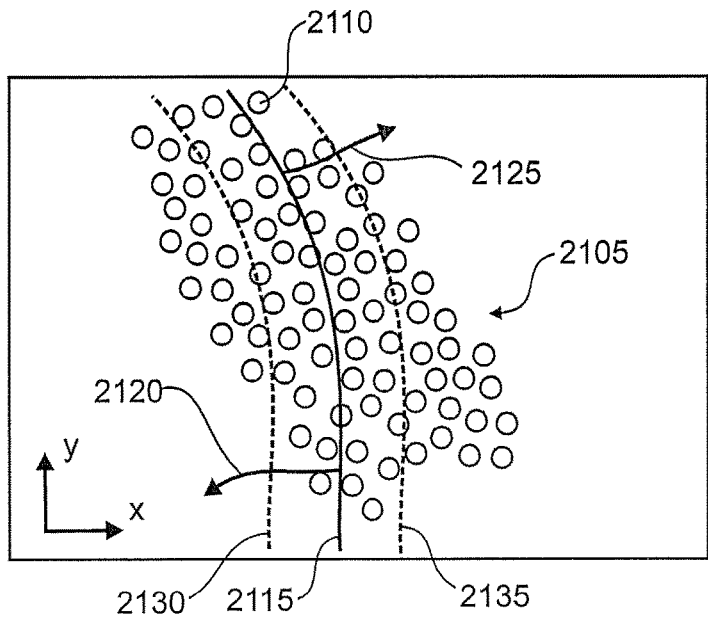
*Fig 21c*

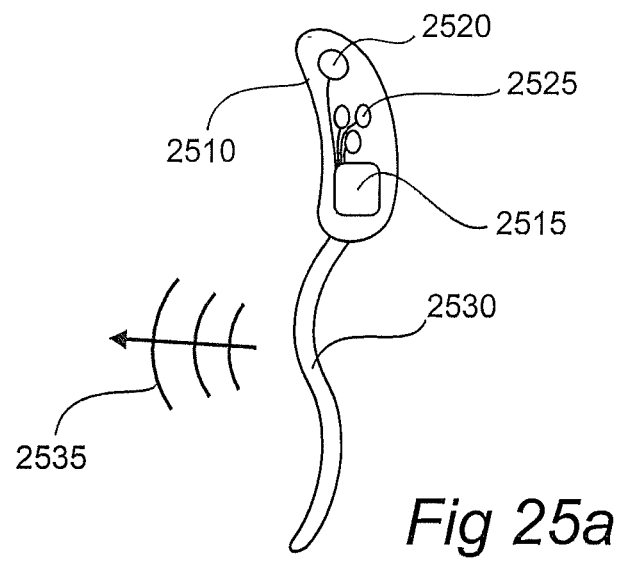
*Fig 25a*
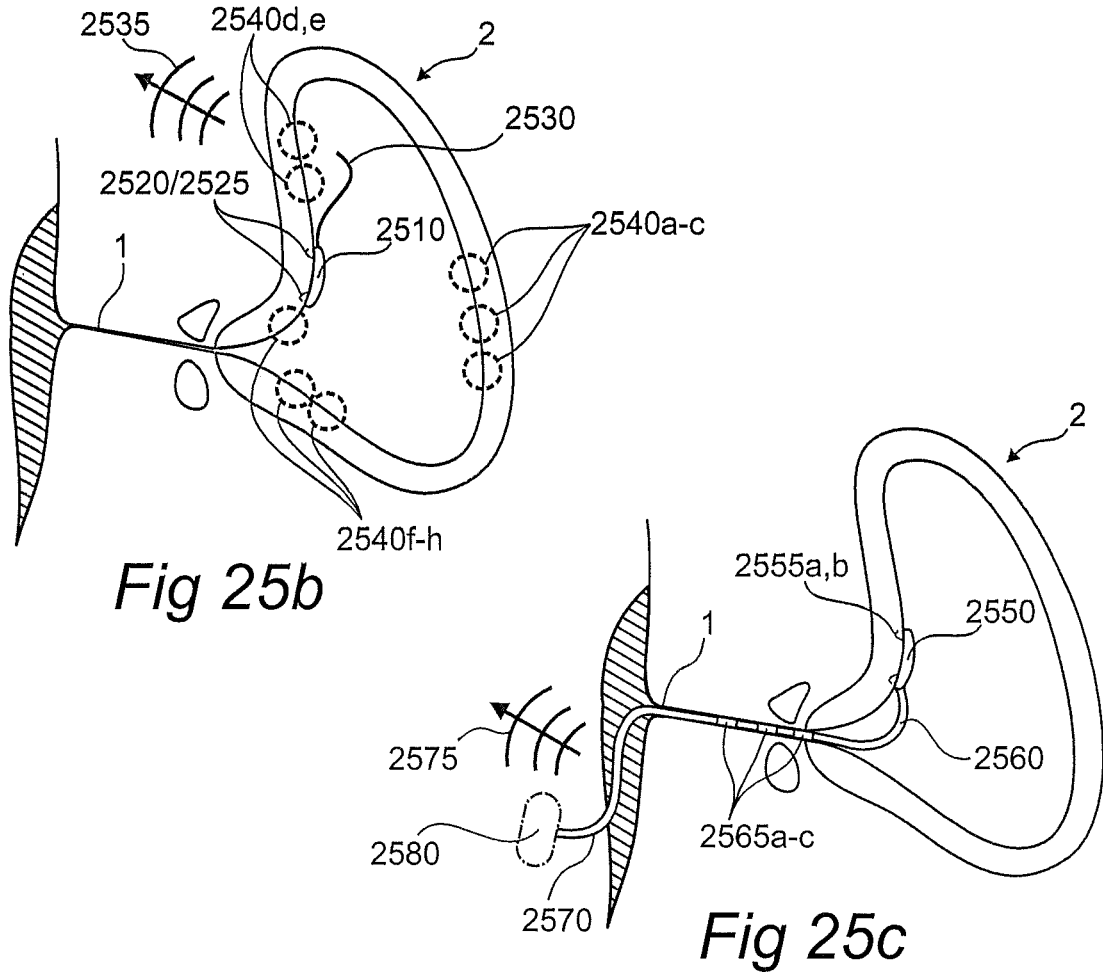
*Fig 25b*
*Fig 25c*

DEVICES, SYSTEMS, AND METHODS FOR DIAGNOSIS AND TREATMENT OF OVERACTIVE BLADDER

CROSS-REFERENCE TO RELATED APPLICATION

The present application is a continuation of U.S. patent application Ser. No. 16/229,004, filed Dec. 21, 2018, which is a continuation of U.S. patent application Ser. No. 14/407, 416, filed Dec. 11, 2014, which is a national stage application of International Application No. PCT/2013/045605, filed Jun. 13, 2013, which claims the benefit of and priority to U.S. Provisional Patent Application Ser. No. 61/659,463, filed Jun. 14, 2012, the entire contents of which are incorporated by reference herein for all purposes.

BACKGROUND

Technical Field

The present disclosure is directed to systems, devices, and methods for assessing, treating, and monitoring an internal surface of a body (e.g., an organ wall, a tissue site, etc.). The present disclosure is further directed to systems, devices, and methods for diagnosing and treating neurological diseases of the bladder.

Background

Urine storage symptoms (e.g., urgency, frequency, and nocturia), with or without associated urge incontinence are characterized as overactive bladder (OAB). In subjects with OAB, smooth muscle in the unstable bladders often shows enhanced spontaneous contractile activity. In addition, altered responses to electrical stimulation and/or agonists are seen from the unstable detrusor. The bladder smooth muscle from patients suffering from unstable bladder demonstrates increased myogenic activity along with fused tetanic contractions and changes in morphological structure (increased connective tissue between muscle fascicles often associated with local trauma). Sensitization of bladder afferents may lead to enhanced signal transmission along associated neurons. Furthermore, in genomically predisposed patients (e.g., patients with familial urge incontinence or chronic pain syndromes), or patients with long-term environmental changes (e.g., following spinal cord injury, obstruction, inflammation, etc.), nerve growth factor (NGF) may alter afferents irreversibly. Such conditions often lead to a long term chronic condition for patients that can be difficult to manage.

The overactive bladder (OAB) and urinary incontinence (UI) marketplace for drug and device based therapies in the United States is an over $12 billion a year industry. Prevalence based modeling analyses have shown the OAB-attributable expenditures in the US to be $65.9B per year. The conditions affect over 16 percent of all Americans (projected prevalence is between 15% and 38%), resulting in approximately 37 million men and women living with the OAB in the US. Due to social stigmas attached to OAB and UI, as well as misunderstanding of the signs and symptoms associated with OAB and UI, only 40 percent of those affected (13.6M) seek treatment. Of those 13.6 million individuals, nearly 30 percent are unsatisfied with their current therapy.

Currently, a range of OAB treatment options are available for patients or currently under development. Such treatments include anticholinergic agents (antimuscarinic agents), $\beta_3$ agonists (sensory inhibition), vanilloid receptor agents (desensitization of C-fiber-afferent neurons), neurokinin-1 receptor antagonists (pathophysiologic sensory signaling interference), phosphodiesterase-5 inhibitors (symptom relief), botulinum toxin (neuromuscular blocking agents), sacral neuromodulation (surgically implanted stimulation devices), and posterior tibial nerve stimulation (externally applied stimulation devices). Treatments to date have been met with limited success and, as mentioned previously, a large subset of the patient population is currently unsatisfied with their current therapy.

SUMMARY

One objective of the present disclosure is to provide systems, devices, and methods to for treatment of a disease state in a body (e.g., to treat overactive bladder). Another objective is to provide a system for performing sympathectomy and/or parasympathectomy on a compliant structure within a body (e.g., a bladder wall, an intestinal wall, etc.). Yet another objective is to provide systems, devices, and methods to map, monitor, and/or study electrophysiology of a structure within a body (e.g., a bladder wall, an intestinal wall, etc.).

Another objective is to provide devices, systems, and methods for monitoring local neurological activity along an organ wall and/or to extract spatially fine electrophysiological characteristics from amongst one or more macroscopic biosignals (e.g., to extract local neurological signals from potentially overwhelming electrocardiographic and/or electromyographic signals), and to predict the spatial origin of neurological signals (e.g., as part of a neuronal locating and/or mapping system, etc.).

Yet another objective is to provide devices, systems, and methods for determining the directivity of local neurological activity, directivity of signal propagation, and/or assessing neurological behavior (e.g., regular behavior versus rogue behavior) along a surface in a body (e.g., along a bladder wall, an intestinal wall, etc.).

Another objective is to provide devices, systems, and methods for determining the location (i.e., along a surface, depth into a surface, etc.) of one or more anatomical features (e.g., sensory receptor, a neuron, a nerve plexus, etc.) along an organ or cavity wall within a body.

Another objective is to provide devices, systems, and methods for ablating local anatomy within a body with physiological feedback before, during, and/or after the procedure to assess the state of completion thereof.

Another objective is to provide devices, systems, and methods for combined urinary bladder urodynamic testing, neurological assessment, treatment, and/or urodynamic follow up. Such systems, devices, and methods may be advantageous for substantially optimally treating diseased tissue states such as those associated with overactive bladder.

The above objectives are wholly or partially met by devices, systems, and methods described herein. In particular, features and aspects of the present disclosure are set forth in the appended claims, following description, and the annexed drawings.

According to a first aspect there is provided, a surgical tool for neuromodulating bladder function, including an elongate delivery member configured and dimensioned to be inserted into a bladder through a urethra, a therapy delivery element coupled with the delivery member, configured to interface with a tissue in a target region of a bladder wall to provide therapy to the target region; and one or more sensing tips electrically and mechanically coupled with the delivery member, configured to interface with one or more tissue surfaces of the bladder wall and/or the urethra, the sensing tips configured to convey one or more electrophysiological signals associated with the tissue surfaces before, during, and/or after the therapy.

In aspects, the electrophysiological signals may be related to one or more of water concentration, tissue tone, evoked potential, remotely stimulated nervous activity, a pressure stimulated nervous response, an electrically stimulated movement, sympathetic nervous activity, an electromyographic signal [EMG], a mechanomyographic signal [MMG], a local field potential, an electroacoustic event, vasodialation, bladder wall stiffness, muscle sympathetic nerve activity [MSNA], central sympathetic drive, nerve traffic, or combinations thereof, or the like.

In aspects, one or more of the sensing tips comprise the therapy delivery element. In aspects, at least one of the tissue surfaces is substantially coincident with the target region.

In aspects, one or more sensing tips may include one or more electrodes in accordance with the present disclosure configured to interface with the associated tissue surface. In aspects, one or more of the electrodes may include embossed, plated, and/or filament loaded structures thereupon configured to protrude into the associated tissue surface when biased there against. In aspects, one or more of the sensing tips may be electrically coupled with a microcircuit in accordance with the present disclosure, the microcircuit configured to condition the signal. In aspects, the microcircuit is embedded into the surgical tool and at least a portion of the electrical coupling is provided via the delivery member. In aspects, one or more sensing tips may include one or more needle electrodes and/or one or more whiskers each of which having a characteristic length and a tip, the needle electrode and/or whiskers arranged so as to extend from the sensing tip into the associated tissue surface.

In aspects, one or more sensing tips may include a mechanomyographic (MMG) sensing element configured to generate a mechanomyographic signal (MMG) from the associated tissue surface, a compliance sensor, configured to generate a tissue tone signal, and/or a microelectrode configured to interface with the associated tissue surface, the microelectrode having an area of less than 5000 $\mu m^2$, less than 1000 $\mu m^2$, less than 250 $\mu m^2$, less than 100 $\mu m^2$, etc.

In aspects, one or more sensing tips and/or the therapy delivery element may be configured to stimulate (e.g., electrically stimulate, mechanically stimulate, rub, vibrate, pinch, pressurize, provide a current to, etc.) and/or ablate (e.g., thermally ablate, apply RF current thereto, cyroablate, ultrasonically ablate, radiosurgically ablate, etc.) the associated tissue surface and/or target region respectively. In aspects, one or more sensing tips may be configured so as to monitor the effect of the stimulation and/or ablation on the tissue surface and/or target region.

In aspects, the therapy delivery element may be configured for delivering a therapeutic substance in accordance with the present disclosure to the target region. In aspects, one or more of the sensing tips may be configured to monitor the effect of the therapeutic substance on the target region.

In aspects, some non-limiting examples of therapeutic substances are a chemical, a drug substance, a neuromodulating substance, a neuroblocking substance, an acid, a base, a denervating agent, or a combination thereof, a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, capsaicin, an anesthetic, lidocaine, tetanus toxin, quaternary ammonium salts, a pachycurare, a leptocurare, acetylcholine, aminosteroids, a combination thereof, or the like.

In aspects, the delivery member may include a lumen for providing fluid communication between the bladder and a fluid source located outside of the bladder. In aspects, a therapeutic fluid (i.e., for performing hyperthermia based chemotherapy, etc.) may be provided via the lumen.

In aspects, the surgical tool may include a balloon mechanically coupled to the delivery member, configured and dimensioned to interface with the bladder wall when filled with a fluid. In aspects, one or more of the sensing tips and/or the therapy delivery element may be attached to the balloon and arranged so as to interface with the associated tissue surface and/or target region upon filling of the balloon. In aspects, the delivery member comprising a lumen, arranged so as to provide fluid communication between the balloon and a fluid source positioned outside of the bladder. In aspects, the lumen may be coupled in fluid communication with the balloon, the tool may include a pressure sensor in fluid communication with the balloon, configured to measure the balloon fill pressure during a procedure, and/or one or more sensing tips may be configured to measure an interfacial pressure between the balloon and the associated tissue surface.

In aspects, the therapy delivery element may be configured to deliver thermal energy, radio frequency energy, etc. to the target region.

In aspects, the surgical tool may include a microfinger in accordance with the present disclosure having a substantially elongate structure and a length, electrically and mechanically coupled with the delivery member, configured so as to bias at least a portion thereof against the bladder wall upon deployment from within the bladder. In aspects, the microfinger may include one of the sensing tips, configured to bias the sensing tip towards the bladder wall upon deployment from within the bladder. In aspects, the microfinger may include an electrically conducting core extending along the length thereof and an electrically insulating clad layer surrounding the core. In aspects, the system may include more than 100 microfingers, more than 500 microfingers, more than 1,000 microfingers, etc.

In aspects, the tool may be configured to deliver a tissue visualizing medium in accordance with the present disclosure to the target region and/or one or more of the tissue surfaces. In aspects, the tool may be coupled to a display, configured to convey a visualization of the signals, the target region, or one or more of the tissue surfaces to a user.

In aspects, the tool may be configured to perform a urodynamic study on the bladder, one or more of the sensing tips configured to monitor the effect of urodynamic study on the associated tissue surfaces and/or the target region. In aspects, the tool may include a processor, configured to analyze the signals to generate the target region.

In aspects, the therapy delivery element may be configured to modulate at least one of micturition, incontinence, frequency, pain, nocturia, or bladder capacity, and/or configured to modulate neural activity in at least a portion of the bladder wall.

According to aspects there is provided, use of a surgical tool in accordance with the present disclosure, to modulate electrophysiological activity in at least a portion of the bladder or urethra.

According to aspects there is provided, use of a surgical tool in accordance with the present disclosure, to perform a surgical procedure on a subject.

According to aspects there is provided, use of a microsurgical tool in accordance with the present disclosure, to treat overactive bladder (OAB), interstitial cystitis (IC), bladder cancer, or ureteral stent pain/voiding dysfunction.

According to aspects there is provided, a method for determining the electrophysiological function of a bladder, including monitoring electrophysiological activity at a plurality of sites within the bladder during a urodynamic test, monitoring one or more of bladder fill pressure or volume during the urodynamic test, and comparing the monitored activity with the fill pressure or volume.

In aspects, the method may include generating a metric from the monitored electrophysiological activity and bladder fill pressure or volume, the metric being representative of electrophysiological function of the bladder, comparing activity measured at one of the sites to the metric to determine if the site exhibits abnormal activity, generating a map of the electrophysiological functionality of the bladder from the monitored activity alone or in combination with the metric, and/or determining if one or more of the sites would benefit from therapy.

In aspects, the method may include applying a neural block to one or more of the sites and re-evaluating electrophysiological function of the bladder. In aspects, the method may include comparing activities before and after the neural block to determine if a permanent surgical procedure is warranted.

In aspects, one or more one or more of the steps of the method may be performed using a surgical tool in accordance with the present disclosure.

According to aspects there is provided, a method to modulate bladder function, including monitoring a first electrophysiological activity at one or more sites within the bladder, applying therapy to a target region of the bladder, monitoring a second electrophysiological activity at one or more sites within the bladder, and comparing the first monitored activity and the second monitored activity to determine if the therapy was successful.

In aspects, the method may include applying additional therapy to the target region and/or applying therapy to an alternative target region if the therapy was determined to be unsuccessful, selecting the target region based upon the first monitored activity, selecting an alternative target region based at least in part upon the second monitoring activity.

In aspects, the monitored electrophysiological activity may include one or more of water concentration, tissue tone, evoked potential, remotely stimulated nervous activity, a pressure stimulated nervous response, an electrically stimulated movement, sympathetic nervous activity, an electromyographic signal [EMG], a mechanomyographic signal [MMG], a local field potential, an electroacoustic event, vasodilation, bladder wall stiffness, muscle sympathetic nerve activity [MSNA], central sympathetic drive, nerve traffic as measured in the vicinity of the bladder, urethra, spine, uterus, or rectum, combinations thereof, or the like.

In aspects, the method may include mapping electrophysiological activity in the bladder using the first monitored activity, and/or applying a stimulus to a tissue in neurological and/or neuromuscular communication with the bladder. In aspects, the method may include recording electrophysiological activity before, during, and/or after the stimulus to determine the effects thereof on the bladder.

In aspects, the method may include applying a neural block to a region of the bladder. In aspects, the method may include recording electrophysiological activity before, during, and/or after the neural block to determine the effects thereof on the bladder, and/or assessing if the change in electrophysiological activity caused by the neural block is desirable, if so, delivering sufficient therapy to the region so as to form a substantially irreversible neural block.

In aspects, the therapy may be delivered in the form of a radio frequency current, cryoablation, an ultrasonic wave, a microwave, a chemical agent, or thermal energy.

In aspects, one or more one or more of the steps of the method may be performed using a surgical tool in accordance with the present disclosure.

According to aspects there is provided, an implantable device for monitoring electrophysiological activity within a bladder, including a housing including a microcircuit configured to acquire and communicate signals and a power supply or energy harvesting element to provide power to the microcircuit, the housing configured and dimensioned for placement within and attachment to a wall of the bladder, and one or more sensing tips electrically coupled with the microcircuit configured to interface with the wall of the bladder, the sensing tips configured to convey one or more electrophysiological signals associated with the activity to the microcircuit.

In aspects, the electrophysiological signals may be related to one or more of water concentration, tissue tone, evoked potential, remotely stimulated nervous activity, a pressure stimulated nervous response, an electrically stimulated movement, sympathetic nervous activity, an electromyographic signal [EMG], a mechanomyographic signal [MMG], a local field potential, an electroacoustic event, vasodilation, bladder wall stiffness, muscle sympathetic nerve activity [MSNA], central sympathetic drive, nerve traffic, combinations thereof, or the like.

In aspects, the implantable device may include a pressure sensor electrically coupled with the microcircuit configured to measure a fill pressure within the bladder.

In aspects, one or more sensing tips may include a microelectrode configured to interface with the associated wall of the bladder, the microelectrode having an area of less than 5000 $\mu m^2$, less than 1000 $\mu m^2$, less than 250 $\mu m^2$, or less than 100 $\mu m^2$, and/or one or more stimulating electrodes, electrically coupled with the housing, arranged so as to interface with the wall of the bladder, the stimulating electrodes configured to provide a stimulating and/or ablating current to the wall of the bladder.

In aspects, the implantable device may include a plurality of stimulating electrodes, each stimulating electrode electrically coupled with the microcircuit configured to coordinate stimulating and/or ablating currents between two or more of the stimulating electrodes via the wall of the bladder.

In aspects, one or more of the sensing tips may be configured so as to monitor the effect of the stimulating and/or ablating current(s) on the wall of the bladder.

In aspects, the implantable device may be configured to deliver a therapeutic substance in accordance with the present disclosure to the wall of the bladder. In aspects, one or more of the sensing tips may be configured to monitor the effect of the therapeutic substance on the bladder. In aspects, the therapeutic substance is selected from a chemical, a drug substance, a neuromodulating substance, a neuroblocking substance, an acid, a base, a denervating agent, or a combination thereof. In aspects, the therapeutic substance is a selected from a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, capsaicin, an anesthetic, lidocaine, tetanus toxin, quaternary ammonium salts, a pachycurare, a leptocurare, acetylcholine, aminosteroids, or a combination thereof. In aspects, the therapeutic substance may be included within a restraining matrix in accordance with the present disclosure. In aspects, the restraining matrix is at least partially biodegradable.

According to aspects there is provided, use of one or more devices, systems, and/or methods in accordance with the present disclosure to treat overactive bladder (OAB), interstitial cystitis (IC), bladder cancer, ureteral stent pain/voiding dysfunction, and the like.

BRIEF DESCRIPTION OF THE DRAWINGS

FIG. 3 shows a non-limiting example of a balloon wall in accordance with the present disclosure.

FIGS. 4a-d show aspects of substrates in accordance with the present disclosure.

FIGS. 5a-b show aspects of a surgical tool with flexible wire elements in accordance with the present disclosure.

FIG. 6 shows aspects of a surgical tool with a deployable substrate in accordance with the present disclosure.

FIGS. 13a-c show aspects of a surgical tool in accordance with the present disclosure.

FIG. 14 shows aspects of a device for assessing local physiological response and/or treating a local tissue site in accordance with the present disclosure.

FIGS. 16a-c show aspects of tip electrode configurations for a surgical tool in accordance with the present disclosure.

FIGS. 18a-e show aspects of microfilament tips in accordance with the present disclosure.

FIG. 19 shows aspects of a microfilament array based surgical tool in accordance with the present disclosure.

FIGS. 20a-c show aspects of a microfilament array based surgical tool in accordance with the present disclosure.

FIGS. 21a-c show aspects of measurements made over a surface with a microfilament array based surgical tool in accordance with the present disclosure.

FIGS. 25a-c show aspects of an implantable device in accordance with the present disclosure and a schematic of an implantable device attached within the inner wall of a urinary bladder.

DETAILED DESCRIPTION

Figures 1A, 1B, 2:
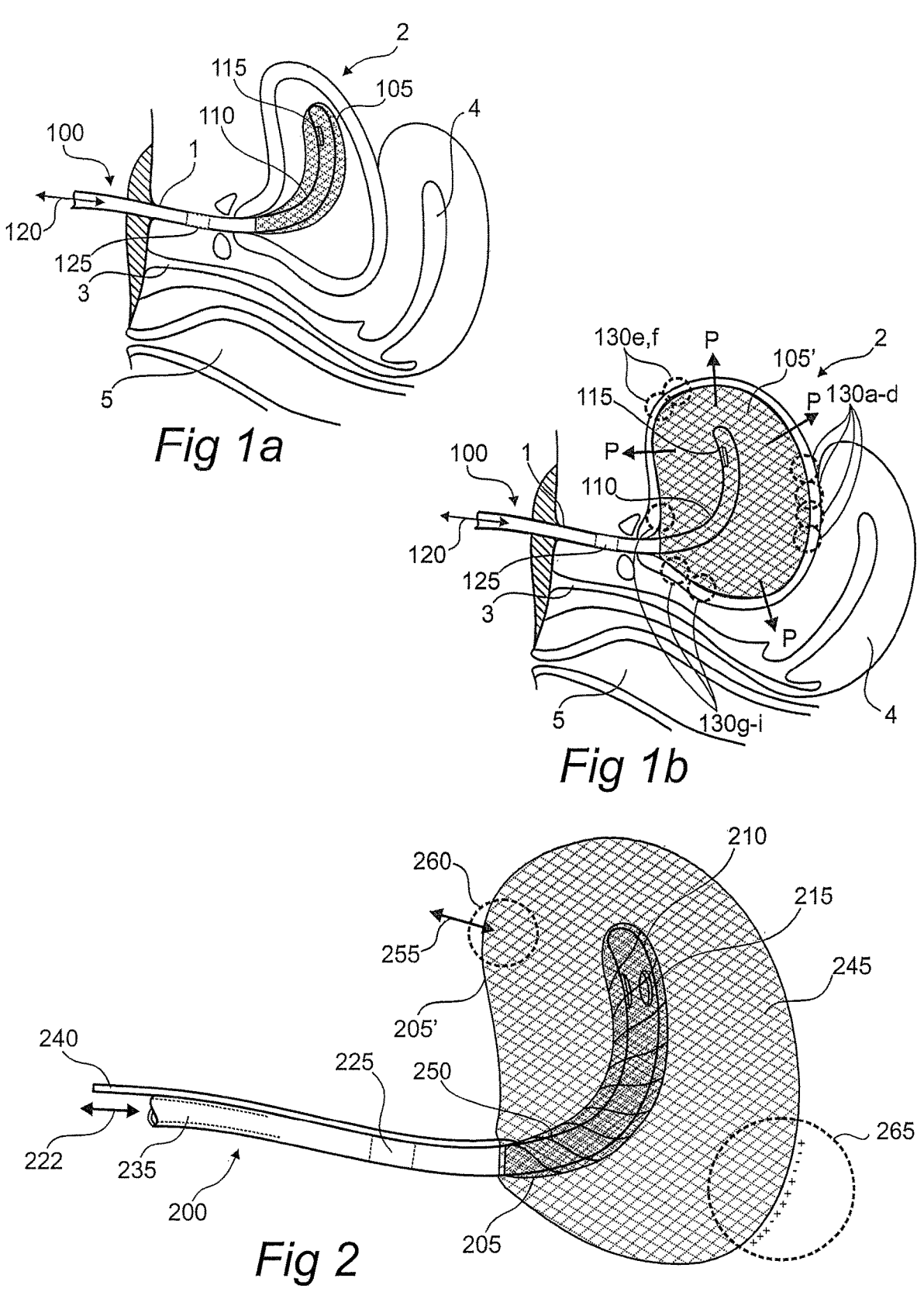
FIGS. 1a-b show aspects of a surgical tool placed within a urinary bladder in accordance with the present disclosure.
FIG. 2 shows aspects of a surgical tool in accordance with the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A controlled denervation system in accordance with the present disclosure may include the capability to sense one or more physiological parameters at one or more points around a surgical site. In aspects, the denervation system may include the capability to stimulate and/or ablate tissues at one or more of the same sites, and/or include the capability to stimulate, deliver a neuromodulating substance, and/or ablate tissues at one or more of the sites and/or an alternative site in the vicinity of a surgical site. In aspects, a nerve ablation system in accordance with the present disclosure may be configured so as to access an internal cavity wall (e.g., the wall of a bladder, a vagina, a uterus, an intestine, a urethra, a colon, a rectum, etc.) in a body. One or more aspects of the non-limiting examples disclosed herein may be directed towards such configurations (e.g., so as to controllably ablate bladder nerves and/or tissues sites along the bladder wall during a surgical procedure).

A controlled nerve ablation system and/or neuromodulation system in accordance with the present disclosure may include one or more sensing tips (e.g., as located on a micro-tip, a wire, an electrode in a matrix, on a flexible balloon, a clamp, a hook-like structure, a net-like structure, etc.). One or more sensing tips may include a pressure sensor, a tonal sensor, a temperature sensor, an electrode (e.g., to interact with a local tissue site, provide a stimulus thereto, measure a potential therefrom, monitor current to/from the tissues, to measure a bioimpedance, measure an evoked potential, neural activity, an electromyographic signal [EMG], an electrocardiographic signal [ECG], a mechanomyographic signal [MMG], a local field potential, etc.), an acoustic sensor, an oxygen saturation sensor, or the like.

The sensing tips may be configured to elucidate a range of key physiological aspects during a procedure. The following description outlines some non-limiting approaches in this respect. Such sensing tips may be integrated into one or more microfingers, micro-tips, clamp faces, tool surfaces, flexible circuits, stretchable substrates, balloon walls, or the like, each in accordance with the present disclosure.

Bioimpedance between one or more sensing tips may be used to determine the degree of contact between one or more of the sensing tips and the anatomical site, as well as potentially the bias force between the sensing tips and the anatomical site. Additionally, alternatively, or in combination, bioimpedance measurements between one or more sensing tips may be useful in determining when adequate contact has been made as well as how much treatment should be applied to an anatomical site during a surgical procedure (e.g., during thermal ablation, RF ablation, ultrasonic ablation, chemical denervation, etc.). Furthermore, additionally, alternatively, or in combination bioimpedance between one or more sensing tips may be used to determine the status of tissue positioned there between. In one non-limiting example, the bioimpedance spectrum between two or more sensing tips may be used to map the local tissue impedance. Such information may be useful to elucidate where such tissue has been completely treated (e.g., ablated, abraded, etc.), where tissue has yet to be treated, etc.

In aspects, bioimpedance measurement between one or more sensing tips, a sensing tip and a separate electrode, etc. may be used to determine a state of isolation between one or more of the sensing tips and a local fluid (i.e., to determine a state of isolation between a sensing tip and fluid within a lumen, to determine the state of contact between one or more sensing tips and an organ wall, to determine the filled state of an organ, etc.).

In aspects, one or more sensing tips in accordance with the present disclosure may be configured to obtain mechanomyographic information during a procedure as determined by slight changes in an associated strain measurement, tip vibration, and/or contact force measurement (e.g., via direct force measurement between the tip and the local anatomy, and/or via changes in the deformation of the microfinger as measured by an associated micro strain gage attached thereupon). Mechanomyographic information may be related to local nervous activity either naturally occurring or in response to a stimulus (e.g., optionally applied by one or more sensory tips, locally, remotely, during and/or via a local RF pulse, etc.). In aspects, a sensing tip may include a piezoresistive strain gauge, a piezoelectric microtransducer, an interfacial pressure sensing membrane, or the like to detect mechanomyographic signals. In one non-limiting example, the sensing tip may be coated with a micro or nano coating of a piezoresistive and or piezoelectric material (e.g., a piezoelectric polymer, an electret, a nano-particulate filled elastomer, a conjugated polymer, etc.). In aspects, the mechanomyographic tip may be configured so as to measure one or more aspect of the tissue compliance of the local tissues (e.g., so as to identify calcified material, cancerous tissues, etc.).

In aspects, a sensing tip, an associated microfinger, and/or an associated electrical interconnect (e.g., a wire interconnect, a printed interconnect, a patterned interconnect, etc.), may include one or more piezoresistive material. A change in impedance of the piezoresistive material during a procedure may be used to determine one or more myographic physiological responses (e.g., movement, neurologically induced activity, etc.) associated with one or more aspects of an associated procedure.

In aspects, the mechanomyographic tip may be configured so as to measure one or more aspect of the tissue compliance of the local tissues (e.g., so as to identify calcified material, cancerous tissues, tissues with increased connective tissues, local changes in wall thickness, etc.).

In aspects, one or more sensing tips in accordance with the present disclosure may be configured to monitor an electrophysiological signal. Such electrophysiological monitoring at and/or between one or more sensing tips, may be used to map nervous response, electromyographic response (EMG), evoked potential, local field potential, extracellular field potentials, etc. along and/or within the wall of the local anatomical site (e.g., the wall of a lumen, along the wall of an organ, along a bladder wall, within an intestinal wall, near a ganglion, in the vicinity of a nerve plexus, etc.). Such information may be advantageous for selecting tissues on which to perform a surgical procedure (e.g., an ablation procedure, a neuromodulation procedure, signal interruption, chemical delivery, an abrasive procedure, a biopsy, etc.), to follow and/or map a nerve along the length of the surgical site, to determine the state of a surgical procedure, etc. In aspects, one or more sensing tips may be configured to monitor a local electromyographic (EMG) signal before, during and/or after a surgical procedure as a means for monitoring local nervous activity (i.e., muscular activity associated with nerve traffic, etc.). In such aspects, the EMG signals may be used as feedback for monitoring the extent of a denervation or neuromodulation procedure.

In aspects, one or more sensing tips in accordance with the present disclosure may be configured to monitor the tone of a tissue within a body. Monitoring the tone (e.g., mechanical properties, wall stiffness, elastic spectral response, mechanical impedance, physiological properties, etc.) of the adjacent tissues may be determined by combining strain and/or force measurement of the sensing tips while applying movement (optionally cyclical or oscillatory movement) to one or more sensor tips. Such sensing tips may be excited locally (e.g., such as by a local piezoelectric transducer, a capacitive transducer, an electrochemical transducer, a smart material, etc.) or globally (e.g., such as by transverse oscillations, axial oscillations, general oscillations of the surgical tool tip, the clamp, the hook, the loop, etc.).

In aspects, one or more of the sensing tips may be interfaced asymmetrically with the associated tissues (i.e., with a bent tip, a micro finger, a wire-like finger configured substantially parallel to the tissue surface, oriented at an acute angle thereto, etc.). By asymmetrically is meant such that the sensing tip approaches the associated tissue surface at an angle other than perpendicular thereto. To describe the use of such a tip to monitor local tissue tone and/or for providing a local excitation (e.g., an electrical excitation, mechanical excitation, etc.) may be applied with relatively small amplitude so as not to generate substantial relative movement between the tissue and the tip during the excitation process (e.g., such that the transverse contact forces remain below the slip conditions between the tip and the tissue, such that they move together during excitation). By relatively small is meant an excitation that is sufficiently small in amplitude such that the sensing tip may not appreciably slide along the tissue surface. In aspects, one or more sensory tips, in a structure attached thereto, and/or a system in accordance with the present disclosure may include a vibratory exciter may be configured to generate the excitation.

In aspects, such a tone monitor may be combined with interfacial contact sensing, electrophysiological measurement, and/or sensor tip strain measurement in order to generate a wealth of local tissue related physiological information before, during, and/or after a surgical procedure. In one non-limiting example, the local tissues may stiffen during an ablation procedure. By monitoring local tissue tone, a stiffness level may be used to characterize when a suitable degree of ablation has been applied so as to irreversibly damage the tissues. Monitoring of a local tissue tone, perhaps at a monitoring site significantly removed from the surgical site such that the surgical procedure does not directly affect tissues in the vicinity of the monitoring site (i.e., does not directly cut, heat, ablate, abrade, the tissues, etc.) may also be advantageous for determining an effect of the surgical procedure on one or more physiological parameters of a tissue (e.g., an organ wall stiffness, change in nerve activity, change in local blood perfusion, etc.) adjacent to the monitoring site.

In aspects, such tone measurement may be useful in determining the local stiffness of tissues (and/or overall wall stiffness of an adjacent vessel, organ, etc.) in contact with a sensing tip array (e.g., so as to determine the type of tissue adjacent to one or more sensing tips, locate plaque, locate a cancerous tumor, etc.). Tone measurement may further be used to characterize the type of tissue with which the tip is interfacing (e.g., muscle, nervous tissue, fat, plaque, cancerous tissue, etc.). In aspects, such information, possibly in combination with bioimpedance data, electrophysiological monitoring, or the like, may be used to determine how much RF energy to apply locally during an RF ablation procedure.

In aspects of a method for RF ablating tissue in accordance with the present disclosure, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored as the tonal measurements may not be significantly affected by the local RF currents.

In aspects, electrophysiological stimulation and/or sensing from one or more sensing tips in a sensing tip array, or a system in accordance with the present disclosure may be used to interface with, monitor and/or stimulate nervous function within a local anatomical structure (e.g., a lumen wall, a vessel wall, along a nerve, an organ wall, a duct, etc.). Such information may be used to hunt for target tissues (e.g., nerves), select tissues for a surgical procedure, to determine the degree of progression of a surgical procedure (e.g., a degree of ablation during RF surgery, etc.), determine interconnection of a neural target with an adjacent organ and/or physiological function thereof, or the like.

In aspects, an array of sensing tips may be configured to apply a directional stimulation and/or multi-site sensing so as to selectively treat/monitor only nerves that are configured to send signals in the preferred direction (e.g., to selectively target primarily efferent nerve bundles, afferent nerve bundles, etc.). Such a configuration may be advantageous for treating a neurological disorder with minimal impact to the surrounding anatomy and physiological function of the associated organs.

In aspects, one or more sensing tips in accordance with the present disclosure may include the capability to apply/receive an RF current to/from the surrounding tissue. The RF current may be provided locally between two of more sensing tips, or alternatively between one or more sensing tips and a macroelectrode placed elsewhere on the body (e.g., on a large skin patch over the surgical site, as selected from multiple patches placed over the body, etc.). In aspects where current may be restricted to being applied between sensing tips, the path for current flow may be well controlled, yet may be highly localized. Alternatively, in an example where RF current is passed between one or more sensing tips and one or more macroelectrodes, the direction of current flow may be more challenging to control, but may be used to access tissues more remote from the sensing tips (i.e., farther into the adjacent tissues, deeper into an organ, farther from a lumen wall, etc.).

In aspects, network impedance measurements between one or more sensing tips and one or more macroelectrodes (e.g., as attached to the body of the patient), may be monitored prior to and/or during application of an RF ablation current. Each sensing tip and/or macroelectrode may include an impedance control circuit that may be adjustable such that the overall current flow through the network formed from all the elements is controlled there through. Such a configuration may be advantageous to more precisely control the local ablation process, thus targeting the local tissues with more accuracy, precision, spatial discrimination, and confidence than less controlled approaches.

In aspects, a plurality of sensing tips may be engaged with the flow of RF current during an ablation process. In aspects, the local impedance of each microfinger and/or sensing tip may be monitored and/or controlled so as to better optimize the current delivered thereto. Additionally, alternatively, or in combination, the local current flow through each sensing tip may be monitored so as to determine the path of the RF current flow, to ensure no leakage currents are detected, etc. Such information may be used to more precisely control the delivery of RF currents to the local anatomy during an ablation procedure.

Additionally, alternatively, or in combination, before, during and/or after the RF current is applied to the surrounding tissues, one or more sensing tips may monitor a physiological parameter (e.g., water concentration, tone, blood oxygen saturation of local tissues, evoked potential, stimulation/sensing of nervous activity, local field potential, extracellular activity, EMG, temperature, etc.) to determine the extent of completion of the intended surgical procedure.

In aspects, one or more sensing tips may include an optical microsensor (e.g., a micropackage including a light source and/or a CMOS photosensor) and/or a fiber optic element. During a surgical procedure, the optical microsensor may be positioned against or near to the local tissues for analysis before, during and/or after an ablation procedure.

In aspects, an optically configured sensing tip (or group of tips) may be configured to locally assess blood perfusion and/or blood oxygenation in the tissues adjacent thereto. The system may be configured to automatically adjust and/or halt the surgical procedure based upon changes in this signal. Alternatively, additionally, or in combination, the system may alert a user (e.g., a surgeon, an attendant, etc.) to a change in this signal before, during, and/or after a surgical procedure. Such a configuration may be useful for assessing local tissue health before, during, and/or after a surgical procedure, the extent of a surgical procedure, etc.

In aspects, one or more optically configured sensing tips may be configured so as to be biased towards the tissues of a lumen, a vessel, or the like in the vicinity of the surgical site. The optical sensing tips may include one or more light sources (e.g., light emitting diodes, fiber optic tips, etc.) configured to deliver narrow, multiband, and/or wideband light to the adjacent tissues. In aspects, one or more of the optical sensing tips may include one or more photodetectors (e.g., a photodetector, a phototransistor, a fiber optic tip, etc.) to receive and/or analyze the light reflected from the adjacent tissues. The received light may be related to that emitted by one or more of the light sources, or may be received from an ambient light source, perhaps located to the exterior of the organ (e.g., external to the organ, remote from the adjacent tissues, from within the bladder cavity, vaginal cavity, rectum, etc.), or the exterior of the subject's body.

The sources may be configured to emit light at predetermined wavelengths such that different absorption characteristics of the adjacent tissues, perhaps dependent on the wavelengths, may be observed during the surgical procedure. The photodetectors may be configured to receive at least a portion of this light, so as to assess the absorption characteristics with the system (perhaps via a pre-amplification system in accordance with the present disclosure, in an attached electronics unit, etc.). The photodetected signals may be used to determine an oximetry value or a signal related thereto.

In aspects, the optically configured sensing tips may be biased towards a site on the exterior of an adjacent vessel wall before, during, and/or after the surgical procedure. Alternatively or in combination, the optically configured sensing tips may be substantially stationary with respect to the vessel wall (such as via being attached to a collar of known size, attached to a structure of known width, as part of a structure that is expanded to a known radius, etc.). In aspects, the magnitude of the bias may be controlled by sensors and actuators both accordance with the present disclosure. Changes in the optical signals detected by the photodetectors (perhaps due to changing bias force) before, during and/or after a surgical procedure may be related to changes in the bias force with which they are held against the vessel wall. Such a configuration may be advantageous for determining a change in sympathetic tone and/or vasodilation before, during and/or after a surgical procedure.

In aspects, the optically configured sensing tips may be coupled with one or more strain and/or interfacial force measurement methods, perhaps to give a more precise reading of the bias force between the sensing tip(s) and the adjacent tissues, to compensate for movement related artifacts, or the like.

In aspects, one or more of the optical sources may be selected such that the penetration of the light into the adjacent tissues may be controlled. In one non-limiting example, a substantially blue wavelength and a substantially red wavelength may be emitted into the tissues. The blue wavelength may provide information relating to the deformation and absorption near to the surface of the tissues, while the red wavelength may penetrate more deeply into the adjacent tissues, providing a signal that changes in response to deformation of tissues farther from the contact site(s) between the tip(s) and the tissue. The photodetectors or equivalent optical detection pathway may include filters, polarized windows, or the like to separately assess the different spectra during an analysis. Comparison between photodetected signals in the blue spectrum with those obtained from the red spectrum may be used to determine tone and/or elastic modulus of the tissues of the vessel in the vicinity of the sensing tip(s). Such a configuration may be advantageous for assessing sympathetic tone (i.e., via muscular tension measurement), and/or vasodilation, organ wall stiffness, and/or local tissue stiffness before, during and/or after a surgical procedure. Changes in such properties may be indicative of the degree of completion of the surgical procedure.

In aspects, an externally placed (e.g., onto the body of the subject) light source (e.g., infrared, near infrared, visible, etc.) may be directed into the body towards the surgical site.

The light source may optionally be modulated to provide a more easily detected signal within the subject. One or more sensing tips equipped with optical microsensors may sense light emitted from the light source. The mapping of received light may be used to locate and/or localize one or more anatomical features such as nerves near to one or more of the optical microsensor equipped sensing tips.

In aspects, one or more externally placed light sources and/or radiation based imaging source may be used to help locate the anatomical sites of interest during the procedure. An external energy source may include a narrow band light source, a broad band light source, radiological source, ultrasonic source, light sources spaced apart from each other, and/or combinations thereof, or the like. The energy sources may be modulated so as to be more easily detectable by sensors located on, in, or near to the anatomy of interest. In one non-limiting example, a plurality of light sources may be aimed at the surgical site from distinct vantage points within the body (i.e., as accessed via an endoscopic procedure, etc.) or externally to the body (i.e., as positioned at locations on the body).

In aspects, an endoscopic camera may be placed near to the anatomy, lumen wall, and/or surgical site of interest during a procedure to observe both the anatomy, as well as placement of the surgical tools in the vicinity of the anatomy. In one non-limiting example, the endoscopic camera and/or light source may provide a suitable macroelectrode for RF ablation processes performed during the surgical procedure.

In aspects, one or more sensing tips may be equipped with a corresponding micro-light source (e.g., an oLED, an LED, etc.). The micro-light source may be used to direct light into the adjacent tissues. One or more sensing tips equipped with optical microsensors may be configured to detect light emitted from the micro-light source as back scattered by and/or transmitted through the adjacent tissues. Such information may be used to detect anatomical features (e.g., nerves, tumors, etc.) in the adjacent tissues, monitor local fluids (i.e., water content, blood flow, etc.), interact with tissue visualizing materials, for inspecting tissues within the organ wall, etc.

Such optical configurations may be advantageous for mapping the local tissues before, during and/or after a surgical procedure. They may also be advantageous for implementation into a nerve detection system (e.g., perhaps as input to a nerve hunting algorithm, etc.). In aspects, such a system may be embodied by an optical coherence tomographic (OCT) configuration.

In aspects, the system may include a micro balloon catheter for placement into an organ (e.g., a bladder, a vagina, a uterus, a rectum, a colon, an intestine, etc.) or within tissues adjacent thereto, etc. The micro balloon catheter may be coated with a thin layer of an indicator molecule. The indicator molecule may be tagged to attach to the target tissue of interest and/or tagged so as to change chromatic properties when bound to the target tissue (e.g., nervous tissue, etc.). The molecules may be delivered to the desired tissues during a balloon catheterization procedure. During such a procedure, the micro balloon catheter may be placed into the organ of interest and inflated so as to kiss the walls of the organ. While in contact with the organ walls, the indicator molecules may attach and migrate/diffuse into the local tissues. Such a procedure may be performed as a first surgical step or as combined with other aspects in accordance with the present disclosure. In aspects, the balloon may also be configured to deliver a therapeutic agent (i.e., a neuroblocking agent, ethyl alcohol, botox, etc.) to the anatomy of interest.

In a method in accordance with the present disclosure, one or more sensing tips may be inserted into a tissue adjacent to a target organ (i.e., a bladder, vagina, colon, uterus, etc.), and/or a lumen with a wall within a body and biased towards the wall of the lumen or the target organ, and one or more electrophysiological signals obtained therefrom. The electrophysiological signals may be analyzed to locate one or more target tissues for a surgical procedure (i.e., one or more sympathetic nerves, parasympathetic nerves, etc.). A bolus of therapeutic agent (e.g., a neural ablative chemical, a neuroblocking substance, a neuromodulating substance, etc.), an RF current, a thermal energy source, and/or the like may be delivered to the identified tissues so as to perform the surgical procedure thereupon. In aspects, one or more post-procedural electrophysiological signals may be analyzed to determine the extent of the surgical procedure.

In aspects, the therapeutic agent may be provided via a micro balloon catheter in accordance with the present disclosure. In aspects, the micro balloon catheter may include one or more sensory tips (e.g., in the form of functional elements attached to the balloon, attached to a superstructure surrounding the balloon, etc.) in accordance with the present disclosure.

In aspects, the bioimpedance and/or electrophysiological signals between one or more sensing tips in the array and one or more sensing tips in the array, an external electrode, a reference electrode, or the like may be used to determine changes in the structure of the adjacent tissues during an ablation procedure. Such information may be useful in determining the extent of the ablation procedure, char accumulation, etc.

In aspects, bioimpedance measurements may be correlated with nerve damage data, perhaps obtained during prior surgeries, development of the procedure, and/or obtained during specific testing procedures, such that changes in local bioimpedance data may be used during a surgical procedure to determine the extent of the ablation procedure. Such a configuration may be advantageous in the case that the surgical procedure itself overwhelms the local electrophysiological activity to the extent that neurological monitoring may be hindered for a prolonged period of time after the procedure has been completed.

In aspects, one or more sensing tips may be configured to monitor local electrical fields during an ablation procedure in accordance with the present disclosure in order to better determine the current flow path through the adjacent anatomy, perhaps connected to a warning system to indicate to an operator when the ablation field is insufficient for achieving the intended goal. Such a configuration may be advantageous for avoiding unnecessary damage to the tissues during a misfired or misdirected ablation session.

In aspects, a system in accordance with the present disclosure may include a micro balloon catheter including one or more sensory tips (e.g., in the form of functional elements attached to the balloon, attached to a superstructure surrounding the balloon, etc.). The micro balloon catheter may be configured so as to bias the sensory tips against the adjacent organ walls, thus providing a reliable interface from which selective ablation and detection processes may be performed. Such a micro balloon catheter may be advantageous for single placement type surgical procedures in accordance with the present disclosure.

In aspects including a plurality of sensing tips (e.g., as placed onto a micro balloon catheter, surgical tools, a clamp, a hook, a loop, a microfinger array, a microtool set, a flexible cage assembly, a balloon wall, a flexible cage assembly, etc.) the sensing tips may be interconnected with each other, with signal processing circuitry, a local microcircuit, and the like and/or combinations thereof. In order to substantially reduce the number of signal wires that must be sent to the surgical site during the procedure, the networked array of sensing tips may be multiplexed together with a locally placed microcircuit (e.g., an application specific integrated circuit, distributed/interconnected circuit elements, a collection of flexible semiconducting circuit elements, etc.). The microcircuit may be configured to communicate such signals with an extracorporeal system (e.g., a computer, a control system, an RF ablation controller, a data acquisition system, etc.). The microcircuit may be configured to communicate with the extracorporeal system via analog and/or digital means and/or methods. In one non-limiting example, the communication may be of primarily digital means such that the microcircuit may exchange data pertaining to any sensing tip in the array, as well as switch data, control data, RF pulse routing, etc.

In aspects, the networked array of sensing tips may be interconnected with distributed electronic elements and flexible electrical interconnects (e.g., as applied to a balloon wall, as provided by structural wires, microfingers, wire mesh elements, etc.). In aspects, one or more of the sensing tips, microfingers, or the like may be included upon a flexible or stretchable electronic substrate, the electronic substrate configured to interface the sensing tips with the anatomy as well as to electrically connect one or more sensing tips, or the like with a controller, a control system, an operator, a graphical user interface, a display, or the like.

A controlled nerve ablation system in accordance with the present disclosure may include one or more microfingers.

To this effect, a microfinger array microsurgical tool is disclosed herein. Any element in the microfinger array may include a sensing tip in accordance with the present disclosure to interact with the local anatomy during a surgical procedure.

The microfinger array may be advantageous for accessing very small anatomical sites within a body, for highly localized interaction with a tissue site, etc.

In aspects, a microfinger array may be arranged in a surgical tool in accordance with the present disclosure such that one or more of the microfingers may substantially independently interface with the adjacent tissues. Thus if an array of microfingers is placed against a rough or otherwise uncontrolled surface, each microfinger may be able to contact, maintain a controlled bias force against, substantially embed an associated sensing tip into, and/or substantially maintain contact with the surface during use, even if the microfinger array is dragged along the surface as part of a procedure, during movement of the surface, etc. Such independently adjustable microfingers may be advantageous so as to maintain a known interfacial pressure, especially while monitoring, stimulating and/or ablating the tissue with the microfingers. Such independently adjustable microfingers may be advantageous to substantially embed an associated tip (i.e., an associated sensory tip) into an adjacent tissue during a procedure.

By microfinger is meant a substantially curved finger like member (i.e., with curvature at one or more points along the length thereof, with multi-axial curvature, etc.). Such microfingers may generally have a characteristic width (although may be of any cross sectional makeup). The microfingers may generally have characteristic widths on the order of approximately 1 mm, 0.5 mm, 0.1 mm, 0.05 mm, 0.01 mm, or the like. In one non-limiting example, one or more microfingers may include a Nitinol structure (e.g., a wire, a ribbon, etc.) with characteristic width of approximately 100 um, approximately 50 um, approximately 25 um, etc.

In aspects, one or more regions of a microfinger in accordance with the present disclosure may be selectively coated with an isolation layer (e.g., an oxide layer, a dielectric coating, a polymer layer, a lubricious layer, etc.). In aspects, such an isolation layer may be selectively applied to regions of the microfingers (i.e., so as to create isolated regions and sensitive regions thereof).

In aspects, the microfingers may be configured so as to deploy and/or bias against one or more adjacent tissue structures during a procedure and may be used to contactably sweep the local anatomy, for purposes of sensing, stimulating, and/or ablating during a surgical procedure. In aspects, one or more microfinger dimensions and structure may be designed so as to provide substantially uniform and predictable bias forces on the adjacent tissues over a wide range of movements and dimensional variation.

In aspects, an array of microfingers in accordance with the present disclosure may be configured so as to sufficiently collapse down into a delivery catheter while expanding outwards upon deployment so as to form a controllably biased contact within an anatomical structure (e.g., an organ, etc.) or for convenient delivery to a surgical site (e.g., within tissues surrounding a bladder, a uterus, a vagina, a rectum, etc.).

In aspects, one or more microfingers in accordance with the present disclosure may be configured into the shape of a wire basket, a mesh-like structure, or the like. In aspects, one or more regions of such microfingers may be patterned with an isolation layer, so as to direct signals over the microfingers, towards associated sensing tips, to provide communication between associated sensing tips and control electronics, to control one or more mechanical properties thereof, or the like.

Such a configuration may be advantageous for accessing anatomical sites of interest with minimal damage, while also maintaining consistent contact forces at a surgical site during a procedure, substantially embedding one or more sensory tips into an organ wall, tissue structure of interest, substantially isolating one or more sensing tips from an adjacent fluid, or the like.

In aspects, a microfinger array in accordance with the present disclosure may include a plurality of fingers, one or more such fingers configured to interface with the surrounding tissues and biased radially outwards from a deployment site (e.g., a guide wire, a catheter, etc.). In aspects, the microfinger array may be deployed via longitudinal retraction of a restraining shell (i.e., a restraining layer in the catheter), via application of heat or current (i.e., in the case of a shape memory microfinger, etc.), via projection of the microfinger array out of a delivery catheter (i.e., by advancing the microfinger array beyond the tip of the delivery catheter, etc.).

In aspects, one or more microfingers may include a spring-like wire element (e.g., Nitinol, spring steel, etc.) and/or may include composite structures including a spring-like element to provide a bias force so as to push the tip and/or one or more regions of the microfinger towards the wall of an organ into which it is placed (i.e., towards a surface, etc.).

In aspects, a microfinger may include a Nitinol structure, optionally configured for passage of current flow, to and from the surrounding tissues, and/or communication of electrophysiological information between an associated sensing tip and a connected microcircuit. In aspects, the Nitinol structure may be configured such that, when an RF pulse is applied there through towards the surrounding tissues, the Nitinol structure may retreat from the tissues after a predetermined amount of energy has passed there through, upon reaching a predetermined temperature, or the like. Thus the Nitinol structure may provide an inherently controlled method for applying a quantum of RF energy to the surrounding tissues. Such a configuration may be adapted for use simultaneously, additionally, alternatively and/or in combination with one or more of the other aspects described in this disclosure.

In aspects, each finger in the array may move somewhat independently of the others such that all fingers may maintain contact with an organ wall, a target tissue, or the like, during a procedure.

Such a configuration may be advantageous for maintaining robust contact with the interior and/or exterior walls of a muscular organ (i.e., a bladder, a uterus, a vagina, etc.), while performing a procedure (i.e., scanning a surface with one or more microfingers, dragging a microfinger along a surface, monitoring a tissue site, ablating a tissue site, etc.) or during periods of relative movement (i.e., in the presence of organ movement, perhaps due to physiological processes, stresses related to biorhythms, breathing, blood pressure variation, contractions, etc.).

In aspects, the microfingers may be formed slightly off axis to a delivery catheter, such that relative axial movement of an overlying sheath may be used to retract the microfingers into the sheath or conversely to deploy them towards the anatomical site. Additionally, alternatively, or in combination, off axis arrangements may provide the capability to sweep the microfingers circumferentially along the anatomical site via applying torsion to catheter to which they are attached.

Such a configuration may be advantageous for simultaneously mapping and selectively ablating an anatomical site during a surgical procedure.

Furthermore, such a configuration may be advantageous for working upon an anatomical site, while maintaining flow of fluid there through (i.e., as opposed to an occlusive tool, which may block flow during expansion thereof).

In aspects, one or more microfingers may be provided with highly miniaturized and flexible structure so as to more easily access highly restricted anatomical sites within the body, and/or so as to reach surgical sites of interest with minimal damage to the surrounding tissues.

In aspects, one or more microfingers may include one or more sensing tips in accordance with the present disclosure for capturing information from the local surgical site. Some non-limiting examples of sensing options include temperature sensors, electrodes, strain gauges, contact force sensors, combinations thereof, and the like. For purposes of discussion, a sensing tip may also be referred to as a microsensor.

The sensing tips may be configured to elucidate a range of key information during a procedure. Some aspects are discussed in more detail below.

Bioimpedance between one or more microfinger tips may be used to determine the degree of contact between the finger tips and the anatomical site, the water content of tissues between the microfinger tips, the state of tissues between the microfinger tips, as well as potentially the bias force between the finger tips and the anatomical site. Such information may be useful in determining when adequate contact and to gauge how much current should be applied to an anatomical site during an ablation procedure.

Mechanomyographic information may be obtained from fingertips during a procedure as determined by slight changes in an associated strain measurement and/or contact force measurement (e.g., via direct force measurement between the tip and the local anatomy, and/or via changes in the deformation of the microfinger as measured by an associated micro strain gage attached thereupon).

Evoked potential monitoring at or between one or more finger tips, may be used to map nervous response, electro-myographic response, extracellular potentials, local field potentials, evoked potential, etc. along the wall of the local anatomy (e.g., vessel wall, organ wall, etc.) or within tissues associated with the surgical site, etc. Such information may be advantageous for selecting tissues on which to perform a surgical procedure (e.g., an ablation procedure, a biopsy, a stimulation procedure, a chemical delivery event, etc.).

The tone of the adjacent tissues may be determined by combining strain and/or force measurement of the microfin-gers while applying an excitation to one or more microfin-gers (e.g., optionally clockwise torsion to advance the microfingers and small counterclockwise torsion to measure the tone of adjacent tissues, a vibratory exciter in combina-tion with contact and/or microfinger strain measurement, etc.).

Such tone measurement may be useful in determining the local stiffness of tissues in contact with the microfinger array (e.g., so as to determine the type of tissue adjacent to one or more microfingers, to monitor local stiffness changes in response to a surgical procedure, to locate plaque, to locate a cancerous tumor, etc.).

Stimulation and sensing from one or more microfingers in the microfinger array may be used to elicit nervous function of local anatomy. Such information may be used to select tissues for a surgical procedure, to determine the degree of progression of a surgical procedure (e.g., a degree of abla-tion during RF surgery, effect of a chemical substance delivered into the surrounding tissues, etc.). Directional stimulation and sensing may be used to selectively treat only nerves that are configured to send signals in the preferred direction (i.e., via combination of stimulation and/or sensing from a plurality of sensing tips, sensing sites, etc.).

In aspects, one or more microfingers may include the capability to apply/receive an RF current to/from the sur-rounding tissue.

Such RF currents may be applied between one microfin-ger in the array and an (optionally) distant counter electrode, between two or more microfingers in the array, to a extra-corporeal patch on the body, etc.

In aspects pertaining to multiple microfinger RF current passage, the local impedance of each microfinger may be altered so as to control the current delivered thereto.

In aspects pertaining to multiple microfinger RF current passage, the local current flow through each microfinger may be monitored so as to determine the path of the RF current flow, to ensure no leakage currents are detected, etc. Such information may be used to more precisely control the delivery of RF currents to the local anatomy during an ablation procedure.

In aspects, prior to, during, and/or after the RF current is applied to the surrounding tissues, one or more microfingers may be configured to monitor a physiological parameter (e.g., water concentration, tone, blood oxygen saturation of local tissues, evoked potential, one or more local field potentials, stimulation/sensing of nervous activity, EMG, temperature, etc.) to determine the extent of completion of the intended surgical procedure.

In aspects, the bioimpedance between one or more microfingers in the array may be used to determine changes in the structure of the adjacent tissues during an ablation procedure. Such information may be useful in determining the extent of the ablation procedure, char accumulation, changes in tissue impedance, etc.

In aspects, bioimpedance measurements may be corre-lated with nerve damage data, perhaps obtained during prior surgeries or obtained during specific testing procedures, such that changes in local bioimpedance data may be used during a surgical procedure to determine the extent of the procedure. Such a configuration may be advantageous in the case that the surgical procedure itself overwhelms the local electrophysiological activity to the extent that neurological monitoring may be hindered for a prolonged period of time after the procedure has been completed.

In aspects, one or more microfingers may be configured to monitor local electrical fields during an ablation procedure in order to better determine the current flow path through the adjacent anatomy, perhaps connected to a warning system to indicate to an operator when the ablation field is insufficient for achieving the intended goal, to assist with the direction of energy towards the intended surgical site, to conserve energy, etc. Such a configuration may be advantageous for avoiding unnecessary damage to the tissues during a mis-fired ablation session.

In aspects, the system and/or microfingers may include a coolant delivery system (e.g., a saline delivery system) in order to cool the microfingers during and/or after an ablation procedure. Such coolant delivery may be advantageous for minimizing char and excessive damage associated with an ablation procedure. In aspects, such coolant delivery may be part of a cryogenic surgical procedure (i.e., cryoablation), or the like.

In aspects, one or more microfingers may include an exposed electrode area (i.e., as part of an electrode based sensing tip) that only touches the walls of the adjacent anatomy. Such a configuration may be advantageous for minimizing current flow into the adjacent fluids within the vessel (i.e., to substantially isolate the electrode from fluids within an organ, etc.), to better control RF current flow in the vicinity of the electrodes, minimize conductivity between the exposed area and the surrounding fluid, so as to sub-stantially embed the exposed electrode area in to the wall of the adjacent anatomy, etc.

In aspects, one or more microfingers may include one or more active material elements. Control signals delivered to the active material element may help to bias the microfingers towards the intended surgical site, actively control the contact forces between finger tips and the surgical sites, etc. Some non-limiting examples of active materials that may be suitable for application to one or more microfingers include shape memory materials (e.g., shape memory alloys, poly-mers, combination thereof), electroactive polymers (e.g., conjugated polymers, dielectric elastomers, piezoelectric polymers, electrets, liquid crystals, graft elastomers, hydro-gel actuators, etc.), piezoceramics (e.g., amorphous piezo-ceramics, single crystals, composites, etc.). In addition the active material may be used as a vibratory exciter and/or mechanical probe, for use in monitoring the tone of the adjacent tissues (see above), alternatively, in addition or in combination, to cause vibratory/ultrasonic ablation and/or local heating to the tissues. In such aspects, the active material may be included along the length and/or over a region of the microfinger (i.e., so as to influence the shape of the microfinger during contraction or expansion of the active material).

In aspects, one or more sensing tips may include a conjugated polymer electrode to interface with the adjacent tissues. Some non-limiting examples of suitable conjugated polymers include polyaniline, polypyrrole, polyacetylene, poly(3,4-ethylenedioxythiophene), and the like.

In aspects, one or more microfingers may include an electrical shield such that the microfinger tips are effectively shielded from other currents flowing through an associated catheter, the body, etc. during a procedure.

In aspects, one or more elements of a microfinger based catheter may include a bidirection switching network, micro amplifier array, a sensory front end, combinations thereof, or the like in order to amplify sensed signals as close as possible to the anatomical interface, to switch the function of a microfinger tip between sensory, stimulatory, and/or ablative functions, perform combinations thereof, or the like. In aspects, the circuitry may be included in the delivery wire within the catheter of the system. In such aspects, the circuitry may be coupled to one or more microfingers and/or sensing tips each in accordance with the present disclosure, and a secondary signal acquisition circuit, a digital communication block, a controller, an RF signal generator, combinations thereof, and the like.

In aspects, a bidirectional switching network may be used to enable bifunctional stimulation/sense capabilities in one or more microfingers, etc. The switching network may be included in a local amplifier array, as a flexible circuit, or silicon die interconnected to or placed upon one or more microfingers, etc. Alternatively, additionally, or in combination, an extracorporeal circuit element may be coupled to the switching network and/or microfingers, sensing tips, etc. and to a controller included within a surgical system including a microfinger array in accordance with the present disclosure.

In aspects, a micro amplifier array may be used to preamplify the signals obtained from one or more sensory aspects of the microfingers, so as to improve the noise signature, etc. during use. The microamplifier may be coupled to the catheter, embedded into the catheter, embedded into one or more microfingers, etc.

In aspects, one or more microfingers in accordance with the present disclosure may be provided such that they are sufficiently flexible so as to buckle, or change orientation during back travel, so as to prevent puncture of the local anatomy. A configuration as outlined in this non-limiting example may be advantageous for providing contact with the local anatomy without significant risk of damaging the adjacent anatomy (e.g., puncturing an organ wall, etc.) which may be a concern with stiffer structures. Such microfingers may include a characteristic width of less than 200 um, less than 100 um, less than 50 um, less than 25 um, less than 10 um.

In aspects, one or more microfingers in accordance with the present disclosure may include a substantially hyper elastic material (e.g., formed from a memory alloy material, a superelastic material, a spring steel, etc.) so as to effectively deploy from a very small deployment tube/catheter and expand outward to accommodate a large range of vessel diameters or changes in shape during deployment. Such a configuration may be advantageous in so far as a small number of unit sizes may be suitable for treating a wide range of anatomical structures. In addition, the designed curvature and form of a microfinger may be substantially chosen so as to further enable a wide deployable range of movement.

A surgical tool including a plurality of microfinger arrays (i.e., clusters of microfingers, fans of microfingers, etc.) may be employed so as to determine physiological response more remotely from an intended surgical site than may be available within a single array. Aspects of the disclosed concepts may be employed along the same lines by extending interactions between microfingers within an array, to inter-array interactions. In aspects, a surgical tool including a plurality of clustered microfinger arrays may be advantageous to analyze one or more anatomical sites simultaneously from a plurality of sites (macroscopically separated sites). In aspects, two microfinger arrays may be arranged along a catheter based surgical tool, so as to interface with the walls of a lumen, at two or more longitudinally separated distances, between a surgical site of interest and a (somewhat) remote location, or the like. Physiological sensing from multiple microfingers may be advantageous for determining the extent of neurological traffic between the plurality of sites, determine the direction of traffic, determine if traffic from one direction or the other is blocked (i.e., after a surgical procedure, after RF current application, after a denervation procedure, etc.). Such configurations and methods for determining the state of a plurality of anatomical sites is further disclosed throughout the text and appended figures of this disclosure.

In aspects, a system in accordance with the present disclosure may be used to monitor physiological activity associated with a surgical site prior to, during and/or after a surgical procedure is applied thereto. Some suitable examples of surgical procedures include an RF ablation, Argon plasma coagulation, laser ablation, water jet ablation, ultrasonic ablation, cryoablation, microwave ablation, abrasion, biopsy, delivery of a substance (e.g., a chemical, a drug substance, a neuromodulating substance, a neuroblocking substance, a neurotoxin, an acid, a base, a denervating agent, etc.), combinations thereof, and the like. The local physiological activity (e.g., nervous activity, blood perfusion, tonal changes, muscular sympathetic nerve activity, etc.) may be monitored with one more sensors (sensing tips, microfingers, etc.), perhaps in combination with one or more physical sensors (i.e., temperature sensors, pressure sensors, etc.), and/or associated stimulators each in accordance with the present disclosure. Additionally, alternatively, or in combination, a technique for assessing one or more physiological properties and/or states of an associated surgical site may be employed. Such techniques include assessing values and/or trends in bioimpedance, blood pressure, tissue oxygenation, tissue carbon dioxide levels, local temperatures, combinations thereof, changes thereof, and the like.

In aspects, the system may include a substrate onto which the sensing tips may be placed. Such a substrate may be formed from a balloon wall, a mesh, an interwoven ribbon array, a cloth, a clamp face, a hook face, etc. In aspects, the substrate may include stretchable and/or flexible electronic materials.

Electrical interconnects may be formed from carbon nanotubes (e.g., SWNTs, MWNTs, etc.), nanowires, metallic wires, composites, conductive inks, patterned versions thereof, combinations thereof, and the like.

In aspects, a portion, or all of the substrate and/or an associated substrate carrier film may be formed from polyurethane, a silicone, a general elastomer, silk fibroin materials, combinations thereof, or the like. Inclusion of microporous or fibrous substrates may be advantageous to allow the substrate or substrate carrier film to adhere to the adjacent tissues via capillary effects (i.e., tendencies to wick fluid from adjacent tissues into the substrate). In aspects, the thickness of films formed from the material may be less than 50 um thick, less than 30 um thick, less than 20 um, less than 10 um, less than 4 um, less than 1 um. Composites of somewhat stiffer materials (such as polyimide, PET, PEN, etc.) and somewhat softer materials (e.g., silicones, polyurethanes, thermoplastic elastomers, etc.) maybe used to compromise between overall structural stiffness and conformal capabilities of the substrate.

In aspects, patterned overcoats and/or composite layers may also be used to expose electrode materials and/or sensing tips to the surrounding tissues in the vicinity of measurement regions, etc.

In aspects, a substrate in accordance with the present disclosure may be formed from a silk material (e.g., *Bombyx mori* cocoons). The material may be processed to remove sericin (which may cause undesirable immunological response) using methods known in the art. The resulting material can be solvent cast into shapes and crystallized to form self-supporting structures.

In aspects, adaptive temperature estimation may be used to better control the RF ablation process. Such techniques may be supported by use of a surgical tool in accordance with the present disclosure, including one or more sensing tips configured with temperature and/or bioimpedance monitoring aspects. Modeling of changes in local bioimpedance may be related to local temperature changes during the ablation process. Such measurements as well as local thermoconductive properties, tissue thermoconduction, etc. may also influence the rates at which a local ablation process may take place (i.e., as related to a thermal ablation process).

In aspects, a system in accordance with the present disclosure may include one or more microsensors for monitoring nervous activity and/or related physiological activity before, during, and/or after the surgical procedure. Some non-limiting examples of suitable monitoring techniques include electromyography (EMG), muscle sympathetic nerve activity (MSNA), mechanomyography (MMG), phonomyography (PMG), extracellular potentials, local field potentials, combinations thereof, and the like. Mechanomyography (MMG) measures the force created by local muscle contractions caused by associated neural activity. Phonomyography (PMG) measures low frequency sounds associated with movement generated by associated neural activity. Traditionally, techniques such as MMG and PMG have been employed on externally accessible nervous and muscular tissues. One advantage of such techniques is that they may not be as easily affected by local electrical noise as EMG and the effects of the nervous activity may be generally sensed farther from the associated nerve than with electromyographic techniques.

Alternatively, additionally or in combination the ascribed sensing techniques may be combined with stimulation from local sources in accordance with the present disclosure. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (e.g., the successive stimulation and sensing may be used to determine the degree of neurological block and/or neuromuscular block there between). In aspects, such functionality as well as directionality of the nerve signal propagation (e.g., efferent, afferent, etc.) may be more easily determined through use of combined local stimulation and sensing.

In aspects, one or more patterns of nerve stimulation may be used to determine the function of the local nerve structures as well as one or more aspects of neurological block and/or neuromuscular block that may be caused by the surgical procedure (e.g., ablation), anesthesia, heating, chemical delivery, a related condition, etc.

In aspects, a single stimulation may be applied to elicit maximal response from the associated nerve at frequencies of less than 10 Hz, less than 1 Hz, less than 0.1 Hz. The downstream response as measured by any of the described techniques will depend on the frequency with which the stimuli are applied. In aspects, in order to allow for complete recovery of the nerve between stimulations, a frequency of less than or equal to 0.1 Hz may be advantageous.

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, to control the extent of a denervation procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e., a suitable metric for determining how a procedure has affected that nerve).

In aspects, the sensing of the nervous response may not need to be local to a surgical site, but rather downstream (in the sense of the flow of an associated nervous signal) from the site. Such sensing of the nervous response may be advantageous for determining the progression of a particular form of communication past a surgical site (i.e., afferent, efferent traffic, etc.).

In aspects, various mapping techniques may be applied to the surgical site, before, optionally during, and/or after a surgical procedure. Some mapping techniques as used in cardiac interventions include pace mapping, activation mapping, entrainment mapping, and substrate mapping. It may be feasible to adapt such techniques for use in the intended application and/or a system in accordance with the present disclosure. In general, these techniques may complement each other in localizing where amongst a surgical site to target the ablation procedure.

Additionally, or in combination to the aspects described herein, the surgical system may be configured to monitor one or more physiological parameters at one or more locations in the body remote from the surgical site. Some non-limiting examples of what may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g., bursts per minute, bursts per heartbeat, etc.), tissue tone, blood flow (e.g., through an artery, through a renal artery), a blood flow differential signal (e.g., a significantly abnormal and or sudden change in blood flow within a structure of the body, a vessel, an organ, etc.), blood perfusion (e.g., to an organ, an eye, etc.), a blood analyte level (e.g., a hormone concentration, norepinephrine, catecholamine, renine, angiotensin II, an ion concentration, a water level, an oxygen level, etc.), nerve traffic (e.g., post ganglionic nerve traffic in the peroneal nerve, celiac ganglion, superior mesenteric ganglion, aorticorenal ganglion, renal ganglion, and/or related nervous system structures), combinations thereof, and the like.

In aspects, a surgical system in accordance with the present disclosure may include one or more elements to monitor physiological activity and/or analyte levels (e.g., a hormone level), in and/or near to one or more portions of a gland, an endocrine gland (e.g., an adrenal gland, an adrenal medulla, etc.), at a site within the central nervous system, etc.

In aspects, a multi tool surgical system may be employed, each catheter in accordance with the present disclosure. In one non-limiting example, one or more first tools may be used to probe and/or ablate tissues at a first surgical site (e.g., within an organ, a bladder, an intestine, a vagina, a uterus, a first nerve structure, a nerve plexus, etc.) while one or more second tools may be configured to monitor one or more physiological parameters elsewhere in the body (e.g., in an artery, a vein, further along the first nerve structure, in an organ, at a lymph node, at a ganglion, etc.), perhaps to determine the effect of the surgical procedure there upon. In one non-limiting example, the tools may be inserted into the same or closely positioned entry points into the body (e.g., a body opening, a urethra, a vagina, a rectum, one or more transcutaneous entry points, etc.). Such a configuration may be advantageous for providing a minimally invasive surgical tool to perform the surgical procedure (e.g., a sympathectomy, a renal sympathectomy, a neuromodulation procedure, etc.).

Some further aspects relating to systems and methods for adjusting (temporarily and/or permanently) nerve function, while substantially minimizing collateral damage to adjacent structures via devices, tools, catheters, and methods are now discussed. References made to ablation may be considered to refer to a general surgical procedure (to cut, heat, cool, excise, chemical delivery, etc.) on a tissue.

Herein the general reference to electrodes, sensors, etc. may equally pertain to sensing tips in accordance with the present disclosure.

A surgical tool in accordance with the present disclosure may include an array of electrodes. The array of electrodes may be used to interface intimately with the local tissues, so as to select ablation sites, validate ablation success, sense local neural activity, stimulate and sense, etc.

Electrodes in the array may be used to stimulate, sense and/or ablate local tissues and/or monitor nervous activity before, during and/or after a related surgical procedure or ablation process.

In aspects, a tool in accordance with the present disclosure may include a switch array in accordance with the present disclosure, optionally with amplifiers such that one or more electrodes could be configured for stimulation, ablation, and/or sensing. The tool may include electronics to monitor bioimpedance between one or more electrodes (i.e., so as to determine when the tool is adequately biased against the intended anatomical structure, etc.).

In aspects, the tool may include electronics for automatically terminating an ablation signal when a change in the sensed nervous activity is detected. In one non-limiting example, a pulsatile stimulation is applied to one side of the ablation zone, perhaps during the ablation process and/or between ablation pulses (and/or perhaps intermixed with the ablation pulses). Another electrode may be placed to the opposing side of the ablation zone so as to monitor nervous response before, during and/or after the ablation procedure.

In aspects, one or more electrodes in an array may be preconfigured so as to provide a particular function, sense, stimulate and/or ablate local tissues.

One or more electrodes in the array may be a monopolar electrode or part of a bipolar pair. In one example, two or more electrodes may be arranged into pairs, multi-polar interconnects, etc.

In aspects, the electrodes may be configured so as to protrude from a face of the tool (e.g., via emboss, plating, filament, matted morphology, application of microfiber structures thereupon, etc.). In aspects, one or more of the microelectrodes may be embossed so as to better bias the interfacing aspects of the tool towards the tissue during a procedure. This may be advantageous to ensure that each electrode applies adequate pressure to the adjacent tissues and/or to improve the chances of tissue contact with a plurality of the electrodes A method for determining the functionality, directionality, location of and/or the extent of nerve function degradation before, during and/or after a surgical procedure may include stimulating a one or more nerves located at a proximal and/or distal location on an organ (e.g., a bladder, an intestine, a uterus, a gland, etc.) in a body; monitoring an evoked response at a location distal and/or proximal to the location of the stimulation; evaluating the signal quality, spectral content, etc. related to the evoked response and/or changes in the evoked response during and/or after the surgical procedure. One or more steps of the method may be performed with one or more surgical tools each in accordance with the present disclosure.

In aspects, one or more of the methods in accordance with the present disclosure may include stimulating the stimulation location (e.g., a nerve, a tissue site, etc.) with one or more pulse trains, the pulse trains including one or more pulses with a predetermined spectral content (e.g., pulses centered around 10 Hz, 50 Hz, 100 Hz, 500 Hz, etc.) at one or more locations proximal and/or distal to the surgical site.

The pulse train may be applied locally to the stimulation location (e.g., nervous structure, tissue site, etc.), with an amplitude of generally 1.5× the voltage required to obtain a maximal amplitude compound action potential (CAP), with pulse duration of generally between 0.05 and 0.5 ms and interval of between 2 ms (for 500 Hz spacing) to 100 ms (for 10 Hz spacing). The pulse train may include one or several such pulses, perhaps even spaced with alternative timing over the application of the pulse (so as to better scan through a frequency range of interest). The corresponding nervous response may be monitored at another location on the vessel or in the body. Such response may be monitored with a gain of generally 500 to 5000 and generally over a frequency band of 0.1 Hz to 10 kHz. This configuration may be used to evaluate the overall health and/or capability of the nervous structure connecting the stimulating location and the monitoring location.

During a surgical procedure, early indication of functional alteration to the nerve structure may be determined by monitoring for a change in the properties of the sensed signal (e.g., a change in latency, amplitude, conduction velocity, spectral content, etc.). In aspects, an ablation pulse may be applied to the nerve between the stimulatory and monitoring locations. A change in the properties of the sensed signal (e.g., a decrease in high frequency content therefrom, a change in latency, change in amplitude, etc.) may be an early indicator that the pulse is being applied properly to the nervous structure there between. In addition, additional pulses may be applied and the response monitored in order to observe the nerve response through to a sufficient state of functional alteration, such as during an ablation procedure.

Monitoring may continue during a follow up period immediately after the surgical procedure, and/or during a longer term period (e.g., hours, days, weeks, etc.). Such follow up may be used to determine and/or prognosticate on the longevity of the surgical intervention. Such follow up may be performed with an implantable device in accordance with the present disclosure.

In aspects, one or more of the techniques disclosed herein may be used to identify the particular neurons of interest, or to ensure that the correct neurons are being treated surgically (as well as to ensure that the extent of the treatment is acceptable). Such identification may involve monitoring a level of neurological activity on the sensed nerve(s) to determine if the levels are outside of the norm (i.e., as compared with other sites in the body, an activity metric for the patient population or a subset thereof, etc.).

A method for generating a follow up schedule following a surgical procedure may involve monitoring the neurological activity of the site for a period of time (e.g., hours, days, weeks, etc.) after the surgical procedure; trending the neurological activity to create a metric relating to changes therein over the period of time; and predicting recurrence data (e.g., probability of recurrence, a timeframe of recurrence, etc.) therefrom; and generating a follow up schedule dependent upon the recurrence data.

A method for searching for a nerve of interest on the wall of a bladder may include applying a point pressure on the wall of the bladder while monitoring distal and/or proximal nervous activity (e.g., monitoring, and/or stimulation and sensing on either side of the point pressure probe, along an associated nerve plexus, along a sacral nerve, etc.). Changes in the observed signals may be indicative of pressure induced neural block and/or triggering of a sensory nerve due to the applied point pressure (i.e., thus identifying the location of the neural anatomy under investigation).

The method may include poking one or more regions of the organ wall (e.g., bladder wall) with a smooth protruding probe, to increase pressure at the interface between the probe and the tissues. The probe may be combined with an ablation electrode (thus providing colocation of the pressure application and the ablation zone). Multiple probes may be used together to deliver ablation along the length of a nerve or nerve bundle, over an extended region of the organ wall, etc. In aspects including multiple probes, one or more probes may be relatively placed onto the surface so as to optimize an ablation current passed there between.

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g., a probe, a microfinger, a sensory tip, an electrode element, a point pressure applicator, etc.) may provide pressure variation above and/or below these ranges during a procedure in order to assess nerve function, location, etc. as described herein.

In aspects, a point pressure applicator may be configured to operatively provide an oscillating pressure to the test site, to synchronize pulsatile pressure application with an array of probes, etc. so as to better orient a pair or array of probes for an ablation procedure.

In aspects, a hook-like tool in accordance with the present disclosure (e.g., with one or more sensing tips thereupon, configured as an electrode element, etc.) may be used to make consistent and controlled contact with the target anatomy (so as to access large surface of the anatomy with a simple tool). A soft hook-like structure with tissue interfaces (electrode arrays, sensing tips, etc.) fashioned towards the inner surface could be used to delicately contact the key anatomy during a surgical procedure. The hook may include a quick release (e.g., a mechanical quick release, an electroactive material quick release, etc.), or a biodegradable structures, etc. for simple removal from and/or positional correction along the anatomy (e.g., an organ wall, etc.) during, and/or at the conclusion of a surgical procedure.

A sensing tip in accordance with the present disclosure may be attached to the hook to enable sensing and/or interfacing with the adjacent tissues during an associated surgical procedure.

In aspects, a method for searching for a nerve of interest on the wall of a target organ may include applying a point pressure on the wall of the vessel while monitoring distal and/or proximal nervous activity (e.g., monitoring, and/or stimulation and sensing on either side of the point pressure probe). Changes in the observed signals may be indicative of pressure induced neural block due to the applied point pressure (i.e., thus identifying the location of the neural anatomy in question).

In aspects, the method may include clamping the vessel with a flat, smooth backing plate (e.g., a flat soft surface, etc.) and a protruding probe on the adjacent wall, to increase pressure at the interface between the probe and the tissues. The probe may be combined with an ablation electrode (thus providing colocation of the pressure application and the ablation zone). Multiple probes may be used together to deliver ablation along the length of a nerve or nerve bundle. In the case of multiple probes, the probes may be relatively placed onto the surface so as to optimize an ablation current passed there between.

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g., a sensing tip, a balloon face, an electrode element, a point pressure applicator, etc.) may provide pressure variation above and/or below these ranges in order to assess nerve function, location, etc. as described herein for the application of interest.

The point pressure applicator may be configured to operatively provide an oscillating pressure to the test site, to synchronize pulsatile pressure application with an array of probes, etc. so as to better orient a pair or array of probes for an ablation procedure.

In aspects, the biasing force between one or more surgical elements (e.g., a balloon, a microfinger, a point pressure applicator, etc.) and the adjacent tissues may be controlled by various means including feedback via bioimpedance measurements, interfacial pressure sensors, micro-pulse oximetry based measurements, through flow and/or local perfusion measurements, via optically equipped sensing tips, combinations thereof, and the like. It may be desirable to control the application of force for various reasons such as causing signal inhibition via mechanical compression (nerve compression); for imposing a temporary nerve block during an associated procedure; to mask the underlying nervous activity during surgical site selection; to control one or more contact pressures and/or impedance for performing an associated ablation and/or monitoring procedure.

In aspects, a surgical tool in accordance with the present disclosure may include a means for applying a vacuum at sites in and around the electrodes. Such vacuum attachment may allow for very intimate yet gentle contact between the adjacent tissue surface and the electrodes during a procedure.

In aspects, a soft flexible structure in accordance with the present disclosure may be used in conjunction with a surface enhancement and/or wicking function (a hydrophilic material, a porous material, etc.) so as to draw fluid out from the target tissue surface and use the resulting capillary forces and surface tension to form a tight, intimate contact between the tool and the tissue suitable for neurovascular monitoring. This may be an option for long term placement (e.g., placing of an implantable component during a procedure for follow up, etc.). Silk structures included into the flexible structure may be suitable for providing this functionality, optionally with a first layer that can dissolve quickly and a second layer that may dissolve over the course of hours, days, weeks, etc.

In aspects, the flexible structure may include a medicament (e.g., a neural blocking agent, an anesthetic, lidocaine, epinephrine, a steroid, a corticosteroid, an opioid, alcohol, phenol, etc.). In aspects, the flexible structure may include a medicament releasing structure (i.e., a hydrogel structure) into which the medicament is bound, and may be released into the surrounding tissues over the course of minutes, hours, days, weeks, etc. In aspects, the hydrogel may be formed from a radical based crosslinking chemistry, a click crosslinking chemistry, etc.

In aspects, a surgical tool in accordance with the present disclosure may be configured to deliver a bolus of medicament into the tissues of interest. In aspects, the bolus may be housed in a hydrogel prepolymer, the surgical tool including means for polymerizing the hydrogel prepolymer in place after release to form a slow release structure, from which the medicament may leach into the surrounding tissues over a prolonged period of time (i.e., hours, days, weeks, months, etc.). In aspects, the hydrogel may include biodegradable chains, configured so as to allow for breakdown of the hydrogel over time, after being placed within the body of a subject.

In aspects, the structure may include a thin degradable support structure. The support structure may be degradable so as to quickly dissolve in the presence of liquid (saline) such that it may be placed beside the organ wall and wetted, so as to cause the remaining structure to flop down, and/or otherwise contact the organ wall.

In aspects, the system may include one or more sensing tips (e.g., tonal measuring, optically equipped, electrodes, etc.) positioned to the interfacing side, i.e., the side that may interface with the adjacent anatomy.

Such soft configurations may be useful to establish a reliable, yet gentle contact to a vessel surface, intimately contouring to the surface of the vessel without applying excessive pressure thereto. Intimate yet soft contact may be advantageous for reading sensitive neurological signals without interfering mechanically with signal transmission thereof.

A surgical tool in accordance with the present disclosure may include one or more whiskers extending from a tool surface so as to reliably contact an adjacent tissue structure during a surgical procedure. The whiskers may include sensing tips such as electrodes, and the like. Additionally, alternatively, or in combination, a sensing tip in accordance with the present disclosure may include a whisker for interfacing with the adjacent tissues during a procedure.

In aspects, whisker penetration into an adjacent nerve bundle may be used to achieve more intimate contact thereto, as well as to better isolate electrodes from other macroscopic signal interference, etc.

In aspects, whiskers may be formed from microfibers, nanofibers, microneedles, nanoneedles, etc. In one aspect, one or more whiskers may be formed from a carbon structure, e.g., a carbon fiber, a carbon nanotube, etc. In aspects, the whiskers may be insulated along a portion of their length, with an electrically exposed region at the tip there upon.

In aspects, one or more of the whiskers may be substantially hollow, configured so as to store a medicament in accordance with the present disclosure, to provide a means for delivery of a medicament in accordance with the present disclosure, or the like.

In aspects, a boundary method for monitoring a surgical site during a surgical procedure may be employed. During this approach a plurality of sensor tips may be arranged in contact around a perimeter of a surgical region on a tissue surface, whereby the electrophysiological signals measured at locations along the surface may be used to determine the state of the tissues within the boundary. For purposes of discussion, the boundary may be effectively the distal and proximal ends of the vessel or the ends of the surgical area, when applied to a tubular organ of interest.

In aspects, a visual detection approach may be used in combination with, or in addition to any of the endoscopic approaches in accordance with the present disclosure. In aspects, visual assessment may be used to at least partially guide the surgical procedure. The feedback may be in the form of a visible, a near infrared, infrared spectroscopic, or similar camera system, used in conjunction with the surgical tools, so as to better visualize the vessel structure, identification of target anatomy (e.g., a nerve, nerve bundle, etc.) on the target organ (e.g., a bladder, a uterus, etc.), perhaps placement of tools onto the target anatomy, etc.

In aspects, a backlit vessel lighting system may be used to assist with visualizing the anatomy, locating target anatomy, etc.

In aspects, a system in accordance with the present disclosure may include a feature enhancing medium, to highlight targeted tissue species (e.g., highlight nerve tissues, etc.). The medium may include molecular binding species to selectively bind with surface receptors on the intended target tissue, perhaps changing one or more visual (chromatic) properties in the process and/or including a visual marking moiety. Some non-limiting examples of suitable molecular binding species are peptides and aptamers. Suitable peptides and aptamers may be selected for target tissue (e.g., nerve tissue, fat, etc.) and may be selected as known in the art.

Inclusion of molecular binding species that have been selected for the target cells may be advantageous to assist with anatomical visualization during a surgical procedure. The molecular binding species may be provided suspended in a delivery vehicle, such that it may be conveniently delivered to the target tissues during a procedure. The delivery vehicle may be a gel material, a 1 part curing gel, elastomer, etc. that may be conveniently delivered to the target tissues. A fully curable vehicle may be advantageous for providing a simplified method for completely removing the medium from the body after the surgical procedure and/or targeting process has been completed.

Molecular binding species may include a visual marking moiety that is configured to improve visibility thereof. Thus the molecular binding species may bind to the target tissue sites (e.g., nerve tissue, etc.), and may be highlighted by the visual marking moiety for visualization with an appropriate visualization system. Some non-limiting examples of visual marking moieties include: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

This visualization approach may be advantageous to identify the key tissues for surgical procedures (such as renal sympathectomy). By providing the material in a form suitable for surgical delivery and complete removal post operatively, the resulting system may be safer compared to approaches that require systemic application of the material.

A system in accordance with the present disclosure may include an implantable tool, configured to be left in the body following the surgical procedure for purposes of follow up.

In aspects, the implantable tool may include one or more sensing tips (i.e., MMG sensors, electrodes, etc.) to interface with the adjacent tissues.

In aspects, the implantable tool may include a draw cord, configured to mechanically connect the tool to the exterior of the body. Upon completion of the monitoring period, the draw cord may be used to withdraw the implantable tool from the body. Thus the implantable tool may provide follow up monitoring for days, weeks, to months after surgery, but may still be removed from the patient in an out-patient setting.

The implantable tool may include communication circuitry to communicate monitored signals or signals created therefrom to a monitor outside of the body. Such a system may be used to monitor nerve function (e.g., electrophysiological signals, nerve activity, EMG, etc.) to determine if the undesirable signal or neurological behavior is returning or not after the surgical procedure. Thus the implantable tool may provide follow up monitoring for days, weeks, to months after surgery, but can still be removed from the patient in an out-patient setting.

The implantable tool may be used to monitor the site after surgery, to determine if the functional changes will last indefinitely, for a short period of time, etc. Such a tool may be useful for scheduling follow up, prognosticating on patient outcomes, etc.

In aspects, the surgical system may include other functionality including: angiographic die delivery, saline delivery, temperature monitoring, intra and extra corporeal coordination between devices, through wall imaging, through wall current flow, saline provision for local tissue cooling, radiopaque markers for identification by associated imaging systems, optical coherence tomographic (OCT) capabilities, and the like.

In aspects, a system in accordance with the present disclosure may be configured to map various electrophysiological aspects of an organ wall. In aspects, the system may be configured to identify abnormal nerve activity, thus providing a means for selective sympathectomy of nerves (sensory nerves, afferent nerves, efferent nerves, etc.) in the bladder to treat a disease state (e.g., to treat overactive bladder).

The system may include one or more means for monitoring neurological feedback, locally and/or distant to the surgical site, for feedback of adequate denervation in accordance with the present disclosure.

In aspects, the system may include means for monitoring urge (i.e., a sensation of a need to urinate) based feedback, monitoring signal activity as a function of bladder fullness, and the like before, during, and/or after an associated procedure. Such monitoring may be influenced by one or more features of the system (e.g., as controlled by fluid exchange with the bladder during a procedure, as controlled by inflation of a balloon in the bladder during a procedure, etc.).

In aspects, the system may include means for capturing and/or monitoring patient feedback relating to sensation, pain, fullness, etc. before, during, and/or after a surgical procedure and/or associated urge based feedback study (e.g., a urodynamic study, a balloon inflation procedure, etc.). Such means may include video monitoring of a subject during a procedure, monitoring one or more nerves, sacral nerves, EMG of muscles in the vicinity of the bladder (i.e., detrusor muscle contraction, spasm, etc.), audibly requesting feedback from the subject, combinations thereof, or the like during a procedure. Such feedback may be used as a surrogate or as supplemental evidence for determining the completeness/effectiveness of an associated procedure.

In aspects, a method in accordance with the present disclosure may be used to test for and/or diagnose a disease state in a subject (e.g., diagnose overactive bladder). The method includes placement of a portion of a system, a device, and/or a surgical tool in accordance with the present disclosure into the bladder of a subject, biasing one or more aspects of the device against the wall of the bladder, obtaining feedback from the aspect of the device (e.g., sensing tip, microfinger, probe, etc.) to assess local nervous activity in accordance with the present disclosure, optionally changing the bias and monitoring one or more aspects of the neurological response thereto so as to establish the relationship there between, and comparing the feedback and/or response to a population statistic (e.g., average response, median response), and/or population based model so as to determine if the behavior is normal. Such information may directly give information pertaining to the diagnosis of the disease state. Furthermore, the system may include aspects to treat the disease state directly after diagnosis during the same interventional procedure in accordance with the present disclosure.

Additionally, alternatively, or in combination, the system may include one or more aspects in accordance with the present disclosure to detect a tumor and/or lesion along an organ wall (e.g., along a bladder wall), excising and/or ablating a suspected tumor and/or lesion in accordance with the present disclosure. Such means may include tone monitoring aspects, visual feedback from an associated camera system, altered electrophysiological activity thereby, etc.

A system in accordance with the present disclosure may include a delivery system (e.g., a minimally invasive catheter, a tubular delivery system, etc.), configured for entry into a hollow organ (e.g., a bladder, uterus, etc.), via a port (e.g., a urethra, a vagina, etc.). The catheter may include and/or interface with one or more sensing tips, probes, and/or microfingers in accordance with the present disclosure.

The delivery system may include a delivery catheter with a diameter less than 10 mm, less than 6 mm, less than 4 mm, less than 2 mm, so as to fit through a port and interface with an associated organ.

In aspects, the delivery system may include one or more features configured to retain, register, and/or otherwise keep the delivery system in place within the body during a surgical procedure. Some non-limiting examples of such features include one or more anchors, a Malecot wing tip, J-stent, basket feature, DePezzer mushroom tip, a Foley balloon, registration markings, tolerance lines, contrast markings, embossed indicators, combinations thereof, and the like.

In aspects, the delivery system may include one or more balloons, configured to register and anchor the delivery system at the urethral entrance to an associated bladder during a surgical procedure.

In aspects, the delivery system may include one or more microfingers, balloons, meshes, combinations thereof, or the like each in accordance with the present disclosure.

In aspects, a system in accordance with the present disclosure may include a single or multi-lumen sheath with a balloon attached towards a distal end thereof (e.g., towards an end that is inserted into a body). The balloon may have a plurality of electrical elements and/or sensing tips in accordance with the present disclosure arranged around the outer surface thereof. In aspects, the balloon may be expandable so as to bias the electrical elements embedded thereupon against the bladder wall, and/or to effectively fill the bladder during the procedure.

In aspects, one or more electrical elements included in the tool, balloon, etc. may be interconnected with a control unit, so as to provide a combination of feedback (e.g., biosignal sensing, stiffness sensing, etc.) and/or actuation (e.g., ablation, movement, etc.) capabilities, or the like.

In aspects, a system for monitoring, electrophysiologically mapping, and/or electrically pacing an organ (i.e., a bladder) in accordance with the present disclosure includes one or more sensing tips in accordance with the present disclosure for interfacing with the organ walls, and/or an entry port (i.e., a urethra) before, during, and/or after a procedure. In aspects, such sensing tips may include microsensor electrodes, electrode strips, mechanomyographic sensors, stiffness sensors, impedance sensors, combinations thereof, or the like each in accordance with the present disclosure.

In aspects, one or more sensing tips/electrodes may be configured for delivering a stimulation and/or a therapy (e.g., RF ablation, microwave ablation, etc.), to one or more tissue sites within the organ, and/or entry port. In aspects, arrangements may be suitable for performing local ablations, strip ablations, ablating odd shaped regions of the organ wall, ablating arbitrarily programmable regions of the organ wall (i.e., as determined necessary via feedback monitoring thereof, via a test procedure, etc.). Such ablation may be scoped, and/or completed based upon and/or with feedback from sensors In aspects, before, during, and/or after an ablation procedure, a local flow of fluid may be provided so as to minimize damage, char, etc. that may form during the procedure.

In aspects, a system in accordance with the present disclosure may include a counter electrode configured and dimensioned for placement within the entry port, the organ, in the vicinity of the organ, in an adjacent organ (i.e., a vaginally, or rectally placed counter electrode, etc.). In aspects, the counter electrode may be configured as a reference electrode for monitoring electrophysiological activity as part of a procedure in accordance with the present disclosure, as a counter electrode for use in facilitating an RF ablation procedure, combinations thereof, or the like.

In aspects, one or more RF ablation currents may be directed between two or more electrodes included in a system in accordance with the present disclosure. Thus a local, programmable current patch may be configured between electrodes in communication with a local tissue site in the body. The electrodes selected for current flow may be selected based on feedback, determination of abnormal electrophysiological activity (i.e., at one or more sites along a target organ, etc.). Such a configuration may be advantageous to limit delivery of therapeutic currents to a region of diseased tissue, a target treatment site, etc.

In aspects, additional electrodes may be placed at remote sites within or on the body to facilitate additional monitoring pathways, or therapeutic current flow pathways during a procedure.

A method for scanning one or more anatomical sites within a body for overactive and/or irregular tissue behavior (i.e., abnormal physiological and/or electrophysiological activity) in accordance with the present disclosure may include biasing one or more electrode elements towards the wall of an organ (i.e., a bladder, a uterus, etc.) and assessing the electrophysiological activity thereof. In aspects, the method may include determining if the electrophysiological activity is abnormal (i.e., overactive, erratic, overly sensitive to stimuli, etc.). In aspects, the method may include deciding upon whether to mark (i.e., mark with an identifying feature for future reference, etc.), treat (i.e., to treat the tissues with a method in accordance with the present disclosure), to treat immediately with the electrodes used in the assessment, etc. In aspects, the method may include treating the tissue without removing the surgical tool from the body of the subject between procedures (i.e., between assessing, testing, and treating one or more sites within the body).

In aspects, the method may include monitoring physiological response at one or more remote locations in the body (physically removed from the organ) in conjunction with a stimulation or test. In aspects, the method may include stimulating one or more tissues to determine the location of proprioceptive nerve endings for potential treatment.

In aspects, one or more abnormal sites (i.e., as determined by an assessment, etc.) may be selectively treated so as to augment (i.e., adjust) the overall behavior of the bladder during regular filling and voiding procedures.

In aspects, the method may include mapping one or more sites using a system in accordance with the present disclosure. In aspects, the mapping results may be may be used to selectively ablate and/or denervate regions of the bladder wall, selectively reduce neurological interconnection to one or more regions of the bladder, etc.

In aspects, the method may include assessing pain, bladder related pain, etc. with a system in accordance with the present disclosure. The method may include stimulating one or more sites within the organ or along a neurological feature connected thereto while assessing a subject response thereto. In aspects, the method may include questioning what a subject is feeling during a stimulation event, evaluating the degree of sensation being felt by the subject, etc.

The method may include monitoring physiological and/or electrophysiological signals at one or more sites within the organ (i.e., bladder, along a wall of the bladder, etc.) or one or more neurological features connected thereto, while performing a urodynamic procedure (i.e., filling the bladder with a fluid, voiding the bladder, having the subject attempt to urinate, etc.).

In aspects, a system in accordance with the present disclosure may be used to diagnose the proprioceptive sites for pain registration in the bladder. Such testing may be performed via actively stimulating sites along the bladder wall, while monitoring patient feedback, discomfort, pain levels, etc. Such testing may provide a means for locating abnormal tissue sites, potentially responsible for generating the pain signals. Treatment of such sites may be performed in combination with testing. In aspects, a method related thereto may include generating a metric based upon the extent of electrophysiological activity experienced during a urodynamic procedure, and at least partially assigning the diagnosis based upon the metric.

In aspects, treatment of one or more sites within the organ or on a neurological feature connected thereto may be performed in single steps or staged (i.e., performed over a sequence of steps). In aspects, a staged treatment may include applying a bolus of energy to treat one or more sites (i.e., a first bolus with a reversible energy level, a low energy level, etc.), so as to determine if the correct site is being treated. In order to assess the site, the energy bolus may be applied locally to a level sufficient to temporarily disrupt function of the local tissues, but not provided in a sufficient amount to cause irreversible damage thereto. In aspects, upon confirmation of a desirable change in function after application of the first bolus of energy, a second bolus of energy, suitable for implementing an irreversible treatment may be applied (e.g., a high energy ablation as opposed to a low energy ablation).

In aspects, staged treatment may also take place over a plurality of spatially separated regions of the bladder. In aspects, the treatment may be applied strategically to regions of the bladder, perhaps those regions that respond most dramatically to the testing regiment, or those regions that are most active. The treatment may continue along the wall of the bladder until a suitable change in activity has been observed.

In aspects, a system in accordance with the present disclosure may include pressure sensitive elements, stretch elements, etc. In aspects, the combination of signals derived from such elements in combination with a filling procedure (i.e., a urodynamic procedure), the results of which may be suitable for determining tone of the bladder wall, changes in tone with filling, local differences in tone (i.e., as may be caused by a local lesion or tumor), etc.

In aspects, a method and/or a system in accordance with the present disclosure may be used to treat a patient suffering from overactive bladder.

FIGS. 1a-b show aspects of a surgical tool 100 placed within a urinary bladder 2 in accordance with the present disclosure. FIG. 1a shows aspects of a surgical tool 100 placed into a bladder 2 of a subject via the urethra 1 of the subject. In the example shown, the subject is female and shown for reference is the vagina 3, the uterus 4, and the rectum 5. The surgical tool 100 (i.e., a monitoring tool, a treatment device, etc. in accordance with the present disclosure) includes a delivery system 110 in accordance with the present disclosure configured and dimensioned so as to traverse through the urethra 1 into the bladder 2 during an insertion procedure. The surgical tool 100 includes a balloon 105 fastened thereto. The balloon 105 includes one or more sensing tips each in accordance with the present disclosure, configured so as to bias towards a wall of the organ upon expansion of the balloon there within. The surgical tool 100 includes a port 115 configured to provide fluid exchange between a distal and proximal end thereof (i.e., in the example shown, so as to fill the balloon 105 during an inflation procedure, or deflate the balloon 105 during a deflation procedure).

The surgical tool 100 may be coupled in mechanical, fluid, and/or electrical communication 120 with a controller (not explicitly shown) for performing one or more aspects of the procedure. In aspects, the surgical tool 100, in this case, the delivery system 110 may include one or more sensors in accordance with the present disclosure. As shown in FIG. 1a, the delivery system 110 may include an electrode 125 (i.e., a counter electrode, a reference electrode, etc.) positioned along the length thereof and electrically coupled with the controller. In aspects, the electrode 125 may be positioned along the delivery system 110 so as to interface intimately with a sphincter (i.e., a urethral sphincter, etc.) after placement for a surgical procedure. The electrode 125 may be configured to stimulate and/or monitor electromyographic activity in local tissues during a procedure (i.e., during a urodynamic test, a stimulation process, an ablation process, etc.). In aspects, the electrode 125 may be configured as a counter or reference electrode for use in conjunction with one or more sensing tips situated on the balloon 105. In aspects, the surgical tool 100 may be configured so as to pass an RF current from one or more sensing tips situated on the balloon 105 to the electrode 125. In aspects, the surgical tool 100 may be configured so as to monitor electrophysiological activity at one or more sensing tips on the balloon 105 with reference to the electrode 125.

FIG. 1b illustrates the surgical tool 100 placed within the bladder 2 of a subject, engaged 120 in fluid, and electrical communication with a controller (not explicitly shown). A bolus of fluid was delivered to the surgical tool 100 and filled the balloon 105' via the delivery system 110 and the port 115 so as to engage the balloon 105' with the wall of the bladder 2. In aspects, the balloon 105' may have been filled so as to provide a pressure P against the walls of the bladder 2. In aspects, the pressure P may be less than 50 mmHg, less than 30 mmHg, less than 10 mmHg, less than 5 mmHg, or the like. In aspects, the balloon 105' may include one or more sensing tips in accordance with the present disclosure to measure the applied pressure P. In aspects, the balloon 105' may include one or more sensing tips in accordance with the present disclosure to monitor one or more physiological and/or electrophysiological signals along the walls of the bladder 2. In aspects, such monitoring may be to elucidate one or more regions 130a-i along the bladder wall 2 with abnormal physiological behavior (i.e., abnormal electrophysiological activity, abnormal sensory response to an applied pressure P, etc.). Such regions 130a-i may be designated as sites for treatment. In aspects, the surgical tool 100 may be configured to treat one or more of the regions 130a-i via one or more sensing tips included in the balloon 105'. In aspects, the treatment of the regions 130a-i may be performed via one or more electrodes included in the balloon 105'. In aspects, the surgical tool 100 may be configured so as to pass an RF current from one or more sensing tips situated on the balloon 105' to the electrode 125. In aspects, the surgical tool 100 may be configured so as to monitor electrophysiological activity at one or more sensing tips on the balloon 105' with reference to the electrode 125.

In aspects, a sensing tip in accordance with the present disclosure including one or more piezoresistive materials may be configured to measure a local contact pressure between the balloon and the wall of the organ. Such measurements may be performed in conjunction with the monitoring so as to relate local stresses (i.e., embodied in local tissue strains, etc.) with electrophysiological activity in the related tissues. Such relationships may be used in the formation of a metric for diagnosing a disease state, determining if a tissue site is a candidate for therapy, determining if a therapy has been successful, etc.

FIG. 2 shows aspects of a surgical tool 200 in accordance with the present disclosure. The surgical tool 200 includes a delivery system 210 in the shape of an elongate structure (i.e., in this case a tubular structure) including one or more lumens 235 therein suitable for placement of the surgical tool 200 within a cavity of a subject, for communicating mechanically, electrically, or for delivering fluid 222 between a proximal and distal end thereof as part of a procedure in accordance with the present disclosure. In aspects, the surgical tool 200 may include a maneuverable tip (also 210), which may be oriented within the organ once placed therein. The delivery system 210 may include one or more ports 215 for fluid delivery there between. The delivery system 210 includes cabling 240 (i.e., wires, a printed circuit traces, etc.) for providing the electrical communication 222 between the controller and one or more sensing tips or electrodes 225 located on the surgical tool 200.

FIG. 2 illustrates a balloon 205, 205' in accordance with the present disclosure (i.e., equivalently a deployable mesh-like structure), the balloon 205, 205' including one or more sensing tips 245 each in accordance with the present disclosure, suitable for interfacing with tissues adjacent thereto during a procedure. The balloon 205, 205' is shown in a delivery state 205 (i.e., a state suitable for passage through an entry port to the organ), and an expanded state 205' (i.e., a state suitable for interfacing with tissues in the organ). In the example shown, the balloon 205 is pleated 250 around the shaft of the delivery system 210 in the delivery state.

In aspects, the balloon 205, 205' may include a plurality of sensing tips 245 configured over the surface thereof. In aspects, the sensing tips 245 may be configured to monitor highly local anatomical sites (i.e., via one or more micro-electrode aspects), or to monitor a macroscopic region of the organ wall (i.e., via one or more macroscopically oriented electrode aspects). FIG. 2 illustrates a series of sensing tips 245 arranged along the balloon 205' to measure electro-physiological activity over a region 265 of the surface thereof.

In aspects, a series of microelectrode sensing tips may be configured and arranged so as to monitor local activities (i.e., designated by individual + and – symbols in the figure), or so as to collectively monitor activity representative of the entire region 265 (i.e., via a summation process, etc.). Such a configuration may be advantageous for determining if a region along an organ wall needs further treatment, etc. In aspects, the sensing tips 245 may be used to provide treatment to such regions 265, or microscopic sites within. Such treatment may be programmably configured based upon an earlier sensing operation, or the like.

In aspects, a series of sensing tips 245 in accordance with the present disclosure may be arranged and configured along the balloon 205' to measure local tissue compliance 255 within a region 260 of an organ adjacent thereto (i.e., during a filling procedure, a urodynamic test, etc.).

FIG. 3 shows aspects of a balloon wall 305 in accordance with the present disclosure. The balloon wall 305 includes one or more sensing tips in accordance with the present disclosure. The balloon wall 305 includes a plurality of electrodes 330 in accordance with the present disclosure. The electrodes 330 are arranged in a cluster 315 along the balloon wall 305 arranged on the outer face thereof so as to interface with adjacent tissues when the balloon 305 is biased there against (i.e., during a surgical procedure, etc.). The electrodes 330 are electrically interconnected with one or more aspects of an associated surgical system (i.e., interconnected with a delivery system, a microcircuit, a connector, a controller, etc.) via one or more electrical traces 325. In aspects the electrical traces 325 may be stretchable, isolated from the surrounding media (i.e., via an overcoat, etc.), or the like.

The balloon 305 has a wall thickness 320. In aspects the wall thickness 320 may be less than 200 um thick, less than 100 um thick, less than 50 um thick, less than 30 um thick, less than 20 um, less than 10 um, less than 4 um, less than 1 um, etc. In aspects the balloon wall 305 may include a stretchable, substantially elastic material so as to accommodate expansion during a deployment procedure. In aspects, the balloon wall 305 may include one or more composites of somewhat stiffer materials (such as polyimide, PET, PEN, etc.) and somewhat softer materials (e.g., silicones, polyurethanes, thermoplastic elastomers, etc.) to compromise between overall structural stiffness and conformal capabilities of the wall, or to allow for asymmetric expansion thereof during a deployment procedure.

In aspects, the balloon wall 305 may include an interfacial pressure sensing tip 340 configured to monitor a pressure 350 applied thereto in accordance with the present disclosure. The pressure sensing tip 340 may be coupled with one or more aspects in the system via one or more interconnects 345. In aspects, the pressure sensing tip 340 may include a piezoresistive material, a strain sensitive material, a nano-material based material (i.e., a whisker based material in accordance with the present disclosure), etc.

In aspects, the balloon wall 305 may include an optical sensing tip 360 in accordance with the present disclosure. In aspects, optical sensing tip 360 may be equipped with a corresponding micro-light source (e.g., an oLED, an LED, etc.). The micro-light source may be used to direct light 370 into the adjacent tissues. One or more optical sensing tips 360 may be equipped with optical microsensors configured to detect light 375 emitted from the micro-light source as back scattered by and/or transmitted through the adjacent tissues. Such information may be used to detect anatomical features (e.g., nerves, tumors, etc.) in the adjacent tissues, monitor local fluids (i.e., water content, blood flow, etc.), interact with tissue visualizing materials, for inspecting tissues within the organ wall, etc. In aspects the optical sensing tip 360 may be interconnected with another aspect of the system via one or more electrical traces 365 in accordance with the present disclosure.

In aspects, one or more sensing tips 330, 340, 360 may include a microcircuit in accordance with the present disclosure. The microcircuit may be configured to manage signal acquisition, communicate with aspects of the system, etc.

FIGS. 4a-d show aspects of substrates 405, 425, 450, 470 or equivalently aspects of a balloon wall in accordance with the present disclosure. FIG. 4a shows a substrate 405 with an arrangement of electrodes 415a-c, 420a-f and electrical traces 417 attached thereto, configured to electrically interconnect 430 the electrodes with one or more aspects of a system in accordance with the present disclosure. The substrate 405 is shown with an arrangement of point sized electrodes 420a-f configured and dimensioned to interface (i.e., monitor local fields and/or delivery current thereto, etc.) with adjacent tissues over a relatively small distance. The substrate 405 also includes multiple elongate electrodes 415a-c configured and dimensioned to interface with adjacent tissues over a relatively large distance.

FIG. 4b illustrates aspects of a substrate 425 with attached electrical traces 430 in accordance with the present disclosure. The electrical traces 430 are coated in regions by an insulating layer 435, and may be exposed in regions 440 to form electrodes for interfacing with adjacent tissues. The exposed regions 440 may be coated with one or more additional electrode materials to improve the interface with adjacent tissues, store one or more medications, etc.

FIG. 4c shows aspects of a substrate 450 with attached electrical traces 455 in accordance with the present disclosure. The electrical traces 455 are coupled with a sensing tip 465 in accordance with the present disclosure. In aspects, the electrical traces 455 and/or regions of the substrate may be covered with an insulating layer 460 to isolate them from the adjacent environment, etc.

FIG. 4d shows aspects of a substrate 470 including an electrode with a plurality of whiskers 495 in accordance with the present disclosure. The substrate 470 may include one or more whisker-like structures 495 extending from an electrode element 490 included or exposed on the surface of the substrate 470 (i.e., collectively forming a sensing tip in accordance with the present disclosure). The electrode element 490 may be electrically interconnected 480 with a circuit element elsewhere in the tool, perhaps a local micro-circuit, etc. Such electrical interconnects 475 may be provided by a flexible circuit, wiring, cabling, etc. The substrate 470 may be configured such that one or more of the electrical interconnects 475 may be situated substantially at the neutral axis of the tool (i.e., so as to minimize stress thereupon during bending of the substrate 470). The tool may include insulating regions 485 configured for similar purposes, and/or as ways to define the extent of the electrode element 490 on the substrate 470 surface.

In aspects, one or more of the whiskers 495 may be formed from microfibers, nanofibers, microneedles, nanoneedles, etc. In aspects, one or more whiskers 495 may be formed from a carbon structure, e.g., a carbon fiber, a carbon nanotube, etc. In aspects, the whiskers 495 may be insulated along a portion of their length, with an electrically exposed region at the tip there upon.

The whiskers 495 may be configured with sufficient strength so as to penetrate into a tissue structure when biased there against. The whiskers 495 may be configured such that the tips may penetrate into an adjacent nerve structure, a nerve bundle, a nerve cell body (often called the soma), a dendrite, an axon, a cable-like bundle of neural axons, the endoneurium, a fascicle, an epineurium, and/or a perineurium during a procedure. Such a configuration may be advantageous for monitoring a neuronal signal from a more highly selective tissue site, than would be achievable with an associated macroscopic electrode.

FIGS. 5a-b show aspects of a surgical tool with flexible wire elements in accordance with the present disclosure. FIG. 5a shows a surgical tool including a delivery sheath 510 and a delivery member 505 (i.e., collectively a delivery system in accordance with the present disclosure). The delivery sheath 510 may be retractable 530 so as to expose more or less of the delivery member 505 during a deployment procedure. The delivery member 505 may be coupled with one or more microfingers 515 each in accordance with the present disclosure. The microfingers 515 may include one or more sensing tips 520 each in accordance with the present disclosure. In aspects, the delivery member 505 may be coupled with a cap 525 arranged so as to protect one or more sensing tips 520 during an insertion procedure. In aspects, the cap 525 may be slide ably 535 mounted on the delivery member 505 so as to allow for deployment of one or more microfingers 515 into the organ during a deployment procedure.

FIG. 5b illustrates aspects of the surgical tool with the cap 525' adjusted 540 along the length of the delivery member 505' so as to expose the sensing tips 520' and allow for deployment of the microfingers 515' so as to interface one or more of the sensing tips 520' with an adjacent organ wall 2. In aspects, the delivery member 505' may include a port 550 for communicating fluids between the organ 2 interior and a controller (not explicitly shown). Such fluid exchange may be suitable for adjusting the internal volume of the organ, removing fluids from the organ, providing coolant to the organ interior, etc.

In aspects, the delivery member 505' may be actuate able, and/or adjustable about an axis of the delivery sheath 510' so as to rotate 545, and/or sweep one or more of the sensing tips 520' along the organ wall 2.

FIG. 6 shows aspects of a surgical tool with a deployable substrate 645 in accordance with the present disclosure. The surgical tool includes a delivery sheath 615 and a delivery member 610 (collectively forming a delivery system in accordance with the present disclosure) arranged down a lumen within the delivery sheath 615. The delivery member may include a port 635 for fluid exchange between distal and proximal ends thereof. The tool may include a substrate 645 generally wrapped around the delivery member 610 so as to form a structure with a sufficiently small diameter to enter the organ through a port (i.e., a urethra). In aspects, the delivery sheath 615 may be retractable along the length of the delivery member 610 so as to deploy the substrate 645 within the organ so as to bias 650 the substrate 645 against a wall thereof. The substrate may include one or more electrical and/or optical traces 620, 630 for communicating 625 between one or more aspects of the tool and a controller, connector, etc. In aspects, the substrate 645 may include one or more sensing tips 640 (in this aspect shown as electrodes), and optionally one or more microcircuits 655 in accordance with the present disclosure coupled with the sensing tips 640 and the traces 620, 630.

In aspects, the microcircuit 655 may be configured so as to substantially reduce the number of signal wires that must be sent to the surgical site during the procedure. A networked array of sensing tips may be multiplexed together with a locally placed microcircuit 655 (e.g., an application specific integrated circuit, distributed/interconnected circuit elements, a collection of flexible semiconducting circuit elements, etc.). The microcircuit 655 may be configured to communicate such signals with an extracorporeal system (e.g., a computer, a control system, an RF ablation controller, a data acquisition system, etc.). The microcircuit 655 may be configured to communicate with the extracorporeal system via analog and/or digital means and/or methods. In aspects, the communication may be of primarily digital means such that the microcircuit may exchange data pertaining to any sensing tip in the array, as well as switch data, control data, RF pulse routing, etc.

FIG. 7a-d show aspects of a surgical tool with deployable mesh 710 in accordance with the present disclosure. The mesh 710 may include one or more fibers 715, 720 (i.e., fulfilling the function of microfingers in accordance with the present disclosure). The fibers 715, 720 may be configured to carry an electrical current and be coupled 730 with a controller, microcircuit, connector, etc. in accordance with the present disclosure. The fibers 715, 720 may be addressable such that fibers 715 arranged in a longitudinal direction a-e may be addressed independently of fibers 720 arranged in a cross direction. Thus interconnection for purposes of monitoring and/or applying currents to a site in the body may be programmatically adjusted during use (i.e., so as to direct a stimulating and/or ablation current to a site on the mesh 710, to monitor at one or more sites on the mesh 710, etc.). In aspects the mesh 710 may be configured so as to deploy 735 outwards from a delivery sheath when deployed into an organ of interest. In aspects the mesh 710 may include one or more sites 725 wherein sensing, current delivery, etc. may be programmatically adjusted during use.

Figure 7A:
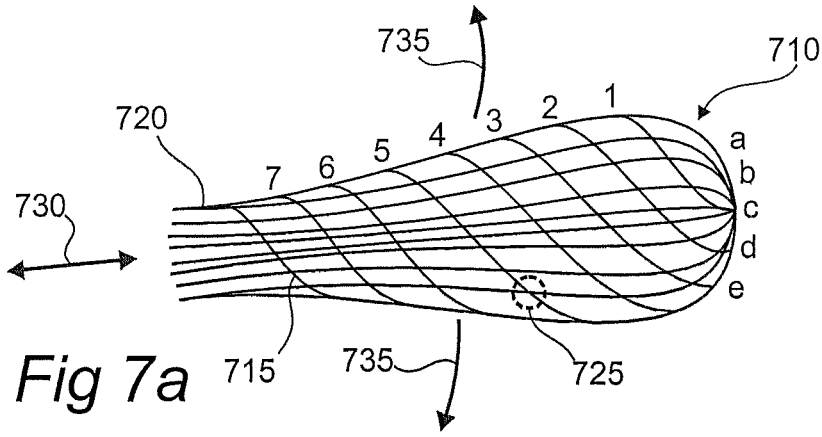
FIG. 7a-d show aspects of a surgical tool with deployable mesh in accordance with the present disclosure.
Figure 7B:
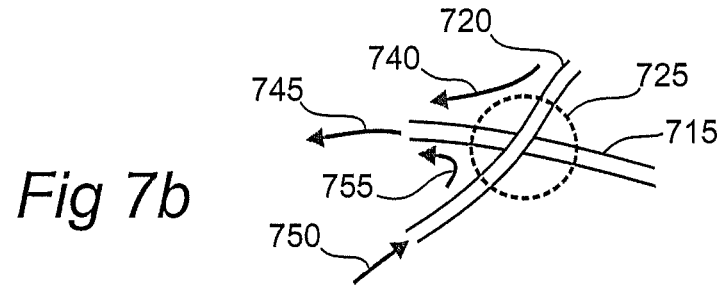

FIG. 7*b* shows aspects of a site 725 whereby multiple fibers 715, 720 in a mesh 710 come nearest together in an application. The fibers may include one or more exposed regions so as to allow for electrical communication of currents 740, 745, 750, 755 there between during use.

Figure 7C:

FIG. 7*c* illustrates a surgical tool 760 in accordance with the present disclosure including one or more fibers 770 and restrained within a delivery sheath 765. The fibers 770 may be provided in electrical and/or mechanical communication 775 with a controller, connector, and/or microcircuit in accordance with the present disclosure.

Figure 7D:
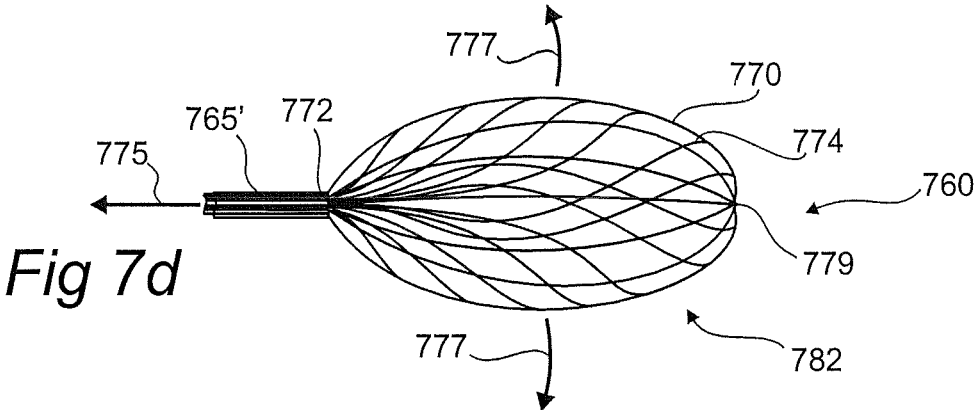

FIG. 7*d* shows the surgical tool 760 after the deployment of a mesh 782 from within a retractable delivery sheath 765'. The mesh 782 includes a plurality of fibers 770, 774 for interacting with the surrounding tissues of an organ. The mesh 782 may be configured so as to expand 777 outwards upon deployment from the delivery sheath 765'. In aspects, the mesh 782 may include one or more shape control points 772, 779 configured so as to help restrain the shape of the mesh 782 during a deployment procedure in a body.

The fibers 770, 774 may be provided in electrical and/or mechanical communication 775 with a controller, connector, and/or microcircuit in accordance with the present disclosure.

Figure 8:
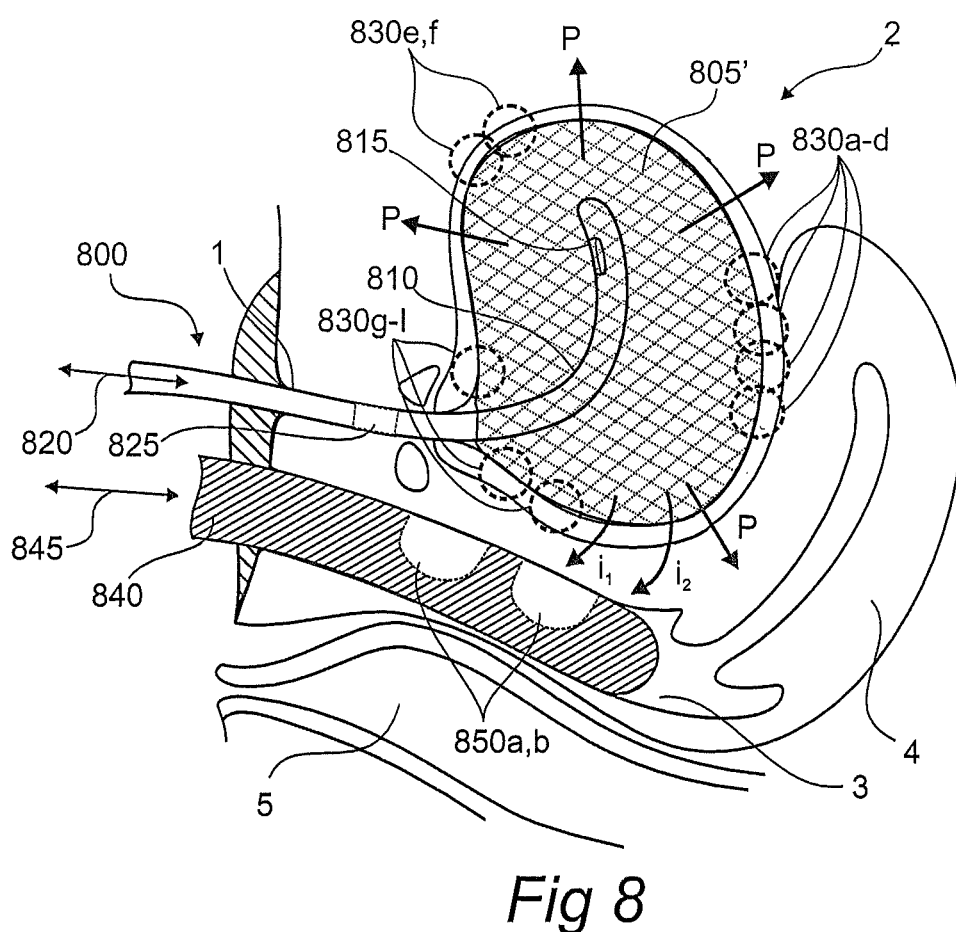
FIG. 8 shows aspects of a surgical tool with a counter electrode in accordance with the present disclosure.

FIG. 8 shows aspects of a surgical tool 800 with a counter electrode 840 in accordance with the present disclosure. The surgical tool 800 (i.e., a monitoring tool, a treatment device, etc. in accordance with the present disclosure) includes a delivery system 810 in accordance with the present disclosure configured and dimensioned so as to traverse through the urethra 1 into the bladder 2 during an insertion procedure. The surgical tool 100 includes a balloon 805' fastened thereto. The balloon 805' includes one or more sensing tips each in accordance with the present disclosure, configured so as to bias towards a wall of the organ upon expansion of the balloon 805' there within. The surgical tool 800 includes a port 815 configured to provide fluid exchange between a distal and proximal end thereof (i.e., in the example shown, so as to fill the balloon 805' during an inflation procedure, or deflate the balloon 805' during a deflation procedure).

FIG. 8 illustrates the surgical tool 800 placed within the bladder 2 of a subject, engaged 820 in fluid, and electrical communication with a controller (not explicitly shown). A bolus of fluid was delivered to the surgical tool 800 and filled the balloon 805' via the delivery system 810 and the port 815 so as to engage the balloon 805' with the wall of the bladder 2. In aspects, the balloon 805' may have been filled so as to provide a pressure P against the walls of the bladder 2. In aspects, the pressure P may be less than 50 mmHg, less than 30 mmHg, less than 10 mmHg, less than 5 mmHg, or the like. In aspects, the balloon 805' may include one or more sensing tips in accordance with the present disclosure to measure the applied pressure P. In aspects, the balloon 805' may include one or more sensing tips in accordance with the present disclosure to monitor one or more physiological and/or electrophysiological signals along the walls of the bladder 2. In aspects, such monitoring may be to elucidate one or more regions 830*a-i* along the bladder wall 2 with abnormal physiological behavior (i.e., abnormal electrophysiological activity, abnormal sensory response to an applied pressure P, etc.). Such regions 830*a-i* may be designated as sites for treatment. In aspects, the surgical tool 800 may be configured to treat one or more of the regions 830*a-i* via one or more sensing tips included in the balloon 805'. In aspects, the treatment of the regions 130*a-i* may be performed via one or more electrodes included in the balloon 105'. In aspects, the surgical tool 800 may be configured so as to pass an RF current from one or more sensing tips situated on the balloon 805' to the electrode 825. In aspects, the surgical tool 800 may be configured so as to monitor electrophysiological activity at one or more sensing tips on the balloon 805' with reference to the electrode 825.

In aspects, the surgical tool 800 may be configured so as to pass a current $i_1$, $i_2$ (a DC current, an RF current, a stimulating current, a heating current, an ablating current, etc.) between one or more sensing tips on the balloon 805' and the counter electrode 840 (i.e., via one or more electrode patches 850*a,b* included therein, to the counter electrode 840 on the whole, etc.). The counter electrode 840 may be coupled 845 with a controller, a connector, a microcircuit, etc. in accordance with the present disclosure. In aspects, the counter electrode 840 may be configured and dimensioned for placement within an adjacent orifice of the body, a vagina, a rectum, etc. to facilitate communication with the surgical tool 800 during a procedure.

In aspects, a sensing tip in accordance with the present disclosure including one or more piezoresistive materials may be configured to measure a local contact pressure between the balloon and the wall of the organ. Such measurements may be performed in conjunction with the monitoring so as to relate local stresses (i.e., embodied in local tissue strains, etc.) with electrophysiological activity in the related tissues. Such relationships may be used in the formation of a metric for diagnosing a disease state, determining if a tissue site is a candidate for therapy, determining if a therapy has been successful, etc.

Figure 9:
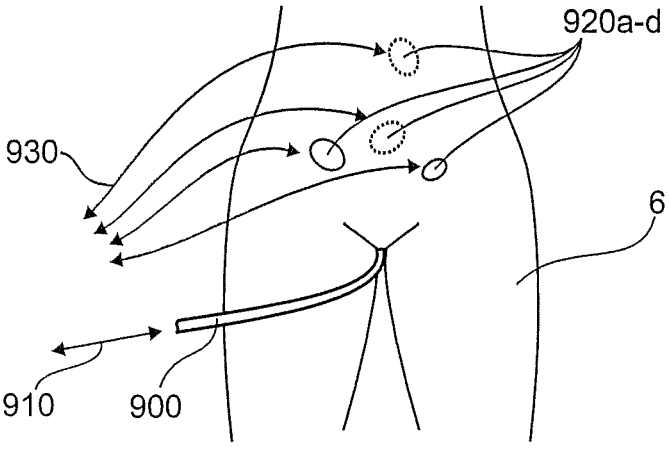
FIG. 9 shows aspects of a surgical tool with one or more remote monitoring sites in accordance with the present disclosure.

FIG. 9 shows aspects of a surgical tool 900 in conjunction with one or more remote monitoring sites 920*a-d* placed upon a subject 6 in accordance with the present disclosure. The surgical tool 900 may be placed within the subject 6 (i.e., so as to access at least a portion of an organ within the subject 6) as part of a surgical procedure. The surgical tool 900 may be configured to communicate 910 with a controller, a connector, a microcircuit (not explicitly shown) and to monitor and/or treat one or more adjacent tissues within the body in conjunction with the remote monitoring sites 920*a-d*. The remote monitoring sites 920*a-d* may be coupled 930 in electrical communication with the same controller, or microcircuit in order to provide a reference, a counter electrode, etc. for a procedure performed on the subject 6.

Such remote monitoring sites 920*a-d* may be arranged so as to monitor one or more electromyographical signals associated with pelvic muscles, the bladder, abdominal muscles, a peripheral nerve signal, etc. as part of a procedure in accordance with the present disclosure.

In aspects, such a configuration may be advantageous for general monitoring of a subject 6 (i.e., as part of a diagnostic procedure, part of a follow up procedure, etc.), as part of a urodynamic test performed on the subject 6, etc.

Figure 10:
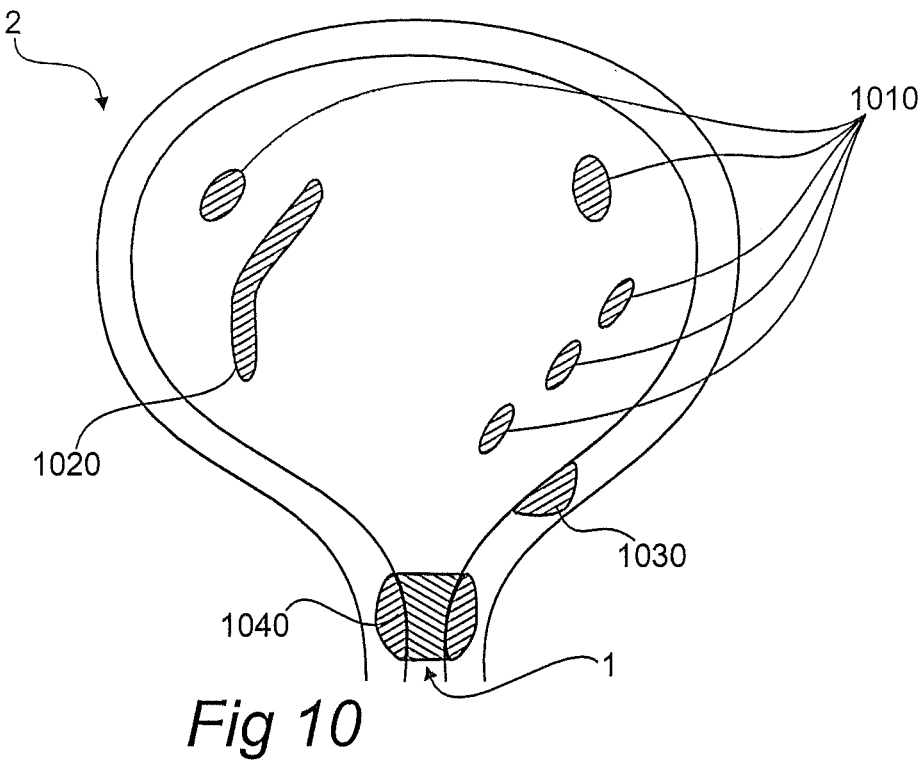
FIG. 10 shows a urinary bladder with non-limiting examples of treatment patterns thereupon.

FIG. 10 shows a urinary bladder 2 with non-limiting examples of treatment patterns 1010*a-e*, 1020, 1030, 1040 thereupon. The patterns 1010*a-e*, 1020, 1030, 1040 may be formed with a system, surgical tool, and/or one or more sensing tips in accordance with the present disclosure. The bladder wall 2 may be treated with one or more spot treatment patterns 1010*a-e* so as to treat reasonably confined regions of abnormal tissue behavior. In aspects, the bladder wall 2 may be treated with one or more track-like patterns 1020 so as to disconnect a region of abnormal electrophysiological behavior from a region of normally functioning tissues, from an associated neural circuit, etc. In aspects, the bladder wall 2 may be treated with a through-wall pattern

1030 of controlled depth into the wall of the organ. In aspects, the through-wall patterned 1030 treatment site may be controlled, so as to limit damage to the mucosal and adventitial layers of the organ wall (i.e., focused so as to affect primarily the muscular layers of the organ wall). Such control may be obtained with coolant mitigated RF ablation currents, a bolus of chemical agent delivery into the wall, etc.

In aspects, one or more regions 1040 around the bladder neck and/or the urethra 1 may be treated so as to form substantially circumferential treatment pattern there-around.

In aspects, the regions 1010*a-e*, 1020, 1030, 1040 treated during a procedure in a particular subject may be compared with regions previously treated in that subject, across a patient population, etc. so as to determine typical areas of abnormal behavior, outcomes, etc.

Figure 11:
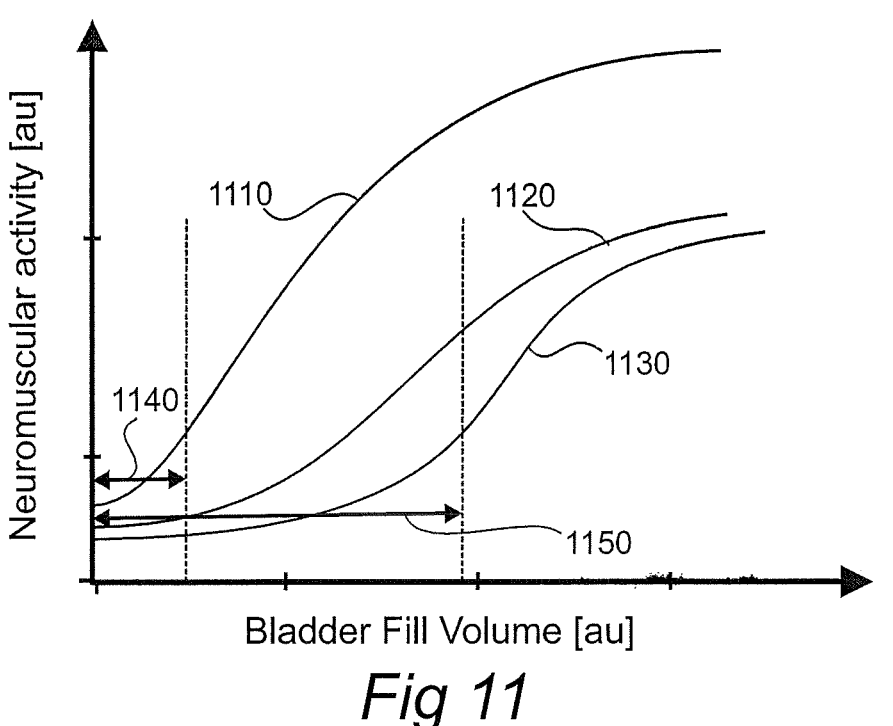
FIG. 11 shows a graphical display of the relationship between local neurological activity and bladder fill volume before, during, and after treatment with a device in accordance with the present disclosure.

FIG. 11 shows a graphical display of the relationship between local neurological activity and bladder fill volume before 1110, during 1120, and after 1130 treatment with a device in accordance with the present disclosure. The relationship shows micturition onset for a pretreated 1140 and post treated 1150 subject, demonstrating the effect of the surgical procedure on the bladder storage capacity thereof. In aspects, a procedure in accordance with the present disclosure may include assessing the micturition volume for a subject at intervals during a surgery to determine whether to continue with a surgery, to stop, to adjust the treatment site, etc.

Figure 12A:
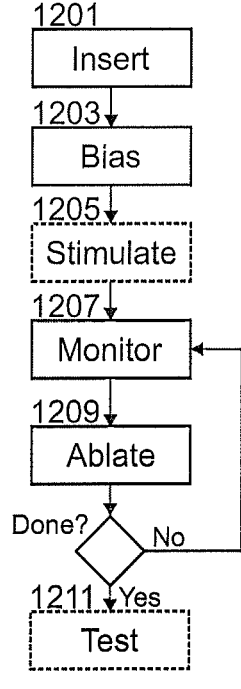
FIGS. 12a-d show aspects of methods for using a surgical tool in accordance with the present disclosure.

FIGS. 12*a-d* show aspects of methods for using a surgical tool in accordance with the present disclosure. FIG. 12*a* shows a method for treating a tissue site within a subject including inserting 1201 one or more electrodes and/or sensing tips into the subject, biasing 1203 the electrodes and/or sensing tips against the wall of an organ in the subject so as to interface with the tissues thereby, optionally stimulating 1205 the tissues with one or more of the electrodes and/or sensing tips, and monitoring 1207 the physiological and/or electrophysiological activity and/or response (i.e., to the optional stimulation 1205) to assess the functionality of the adjacent tissues. The method may also include treating 1209 (i.e., ablating, denervating, performing a neuromodulation procedure, cryoablating, ultrasonically disrupting, magnetically heating, etc.) on the tissues and determining if the procedure has been completed (i.e., such as by performing further stimulation, monitoring, etc.). If the procedure has been completed, the method may include optionally testing 1211 the subject to determine if the surgical procedure was successful or completed. If not, the method may include repeating one or more steps, if completed the method includes removing the electrodes and/or sensing tips from the subject.

Figure 12B:
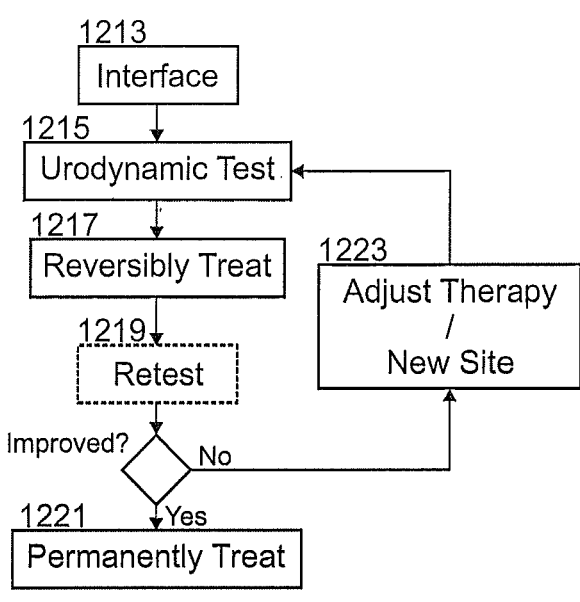

FIG. 12*b* shows a method for treating a subject in accordance with the present disclosure including interfacing 1213 an electrode and/or sensing tip in accordance with the present disclosure with a target tissue (i.e., a tissue associated with the urological system of a subject), and performing a urodynamic test 1215 to determine one or more physiological responses of the subject, to monitor target tissues during such a test, etc. The method includes reversibly treating 1217 tissues of the subject to determine if the correct treatment site has been selected, to assess the potential outcome of such a procedure, etc. The method may include 1219 optionally retesting the subject so as to see if the urodynamic test yields new results. If the test results have improved, permanently treating 1221 the target tissues, if not, adjusting the site of or one or more parameters of the therapy 1223 and repeating one or more steps in the method.

Figure 12C:
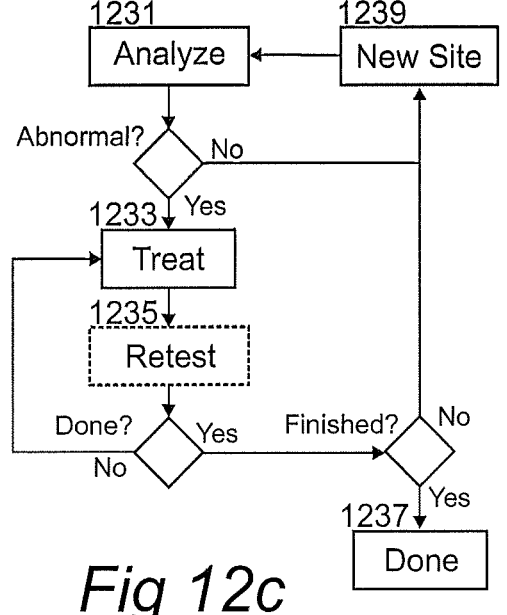

FIG. 12*c* illustrates aspects of a method for sequentially treating one or more target sites in an organ of a subject including analyzing 1231 function on tissues in the vicinity of a potential surgical site, if the tissue function is found to be abnormal treating 1233 the tissues with a surgical procedure in accordance with the present disclosure, if not, adjusting the treatment site 1239 to analyze additional tissues in the organ. If the treatment 1233 is completed, the method may include retesting 1235 the subject to determine if further treatment is necessary, if not, determining if the procedure has been completed or if more sites are to be treated. If the procedure has been completed, finishing the procedure 1237.

Figure 12D:
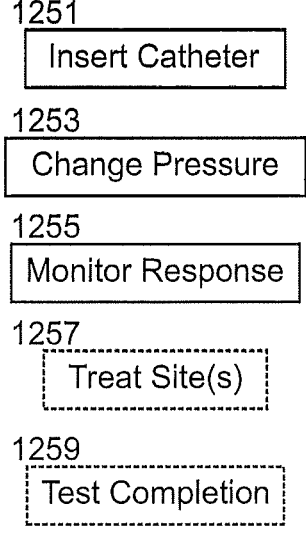

FIG. 12*d* illustrates aspects of a procedure for testing and/or treating a subject in accordance with the present disclosure including inserting a catheter 1251 into the subject so as to access the bladder thereof, changing the pressure 1253 within the bladder and monitoring 1255 the response thereto (i.e., monitoring one or more physiological and/or electrophysiological responses to the change in pressure), optionally treating 1257 one or more sites within the bladder, and optionally testing 1259 to determine if the treatment was successful. The method may include comparing the pressure changes to the electrophysiological and/or physiological activity to determine the functional state of one or more tissue sites within the bladder, to facilitate a diagnostic decision about a disease state of the subject, etc.

Other aspects of methods, variants thereof, etc. are discussed throughout the disclosure.

FIGS. 13*a-c* show aspects of a surgical tool in accordance with the present disclosure. FIG. 13*a* shows aspects of a balloon 1305 catheter configured for accessing the neck of a bladder, the balloon 1305 including one or more interconnects and associated sensing tips 1315 in accordance with the present disclosure attached thereto (i.e., patterned thereupon, laminated thereto, attached thereto, etc.). In aspects, the balloon 1305 may be deployed 1330 within the bladder so as to bring one or more of the sensing tips 1315 into intimate contact with the walls thereof. The sensing tips 1305 may be optically and/or electrically coupled 1320 with a controller, a connector, a microcircuit, etc. while the balloon interior may be provided in fluid communication 1325 with a connector, controller, a fluid reservoir, etc.

FIG. 13*b* shows aspects of an interconnect 1335 configured with one or more sensing tips 1340 in accordance with the present disclosure. The interconnect 1335 is configured for electrical and/or optical communication between the sensing tips 1340 and one or more aspects of an associated system.

FIG. 13*c* shows aspects of an interconnect 1350 including a plurality of (in this non-limiting example) exposed and coupled electrodes 1355*a-d* in accordance with the present disclosure (i.e., patterned so as to adjust the current flow there between during an ablation procedure, etc.). In aspects, the interconnect 1350 includes one or more insulating regions 1360*a-e* configured so as to isolate the underlying traces from the surrounding environment.

In aspects, the balloon 1305 may include one or more perforations and or microinjection ports configured such that a medicament may be delivered to the adjacent tissues or a surgical site in accordance with the present disclosure.

FIG. 14 shows aspects of a device 1400 for assessing local physiological response and/or treating a local tissue site 1440 in accordance with the present disclosure. The device 1400 includes a delivery system including an optional delivery sheath 1405 and a delivery member 1410 in accordance with the present disclosure configured for passage though the urethra 1 to access the bladder 2. The delivery member 1410 extends beyond the sheath 1405 so as to enter the bladder 2 and interface with the tissues thereof. The delivery member 1410 may include an actuate able part 1415 configured so as to move, sweep 1445, etc. within the bladder 2 for accessing one or more tissues sites 1440 along the wall thereof. The delivery member 1410 may include one or more sensing tips 1420, 1425, 1430 in accordance with the present disclosure to assess and/or treat one or more tissues sites in and around the organ. Some non-limiting examples are shown including an electrode 1420, a strain sensing element 1430, and a pressure sensing element 1425. In aspects, the delivery member 1410 may be configured to bias with a force F one or more sensing tips 1420 against the wall of the bladder 2 at an assessment and/or treatment site 1440.

In aspects, the system may be configured to measure tissue tone at the site 1440, measure electrophysiological response to pressure changes P, bias force F changes, etc. In aspects, the delivery sheath 1405 may include a retention feature 1435 for maintaining the position thereof in place during the procedure. In aspects, the delivery sheath 1405 may accommodate an externally applied retention feature 1465, configured so as to maintain a strain relief fit between the delivery system and the urethra 1 during a procedure. In aspects, the delivery member 1410 and/or the delivery sheath 1405 may include one or more lumens configured for fluid communication 1455 between an externally located fluid source and the bladder, suitable for fluid exchange 1450 there between during a procedure. In aspects, the sensing tips 1420, 1430, 1425 may be electrically coupled 1460 with a connector, controller, and/or a microcircuit in accordance with the present disclosure.

In aspects, the system may include one or more electrodes 1420 configured to pass a current (i.e., a stimulating current, an ablating current, a tissue heating current, for purposes of diagnostics, temporary treatments, permanent treatments, etc.) between one or more of the electrodes 1420 with one or more aspects of the system and/or a counter electrode 1480 located remotely from the surgical site 1440 (i.e., as a body patch, an electrode inserted into the vagina, the rectum, a transcutaneously placed electrode, etc.).

Such a tool 1400 may be configured to perform one or more aspects of a method and/or surgical procedure in accordance with the present disclosure.

Figures 15, 17:
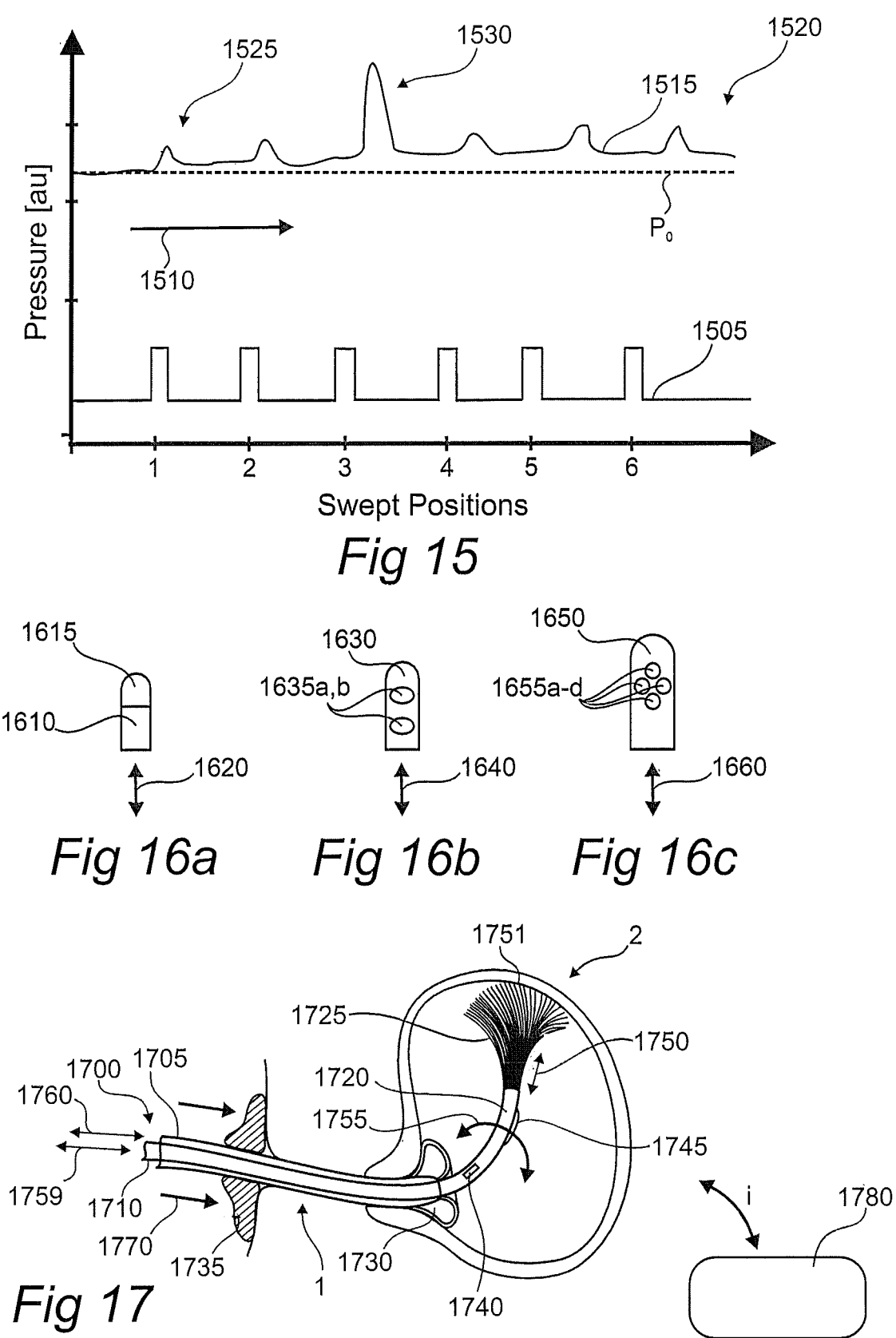
FIG. 15 shows a graphical relationship between a probe and physiological measurements performed with a device in accordance with the present disclosure.
FIG. 17 shows aspects of a microfilament array based surgical tool in accordance with the present disclosure, placed within a urinary bladder.

FIG. 15 shows a graphical relationship between a probe and physiological measurements performed with a device in accordance with the present disclosure. In aspects, the probe may be an aspect of a balloon, a delivery member tip, a wire mesh, etc. in accordance with the present disclosure. The relationship under study may pertain to a global pressure application within the bladder, or a local pressure application applied at the monitoring site, or a site in electrophysiological communication with the monitoring site. In aspects, the procedure may include applying a stimulus 1505, perhaps a sequence of stimuli, etc. to the tissue site (i.e., either globally, locally, etc.). Such stimuli may include an electrical impulse, a thermal pulse (i.e., local heating), a local pressure application (i.e., force from a local probe tip, etc.), or the like. In aspects, the response 1515 to the stimuli 1505 may be monitored 1520 for purposes of assessment, therapeutic progress, determining regions of abnormal activity, etc. In the non-limiting example shown, the stimuli 1505 is a local current pulse, applied with an electrode in accordance with the present disclosure. The response 1515 is the local pressure measured on the electrode (i.e., applied to the electrode while biased against the tissues) in response to the stimuli 1505. The electrode is moved slowly 1510 along the surface of the tissue as the stimuli 1505 are applied locally thereto. Alternatively, additionally, or in combination the stimuli 1505 may be applied over a region of the tissues via an array of sensing tips (i.e., as patterned on a balloon, as part of a brush-like tool, etc.) so as to achieve the same effect as a probe, without the need to move one or more elements across the tissue surface.

The response 1515 is shown at multiple sites along the tissue surface. As can be seen the change in pressure from a baseline level $P_0$ is reasonably consistent at a plurality of sites 1525 thereupon but may be distinctly increased at one or more sites 1530, such sites may be candidates for a surgical procedure, may be indicative of a hypersensitivity, etc. Such information may be used for diagnostic purposes, to identify suitable surgical sites, to identify the extent of a surgical procedure, etc.

FIGS. 16*a-c* show aspects of tip electrode configurations for a surgical tool in accordance with the present disclosure. FIG. 16*a* shows an electrode 1615 coupled with a probe 1610 (i.e., equivalently part of a delivery module, microfinger, etc.) each in accordance with the present disclosure. The electrode 1615 may act as a monopolar configuration, for communication with one or more electrodes in the system (not explicitly shown) in order to interface with tissues adjacent thereto during a procedure. The electrode 1615 may be coupled with 1620 one or more aspects of a system in accordance with the present disclosure via the probe 1610.

FIG. 16*b* shows a delivery module 1630 coupled with two electrodes 1635*a,b*, each in accordance with the present disclosure. The electrodes 1635*a,b* are arranged in a bipolar electrode arrangement for interfacing with a local tissue site. Such an arrangement may be advantageous for local field vectors, movement, a bipolar signal, etc. or for providing a current to a precise region of tissue in the vicinity thereof.

FIG. 16*c* shows a probe 1650 coupled to a plurality of electrodes 1655*a-d* each in accordance with the present disclosure. The electrodes 1655*a-d* are arranged in a quadripolar electrode arrangement for interfacing with a tissue site within the body of a subject. The quadripolar electrodes 1655*a-d* may be arranged so as to allow for multi-site capture of electrophysiological activity on the subject. Such an arrangement may be advantageous for generating a field vector in the vicinity of the probe 1650, for mapping electric field propagation across the surface of the subject, etc.

FIG. 17 shows aspects of a microfilament array 1725 based surgical tool 1700 in accordance with the present disclosure, placed within a urinary bladder 2. The surgical tool 1700 includes a delivery system including an optional delivery sheath 1705 and a delivery member 1710 in accordance with the present disclosure configured for passage though the urethra 1 to access the bladder 2. The delivery member 1710 extends beyond the sheath 1705 so as to enter the bladder 2 and move therein during a procedure. The delivery member 1710 may include an actuate able part 1720 configured so as to move, sweep 1755, etc. within the bladder 2 for accessing one or more tissues sites along the wall thereof. Protruding from the delivery member 1710 is a microfilament array 1725 in including a plurality of microfilament microfingers each in accordance with the present disclosure. The filament array 1725 may be slide ably deployable 1750 from the delivery member 1710 so as to extend therefrom and access the tissues for purposes of monitoring, mapping, treating, ablating, delivering a medicament, etc. The microfilaments may be biased 1751 against the wall of the bladder as part of a procedure. In aspects, the microfilaments 1725 may include sensing tips, electrodes, etc. each in accordance with the present disclosure.

In aspects, the delivery sheath 1705 may accommodate an externally applied retention feature 1735, configured so as to maintain a strain relief fit between the delivery system and the urethra 1 during a procedure. In aspects, the externally applied retention feature 1735 may be biased 1770 towards the body of the subject in order to retain the delivery sheath 1705 in position during a procedure. In aspects, the delivery member 1710 and/or the delivery sheath 1705 may include one or more lumens configured for fluid communication 1759 between an externally located fluid source and the bladder, a restraining balloon 1730, or the like.

In aspects, a surgical device in accordance with the present disclosure may include a means for communicating fluid between the organ and an external controller, fluid reservoir, etc. In aspects, the fluid may be heated to a predetermined temperature so as to affect the function (either temporarily, or permanently) of the organ walls during a procedure. The surgical device may be configured with one or more sensing tips configured to monitor the fluid temperature, tissue temperature, electrophysiological activity, pressures, etc. within the organ and/or at sites along the wall of the organ during the procedure. Such a configuration may be advantageous to treat an entire internal wall of an organ with feedback so as to minimize the amount of damage necessary to achieve the surgical goals of the procedure. In aspects, the fluid may be heated with an electrode setup, an RF heating electrode configuration, an external heater (i.e., with a recirculating fluid transfer hydraulic circuit to exchange fresh fluid with spent fluid within the organ), via magnetic particles in the fluid coupled with an electromagnetic field to agitate such particles, etc. In aspects, the fluid may include medicament such as a chemotherapy drug, etc. In aspects, the surgical device may be configured to monitor electrophysiological activity of a cancerous tumor site to determine when a treatment has successfully altered function thereof.

Such a system may be advantageous for treating bladder cancer and optionally performing hyperthermia based chemotherapy thereof. In aspects, a system in accordance with the present disclosure may be advantageous for monitoring/treating cancerous tumors within the body of the subject.

Hyperthermia is the targeted application of elevated temperatures in cancerous regions to improve the efficacy of traditional treatments including chemotherapy. In aspects, the fluid may contain iron oxide nanoparticles delivered via catheter as an intravesical ferrofluid to interact with a magnetic field to heat the fluid during the procedure. The magnetic field may be used to agitate the nanoparticles, causing particle rotation and magnetic domain realignment, both generating heat. The temperature of the fluid may be elevated by 3-8 degrees celcius as part of the hyperthermia treatment. In aspects, the chemotherapeutic agent may be methotrexate, vinblastine, doxorubicin, and cisplatin, cisplatin plus fluorouracil (5-FU), mitomycin with 5-FU, Gemcitabine and cisplatin, Methotrexate, vinblastine, doxorubicin (Adriamycin), and cisplatin (called M-VAC), Carboplatin and either paclitaxel or docetaxel, etc.

In aspects, one or more of the microfilaments 1725 may include one or more electrodes (i.e., generally at the tip thereof) configured to monitor a local electrophysiological signal, pass a current i (i.e., a stimulating current, an ablating current, a tissue heating current, for purposes of diagnostics, temporary treatments, permanent treatments, etc.) between one or more of the electrodes with one or more aspects of the system and/or a counter electrode 1780 located remotely from the surgical site (i.e., as a body patch, an electrode inserted into the vagina, the rectum, a transcutaneously placed electrode, etc.). In aspects, the microfilaments 1725 may be electrically coupled 1760 with a connector, controller, and/or a microcircuit in accordance with the present disclosure.

In aspects, the delivery member 1710 may include one or more sensing tips 1740, 1745 in accordance with the present disclosure to assess and/or treat one or more tissues sites in and around the organ. Some non-limiting examples are shown including, a strain sensing element 1745, and a pressure sensing element 1740. In aspects, the delivery member 1710 may be configured to bias the microfilament array 1725 against the wall of the bladder 2 at an assessment and/or treatment site 1440, to monitor such bias force, etc.

Such a tool 1700 may be configured to perform one or more aspects of a method and/or surgical procedure in accordance with the present disclosure.

FIGS. 18a-e show aspects of microfilament tips in accordance with the present disclosure. FIG. 18a shows aspects of a microfilament with a conducting, resistive and/or semiconductive core 1805 (e.g., platinum, carbon, titanium, stainless steel, nickel titanium, silver, gold, spring steel, etc.). In aspects, the core 1805 may be dimensioned with a diameter of less than 100 um, less than 50 um, less than 25 um, less than 12 um, less than 7 um, less than 5 um. In aspects, one or more segments of the core 1805 may be covered with a clad layer 1810.

In aspects, the clad layer 1810 may include a passivating material, a highly conducting material, a bioactive material, an electrically insulating material, etc. In aspects, the clad layer 1810 may be configured so as to isolate the core 1805 from the surroundings, to improve the longitudinal conductivity of the core 1805 (i.e., in the case of a metallic clad layer 1810), provide unique analyte identification means (i.e., in the case of a bioactive clad layer 1810, an enzymatic layer, etc.). In aspects, the clad layer 1810 may result in a clad diameter of less than 200 um, less than 100 um, less than 25 um, less than 12 um, less than 6 um, etc. In aspects, the clad layer 1810 may be thinner than 1 um, thinner than 0.5 um, thinner than 0.1 um, etc. In aspects, the clad layer 1810 may provide improved optical transmission down an optically oriented fiber 1805.

In aspects, one or more segments of the clad layer 1810 or the core 1805 may be coated with an insulating layer (or the clad layer 1810 may be insulating). The insulating layer may include a dielectric material, a thick walled polymer material, a ceramic, etc. The insulating layer may be configured to enhance electrical isolation and/or reduce cross talk between microfilaments in a microfilament array in accordance with the present disclosure. In aspects, the insulating layer may have a diameter of less than 250 um, less than 200 um, less than 100 um, less than 50 um, less than 25 um, less than 10 um, etc. In aspects, the insulating layer may be provided with differing thickness (i.e., different overall microfilament diameter) along alternative segments thereof. In one non limiting example, the insulating layer is relatively thin near to the distal region of the microfilament but gradually increases in thickness in the proximal direction thereof.

In aspects, the clad layer 1810 and/or the insulating layer may be removed and/or otherwise not present over one or more segments of the microfilament. Such a configuration may be advantageous for altering the flexibility, altering the intercommunication of the microfilaments, allowing for interconnects between microfilaments, etc.

FIG. 18*b* shows aspects of a microfilament tip including a core 1825 and a clad layer 1830 in accordance with the present disclosure configured such that only the tip of the core 1825 is exposed to the surrounding environment during a procedure. Such a configuration may be advantageous for providing a minimal exposed conducting area of the microfilament while providing isolation along the entire length thereof (i.e., via the clad layer 1830) without profiling or otherwise purposefully shaping the tip thereof.

FIG. 18*c* shows aspects of a microfilament tip including a core 1850 and a clad layer 1855 in accordance with the present disclosure with a gradually increasing thickness for the clad layer 1855.

FIG. 18*d* shows aspects of a microfilament tip including a core 1870 and a clad layer 1875, the core 1870 wound around 1880 the tip thereof to form an increased electrode area for interfacing with a surrounding tissue site.

FIG. 18*e* shows aspects of a microfilament as outlined in FIG. 18*d* with an additional plating or coating procedure 1885 to increase the area, or strength or to plate the core 1870 or core wound region with an additional electrode material 1890. In aspects, the additional electrode material 1890 may include a conjugated polymer, a metal, a reduced material, etc.

FIG. 19 shows aspects of a microfilament array 1920 based surgical tool in accordance with the present disclosure. The tool includes a delivery member 1910 including a lumen through which a plurality of microfilaments 1915 is passed. The array 1920 may be slide ably arranged within the delivery member 1910 so as to allow for deployment 1945 of the array 1920 therefrom during a deployment procedure.

In aspects, the delivery member 1910 may be actuate able so as to allow for bending, sweeping, and/or torsional 1930 movement of the array 1920 during operation. The delivery member 1910 may include one or more lumens through which are provided tendons for actuating 1940, 1935 the delivery member 1910 during a procedure.

In aspects, the microfilaments 1915 in the array 1920 may be individually separated (i.e., not rigidly connected) so as to maintain a highly flexible structure. In aspects, the microfilament array 1920 may be enclosed within the delivery member 1910 with a lubricating fluid, the fluid may be an insulating fluid, so as to assist with isolation between fibers in the array during use.

FIGS. 20*a-c* show aspects of a microfilament array based surgical tool in accordance with the present disclosure. FIG. 20*a* shows a bundle 2005 for microfilaments each including a core 2010 and a clad layer 2015 in accordance with the present disclosure. The tightly packed bundle 2005 may be interfaced with a mating connector, microcircuit, or MEMs based interconnect in order to extract one or more signals therefrom in a device.

FIG. 20*b* illustrates a connector 2020 for interfacing with a microfiber bundle 2030 in accordance with the present disclosure. The microfilament bundle 2030 may be configured such that individual fibers from the bundle 2030 may be separated out and interfaced with a plurality of leads 2035 in the body 2025 of the connector. The connector 2020 may thus provide a means for communicating 2040 with the microfilament bundle 2030 in a system in accordance with the present disclosure.

FIG. 20*c* illustrates a block connection 2050 of a microfilament bundle 2065 in accordance with the present disclosure, the filaments 2060 of the microfilament bundle 2065 frozen into a restraining block 2055. The bundle 2065 and restraining block 2055 may be faced and polished so as to interface with the filaments 2060 therein during use (i.e., by coupling the polished face with a mating microconnector, etc.).

FIGS. 21*a-c* show aspects of measurements made over a surface with a microfilament array based surgical tool in accordance with the present disclosure. FIG. 21*a* shows a schematic of an organ wall 2 and an array of contact points 2110 indicating interfacing points created by an array of mating sensing tips in accordance with the present disclosure interfacing with the surface 2105 of the organ wall 2. The plurality of contact points 2110 may represent a collection of sites which may be suitable for interacting with the wall, measuring electrophysiological activity on the wall, delivering a current to the wall, etc. In aspects, physiological and/or electrophysiological data may be collected from each of the contact points 2110 individually by each of the associated sensing tips to map the activity over the surface, assess functionality of the surface, determine which sites may be suitable targets for treatment, etc.

FIG. 21*b* shows time series trends of accumulated pressure measured with an array of sensing tips in accordance with the present disclosure. An individual trend 2125 obtained from a particular sensing tip within the array demonstrates the time series pressure experienced by the individual sensing tip as it is scanned across the organ wall. An aggregate trend 2130 is also shown obtained by summation of the signals obtained by all of the sensing tips in the array. In aspects, the relationships between individual trends 2125 and aggregate trends 2130 may be advantageous for mapping, determining function along the organ wall, identifying abnormal behavior of sites along the wall, determining pressure and/or electrophysiological wave propagation over the wall during an event, a test, etc.

FIG. 21*c* shows an image obtained from a collection of contact points 2110 created by an array of sensing tips 2105 in accordance with the present disclosure in contact with an anatomical site in the body. The image demonstrates propagation of a wave 2115 across the contact points 2110 and illustrates the direction of travel of the wave 2120, 2125 to one or more future sites 2130, 2135. The image and location of the contact points 2110 within the image may be determined from the know positioning of sensing tips in a system in accordance with the present disclosure (i.e., along the face of a balloon, etc.). In aspects, the positioning of the sensing tips against the wall may not be known a priori (i.e., in an arrangement with freely moving microfingers, microfilaments, etc.). In aspects, the positioning of sensing tips within the array may be, at least partially determined from the sensed signals, through correlation of wave propagation throughout the array during a monitoring session. In aspects, a wave propagation algorithm may be used to approximate the positioning of one or more sensing tips against the wall during the monitoring, etc. Other aspects of such configurations are discussed throughout this disclosure.

Figure 22:
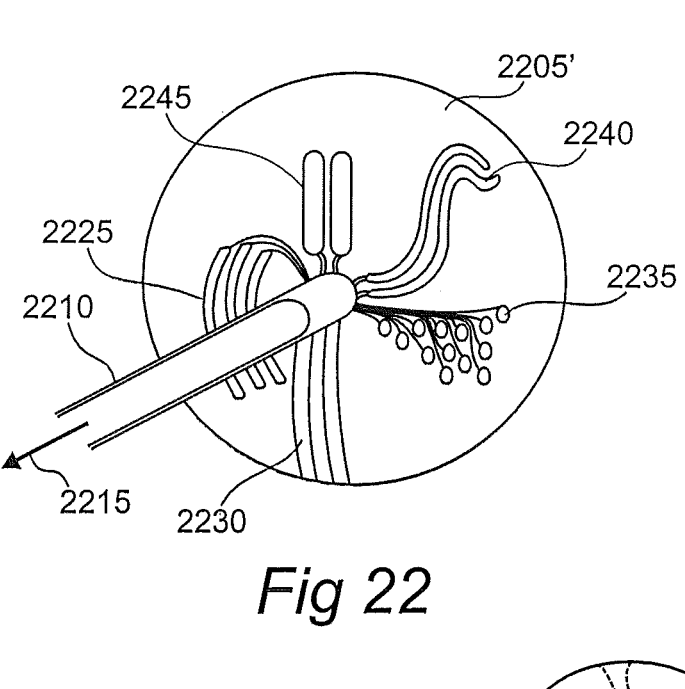
FIG. 22 shows aspects of a balloon based surgical tool in accordance with the present disclosure.

FIG. 22 shows aspects of a balloon 2205' based surgical tool in accordance with the present disclosure including a range of electrodes 2225, 2230, 2235, 2240, 2245 for interfacing with a tissue surface. The balloon 2205' may be provided in fluid communication 2215 with aspects of an associated system through a delivery member 2210 attached thereto. Shown in FIG. 22 is a cluster of point electrodes 2235, a pair of tortuous path based electrodes 2240, a pair of tab style electrodes 2245, a pair of radially oriented strip electrodes 2230, a collection of circumferentially oriented electrodes 1825. In aspects, alternative electrode arrangements may be configured for tasks such as forming particular ablation patterns on the walls, for monitoring different regions of the balloon, etc.

Figure 23:
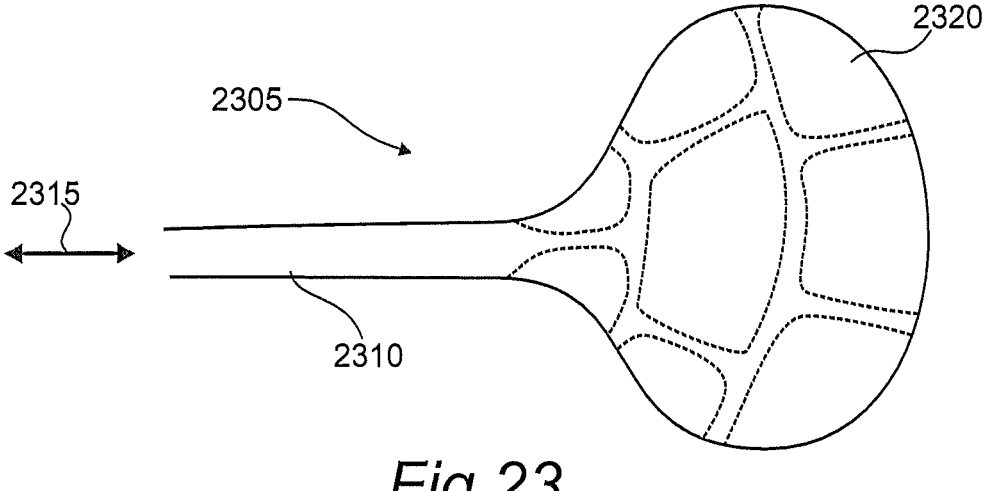
FIG. 23 shows assessment zones associated with a balloon based device in accordance with the present disclosure.

FIG. 23 shows assessment zones 2320 associated with a balloon based device 2305 in accordance with the present disclosure. The balloon and associated delivery member 2310 may be provided in fluid communication and/or electrical communication 2315 between one or more sensing tips located in one or more of the regions 2320 with a controller, connector, microcircuit, etc. The grouping of sensing tips into regions 2320 on the balloon may be advantageous for correlating potential treatment sites with designated regions of the bladder under assessment. As data pertaining to successful outcomes is collected, such regional breakdown of the affected areas will be useful in redesigning the surgical tools, surgical approaches, selecting regions to test, adjusting treatment criteria, etc. for the patient population. In aspects, such regions 2320 may be broken down into one or more of a region near a middle umbilical ligament, near one or more lateral umbilical ligaments, near to a urethral opening, near the center of Trigone, Rugae, near the neck of the bladder, near a sphincter, a urethral sphincter, combinations thereof, or the like.

Figure 24:
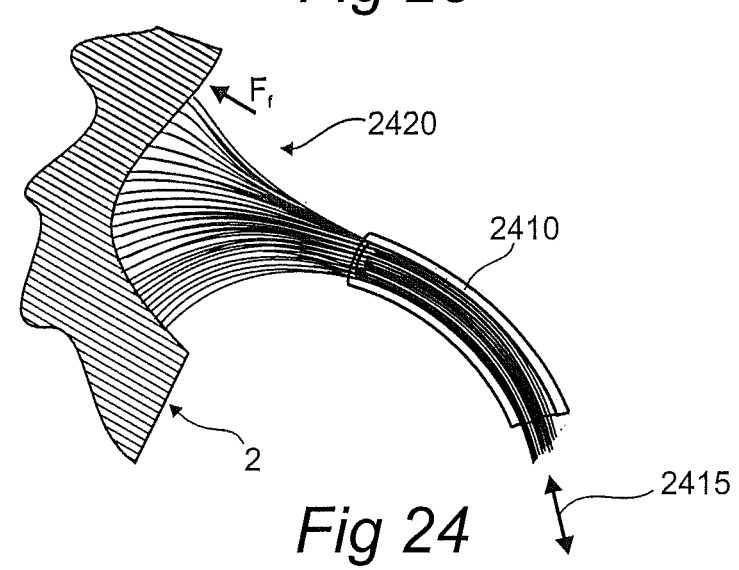
FIG. 24 shows aspects of a microfilament based surgical tool in physical contact with a tissue site in accordance with the present disclosure.

FIG. 24 shows aspects of a microfilament based surgical tool in physical contact with a tissue site in accordance with the present disclosure. The tool includes a microfilament array 2420 in accordance with the present disclosure and a delivery member 2410 through which the array 2420 may be coupled 2415 with a controller, etc. The microfilament array 2420 is shown biased with a force $F_f$ against the wall of an organ 2 during a procedure. In aspects, the microfilaments in the array 2420 may be sufficiently elastic such that the force $F_f$ may be highly predictable. In addition, due to the configuration of the array, each microfilament may reliably contact the organ wall during a procedure. Such an arrangement may be advantageous for maintaining a reliable contact force between a plurality of contact sites and the wall of the organ during a procedure.

FIGS. 25a-c show aspects of an implantable device in accordance with the present disclosure and a schematic of an implantable device attached within the inner wall of a urinary bladder. FIG. 25a shows aspects of an implantable device for monitoring and/or modulating neural activity along the wall of a hollow organ (i.e., a bladder, a uterus, a rectum, etc.) in accordance with the present disclosure. The implantable device includes one or more sensing tips 2520, 2525 each in accordance with the present disclosure configured so as to monitor one or physical or physiological parameters in the vicinity thereof during a surgical procedure, following a surgical procedure, during a monitoring session, during a urodynamic procedure, during a patient assessment, etc. The sensing tips 2520, 2525 are shown as electrodes in this non-limiting example.

The implantable device includes a housing 2510 including one or more microcircuits 2515 configured to monitor signals at the sensing tips 2520, 2525, to perform signal conditioning, and to communicate 2535 with an outside reader, controller, operating device, etc. The housing 2510 may further include a power source such as a battery, a biofuel cell (i.e., a glucose biofuel cell, a urine based biofuel cell, etc.), or an energy harvesting subsystem so as to capture kinetic energy, energy from an incident RF signal, or the like. The implantable device includes a tail 2530 which may function as a whip antenna for communicating 2535 with an external reader, a tether, a removal cord, etc.

In aspects, the implantable device may be configured to monitor neural activity, electromyographic information, urodynamics, bladder pressures, and/or physiological information for a period of time following a surgical procedure (i.e., days, weeks, months, indefinitely) following such a procedure. In aspects, the implantable device may perform additional neuromodulation procedures (i.e., RF ablation procedures) in the case that the neural activity returns to an abnormal state, etc. In aspects, the power supply may be configured to store sufficient amounts of energy such that the RF ablation procedure may be performed without external interconnection. Between procedures, the power supply may be recharged, for example via a wireless recharging system, or the like.

FIG. 25b shows an implantable device in accordance with the present disclosure placed within a bladder 2 during an extended monitoring/treatment session. The implantable device is shown positioned near to the neck of the bladder 2 and anchored to the wall of the bladder via a plurality of hook-like electrodes 2520/2525, in this non-limiting example also providing electrode function for monitoring local EMG during the monitoring session. In aspects, the implantable device may include a pressure sensing tip for monitoring bladder pressures in coordination with the EMG monitoring. The implantable device includes a housing 2510 and a whip antenna 2530 for communicating 2535 with an externally placed reader, etc. Several potential attachment sites 2540a-h are shown located around the walls of the bladder 2.

FIG. 25c shows an implantable device in accordance with the present disclosure placed within a bladder 2 during an extended monitoring/treatment session. The implantable device is shown positioned near to the neck of the bladder 2 and anchored to the wall of the bladder via a plurality of hook-like electrodes 2555a,b/2560, in this non-limiting example also providing electrode function for monitoring local EMG during the monitoring session. In aspects, the implantable device may include a pressure sensing tip for monitoring bladder pressures in coordination with the EMG monitoring. The implantable device includes a housing 2550 and a tether 2560 for communicating 2575 with an externally placed reader, etc. The tether 2560 is electrically and mechanically coupled with the housing 2550 and arranged so as to traverse the urethra 1, extending to the outside of the body of the subject. The tether 2560 may include one or more electrodes 2565a-c for assessing electrophysiological activity within the urethra 1 during a monitoring session. In aspects, the tether 2560 may include an antenna, optionally positioned within a region of the tether 2560 near to the surface or outside the subject so as to improve the communication range thereof. In aspects, the tether 2560 may be used to withdraw the implantable device from the subject after the monitoring session, follow-up, therapy, etc. is completed.

In aspects, the implantable device 2550 may include an external tab housing 2580 attached to the tether 2560. The tab housing 2580 may be configured for easy removal of the implant post procedure, may include one or more of a power source, an antenna, microelectronics, etc. for communicating with the sensing tips included in the housing 2550 while allowing for a reduction in the size of the implantable portion of the device.

In aspects, an implantable device in accordance with the present disclosure may include one or more bioadhesives to suitably bond the housing 2510, 2550 to tissues near a surgical site. Bioadhesives may be non-toxic, non-fouling and biocompatible so as to help minimize the foreign body response during the monitoring process. Some suitable bioadhesives may include polysiloxanes, polyacrylates, polyisocyanate macromers or mixtures (US Patent Application No. 2008/0339142), fibrin sealants, albumin glue with gluteraldehyde as crosslinker, hydrogels such as those formed from chitosan and poly(ethylene glycol) (U.S. Pat. No. 6,602,952), gelatin based adhesive with resorcinol-formaldehyde complex, oxidized polysaccharides with water-dispersible, multi-arm polyether amine (US Patent Application No. 2006/0078536) among others. The bioadhesives as noted above may also be sufficiently stable so as to retain the implantable device in place during the postoperative recovery period but yet sufficiently biodegradable such that retention is only maintained for a reasonable period of time. In the case of a urodynamic monitoring application, the implantable device may be retained for up to 3 weeks, 2 weeks, 1 week, 3 days, or 1 day.

In aspects, the housing 2510, 2550 may include one or more eyelets adapted so as to accept a suture or staple. Such sutures or staples may be biodegradable for easy detachment after a known period of retention. Some examples of suitable materials include amino acid based families, polyester urethanes, polyester amides, polyester ureas, polythioesters, and polyesterurethanes.

In aspects, the implantable device or the housing 2510, 2550, may include a coating, a chamber, a release layer, etc. for sustained release of a neuromodulating substance in accordance with the present disclosure into the surrounding tissues of the bladder 2. In aspects, the implantable device may include a neuromodulating substance, perhaps confined in a retaining medium (i.e., a hydrogel matrix, etc.) and the substance may leach into the surrounding tissues over time, after placement during a surgical procedure. In aspects, the neuromodulating substance may be a potent denervating agent (i.e., a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, etc.), a neuroblocking agent (i.e., capsaicin, an anesthetic, lidocaine, tetanus toxin, quaternary ammonium salts, a pachycurare, a leptocurare, acetylcholine, aminosteroids, etc.).

In aspects, the retaining medium may be configured so as to crosslink via a radial polymerization procedure (i.e., photopolymerization), a click polymerization procedure (i.e., an oxime click chemistry based hydrogel), or the like. Such form-in-place hydrogels known in the art of bioscaffold formation and bioadhesives may be adapted for use in this application.

In aspects, the retaining medium may be configured with one or more biodegradable aspects, such that over time (i.e., in a controlled fashion), the retaining medium may breakdown and further neuromodulating substance may be released into the surrounding tissues.

In aspects, the implantable devices discussed in FIGS. 25a-c may be configured to monitor the effect of the neuromodulating substance on the surrounding tissues over time, for following up on a surgical procedure, etc.

Figure 26:
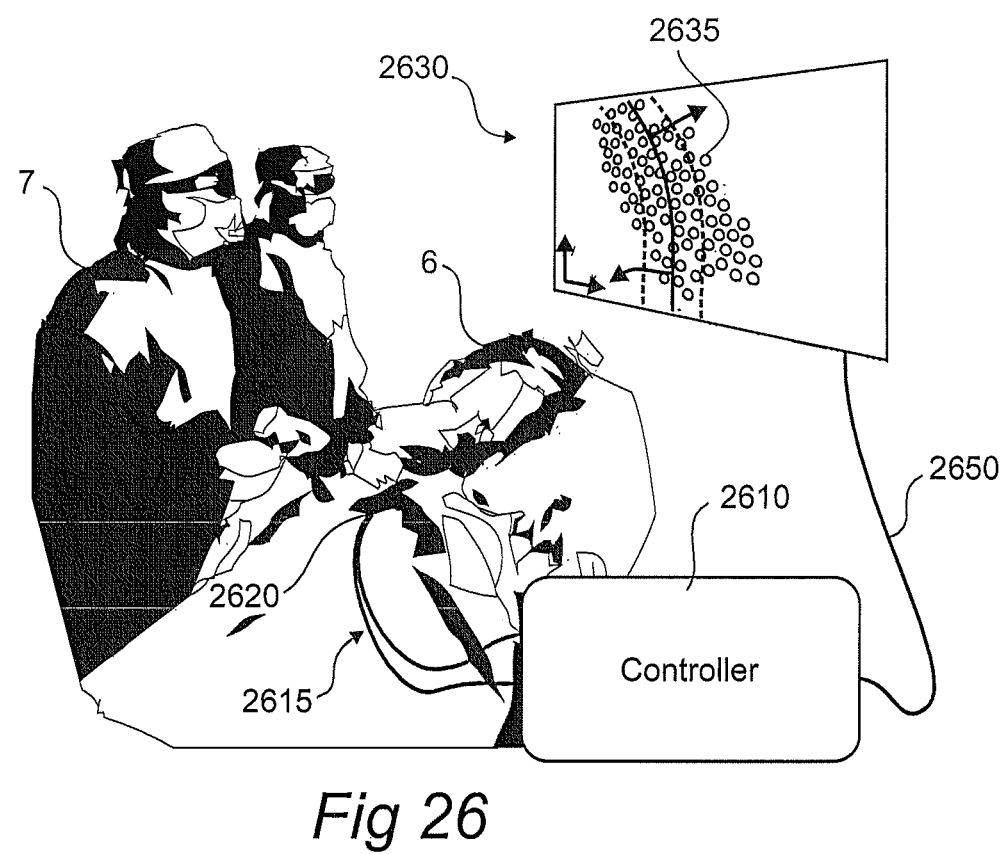
FIG. 26 shows aspects of a system in accordance with the present disclosure.

FIG. 26 shows aspects of a system in accordance with the present disclosure. The system includes a controller 2610 coupled via one or more cables, connectors, etc. 2615 with a surgical tool 2620 in accordance with the present disclosure. The controller 2610 may include one or more user interfaces through which a user 7 may interact with the surgical tool 2620 before (i.e., via calibration, testing, etc.), during (i.e., via moving aspects of the tool, monitoring temperatures, impedances, etc.), and/or after a procedure on a subject 6. The controller 2610 may be coupled 2650 (i.e., mechanically or wirelessly) to a display 2630 one or more aspects of the surgical, monitoring, or mapping 2635 process to one or more of the users 7. Aspects of such feedback have been discussed throughout the present disclosure.

Figure 27A:
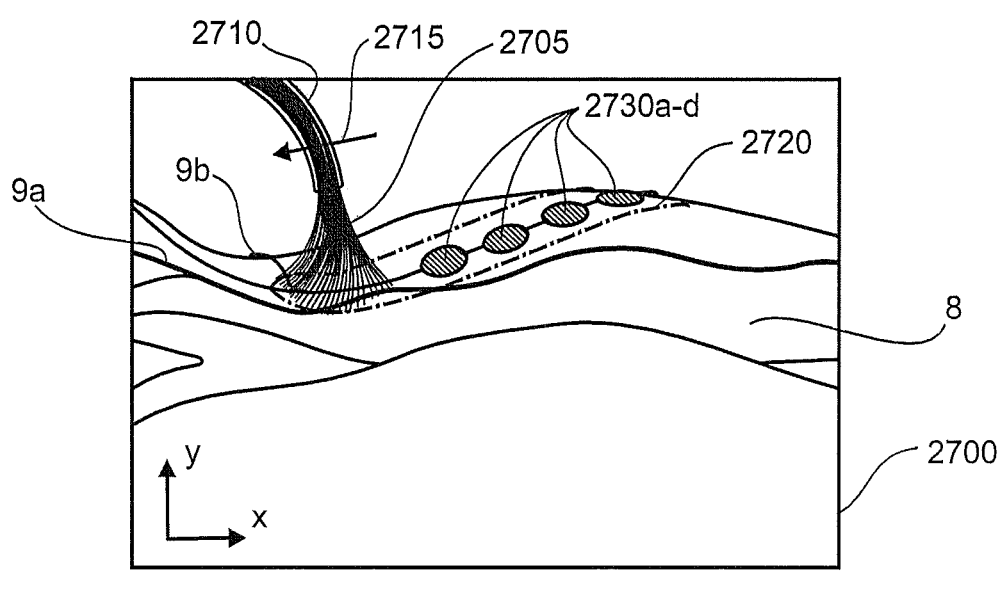
FIGS. 27a-c show aspects of a system for mapping and/or overlaying physiological response onto a surgical display during a procedure in accordance with the present disclosure.
Figure 27B:
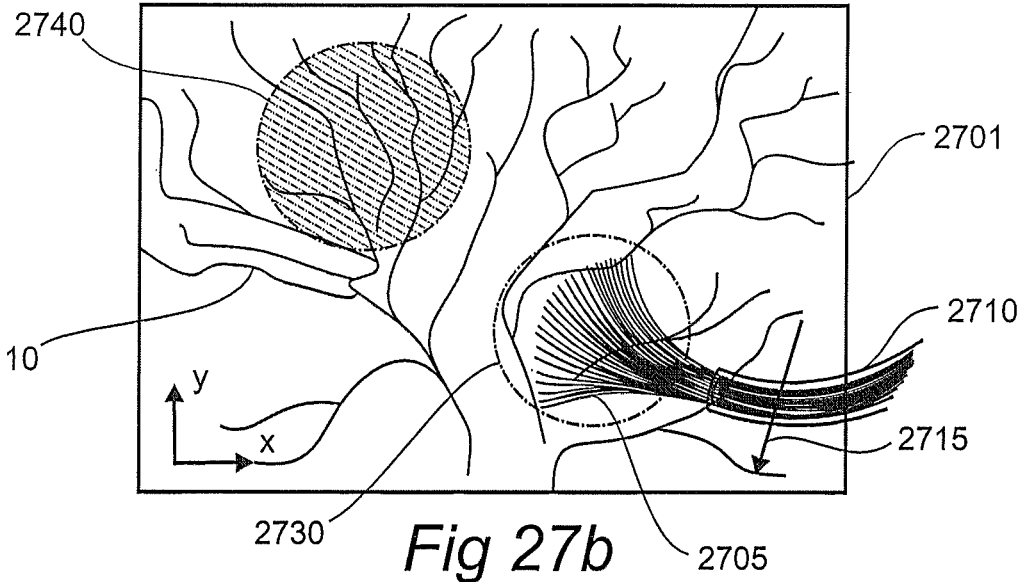
Figure 27C:
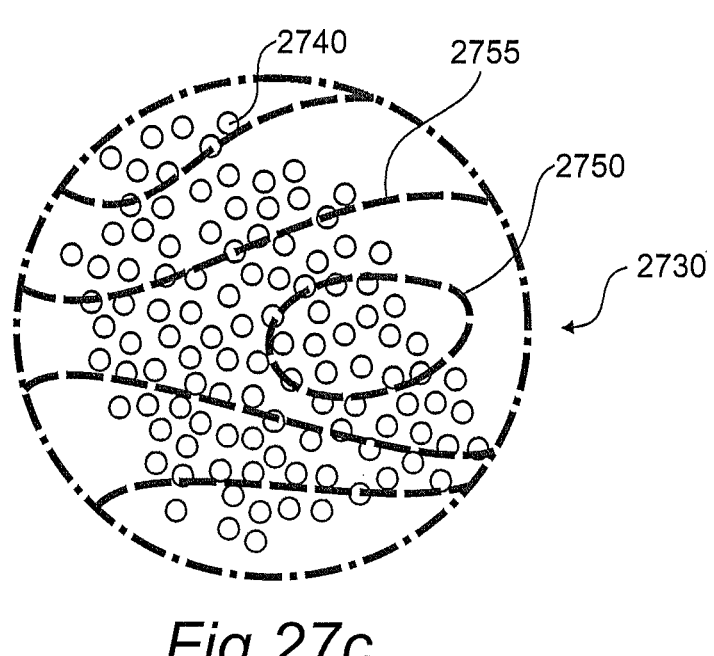

FIGS. 27a-c show aspects of a system for mapping and/or overlaying physiological response onto a surgical display during a procedure in accordance with the present disclosure. FIG. 27a shows aspects of an image 2700 of an anatomical structure 8 (in this case an artery) including a plurality of target tissues 9a,b (in this case nerves running along the artery wall, which may not be visible in a naturally obtained image). The image 2700 is combined with an augmented reality based overlay of electrophysiological activity as measured by a surgical tool 2710 including a plurality of sensing tips (i.e., herein embedded into microfilaments 2705) in accordance with the present disclosure. The surgical tool 2710 may be configured to indicate electrophysiological activity in the vicinity thereof as it interacts 2715 (i.e., laid against, biased towards, swept over, etc.) the tissues. In aspects, the augmented reality overlay 2720 may be used to help a surgeon determine where a treatment should be applied to a surface of the tissues, where an abnormal tissue site, or physiological function is being measured, etc. As shown, the image includes a series of site ablations 2730a-d created by the surgical tool 2710 and highlighted on the image 2700 for a surgeon to help guide the procedure as it progresses.

FIG. 27b shows an image 2701 including the wall of an organ covered in microvasculature 10 based features. Indicated in the image 2701 is a region 2740 of abnormal activity highlighted for a user and a region 2730 under scan with a surgical tool 2710 in accordance with the present disclosure. The surgical tool 2710 is being swept 2715 over the surface so as to interface a plurality of sensing tips (i.e., herein embedded into microfilaments 2705) in accordance with the present disclosure with the surface for purposes of interfacing therewith.

FIG. 27c shows a region 2730 of a scan highlighting an array of contact points 2740 between sensing tips and the tissues site. An overlay of macroscopic electrophysiological activity is shown over the region 2730 highlighting contours 2755, 2750 formed from the microscopic electrophysiological signals obtained by the sensing tips. As shown, a contour 2750 indicates a potential source of the activity, which may warrant treatment, further investigation, etc.

Figure 28:
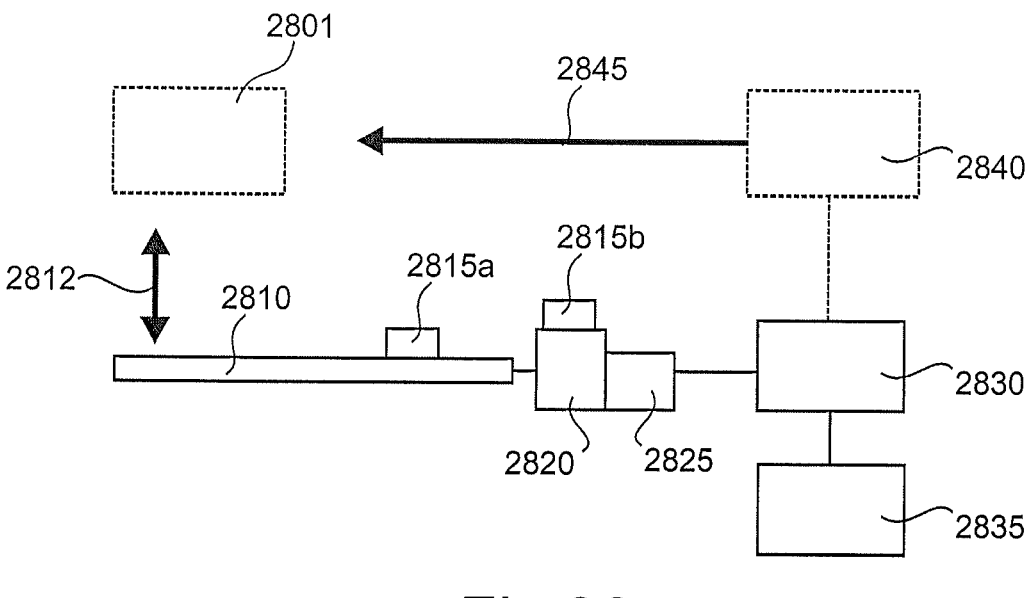
FIG. 28 shows aspects of a system for performing a surgical procedure in accordance with the present disclosure.

FIG. 28 shows aspects of a system for performing a surgical procedure in accordance with the present disclosure. The system is shown interfacing with a surgical site 2801 within a body, a subject, a patient, etc. The system includes a surgical tool 2810 in accordance with the present disclosure. During use, the surgical tool 2810 is configured to interact 2812 with the surgical site 2801 in accordance with the present disclosure. In aspects, the surgical tool 2810 may be coupled to a connector 2820, the connector providing a mechanical, electrical, and/or optical interface between the surgical tool 2810 and one or more other modules of the system. In aspects, the surgical tool 2810 may include an embedded local microcircuit 2815a (a microcircuit, a switch network, a signal conditioning circuit, etc.) in accordance with the present disclosure. In aspects, the connector 2820 may include a local microcircuit 2815b in accordance with the present disclosure. In aspects, the connector 2820 may be coupled to an operator input device 2825 (i.e., a foot pedal, an advancing slider, a torqueing mechanism, a recording button, an ablation button, etc.). In aspects, the connector 2820 may be coupled to a control unit 2830 configured to accept one or more signals from the surgical tool 2810, communicate one or more control signals thereto, send one or more pulsatile and/or radio frequency signals to the microcontroller, record one or more electrophysiological signals from the microsurgical tool, or the like.

In aspects, the control unit 2830 may be connected to a display 2835 configured to present one or more aspects of the recorded signals obtained at least in part with the surgical tool 2810 to an operator, to present a map, at least partially dependent on the recorded signals, one or more metrics relating to the monitoring, one or more diagnostic test results, one or more urodynamic test results, etc.

In aspects, the control unit 2830 may be coupled to a surgical subsystem 2840, the surgical subsystem 2840 configured to perform a surgical procedure 2845 to the surgical site 2801. Some non-limiting examples of suitable surgical procedures include an ablation, a cryoablation, an excision, a cut, a burn, a radio frequency ablation, radiosurgery, an ultrasonic ablation, an abrasion, a biopsy, and delivery of a substance (i.e., a neuromodulating substance in accordance with the present disclosure). The control unit 2830 may be configured to influence, direct, control, and/or provide feedback for one or more aspects of the surgical procedure 2840, based upon one or more of the electrophysiological signals conveyed by the surgical tool 2810.

Some non-limiting methods for performing a surgical procedure in accordance with the present disclosure are discussed herein.

In aspects, a method for addressing a surgical site on an organ in a body (e.g., a bowel wall, a stomach, a kidney, a gland, an artery, a vein, a renal artery, a kidney, a spleen, a pancreas, a prostate, a bladder, etc.) is considered. The method includes, monitoring one or more local physiological signals (e.g., an evoked potential, a neurological activity, MSNA, EMG, MMG, a local field potential, sympathetic tonal change, etc.) in accordance with the present disclosure at one or more measurement locations along a wall of the organ or an entry port connected thereto to determine one or more reference signals; performing at least a portion of a surgical procedure (e.g., an ablation, an excision, a cryoablation, a cut, a burn, an RF ablation, an abrasion, a radiosurgical procedure, a biopsy, delivery of a substance, etc.) in accordance with the present disclosure at or near to one or more surgical locations (e.g., proximal, distal, remotely therefrom, and/or collocated with one or more of the measurement locations); monitoring one or more local physiological signals at one or more of the measurement locations to determine one or more updated signals; and comparing one or more reference signals with one or more updated signals to determine an extent of completion for the surgical procedure.

In aspects, the extent of completion may include a change, reduction and/or substantial elimination of at least a portion of one or more of the local physiological or electrophysiological signals (e.g., reduction in amplitude of a frequency band, reduction in responsiveness, a change in a lag between measurement locations, a change in cross-talk between measurement locations, substantial elimination of the signal, etc.).

In aspects, the extent of completion may include measuring a change in coherence between two or more signals obtained from sites affected by the surgical procedure (i.e., from a first site distal to where the surgical procedure was performed, and from a second site proximal to where the surgical procedure was performed in relation to neural traffic measured at the sites).

In aspects, the procedure may be to perform a temporary neurological block. In this aspect, the method may be used to separate afferent and efferent traffic from either side of the temporary block, decrease traffic from affected sensory receptors (i.e., when causing a neurological block to one or more sensory receptors), etc. for further analysis, diagnosis of disease, evaluation of neurological activity or functionality, or the like. In aspects, a temporary block may be followed by a more permanent block if the analysis demonstrates that such a substantially permanent block would be warranted.

In aspects, the step of monitoring to determine an updated signal may be performed before, during, and/or after the step of performing at least a portion of the surgical procedure. In aspects, monitoring, stimulation, and ablation may be performed in succession and/or in parallel.

In aspects, the method may include sweeping one or more electrodes over the organ wall while monitoring, stimulating, and/or ablating the surface thereof. In aspects, simultaneous monitoring and sweeping may be used to generate a map of neurological activity along the organ wall. In aspects, the method may include penetrating or embedding one or more electrodes into the organ wall, so as to isolate the electrodes from the lumen thereof.

The step of performing at least a portion of the surgical procedure may be repeated. Thus aspects of the method may be incrementally applied, so as to head towards completion in a stepwise process without excessive application of the surgical procedure.

The method may include waiting after performing at least a portion of the surgical procedure. Monitoring may be performed during the waiting procedure, perhaps so as to determine a recovery period for the local physiological signal (i.e., a time period over which the local physiological signal recovers). Such a recovery period may be an indication of the extent of completion.

In aspects, the method may include stimulating one or more stimulation locations (proximal, distal, remotely therefrom, and/or collocated with one or more of the measurement locations and/or the surgical locations). The step of stimulating may be coordinated with the step of performing at least a portion of the surgical procedure, and/or with the step of monitoring to determine a reference and/or updated signal. The stimulation may be provided in any form in accordance with the present disclosure. In aspects, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiological activity.

In aspects, the method may include monitoring one or more remote physiological parameters in accordance with the present disclosure at a remote location (e.g., in the vicinity of an alternative organ, site associated with a related biological process, an organ, a ganglion, a nerve, etc.) substantially removed from the immediate vicinity of the surgical site to determine an updated remote physiological signal and/or reference remote physiological signal.

Some non-limiting examples of remote physiological parameters that may be monitored include water concentration, tone, blood oxygen saturation of local tissues, evoked potential, stimulation/sensing of nervous activity, local field potential, electromyography, temperature, blood pressure, vasodilation, vessel wall stiffness, muscle sympathetic nerve activity (MSNA), central sympathetic drive (e.g., bursts per minute, bursts per heartbeat, etc.), tissue tone, blood flow (e.g., through an artery, through a renal artery), a blood flow differential signal (e.g., a significantly abnormal and or sudden change in blood flow within a structure of the body, a vessel, an organ, etc.), blood perfusion (e.g., to an organ, an eye, etc.), a blood analyte level (e.g., a hormone concentration, norepinephrine, catecholamine, renine, angiotensin II, an ion concentration, a water level, an oxygen level, etc.), nerve traffic (e.g., post ganglionic nerve traffic in the peroneal nerve, celiac ganglion, superior mesenteric ganglion, aorticorenal ganglion, renal ganglion, and/or related nervous system structures), combinations thereof, and the like.

The updated remote physiological signal and/or reference remote physiological signal may be combined and/or compared with one or more reference signals, and/or one or more updated signals in order to determine the extent of completion of a surgical procedure, as part of a decision making process, and/or as part of a surgical control system (i.e., so as to determine whether to continue with, stop, or alter the surgical procedure).

In aspects, the method may include selecting a surgical location. The step of selection may depend upon one or more monitoring steps, proximity to an alternative surgical location (i.e., perhaps a previously treated surgical location, a prospected surgical location, etc.).

In aspects, the method may include sweeping the lumen and/or wall of a vessel while monitoring in order to localize one or more anatomical sites of interest, one or more regions of abnormal activity, etc.

In aspects, the steps of monitoring, comparing, analyzing, diagnosing, and/or treating may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements.

In aspects, the step of monitoring may be used to extract one or more electrophysiological parameters during a first period and monitoring an applied field (i.e., as caused by a stimulation and/or ablation event) during a second period.

In aspects, the method may include generating a topographical map from the one or more measurements (e.g., from one or more of the signals). The method may include determining a topographical map of physiological functionality in the vicinity of the surgical site derived from one or more of the physiological signals. The method may include updating the topographical map after the step of performing at least a portion of the surgical procedure. The method may include generating the map during a sweeping process (i.e., a longitudinal sweep, a circumferential sweep, a helical sweep, etc.).

In aspects, the method may include placement of a plurality of surgical tools, one or more surgical tools (i.e., a procedural tool) placed so as to access one or more of the surgical locations, and one or more surgical tools (i.e., a monitoring tool) placed so as to access one or more of the monitoring locations. In one non-limiting example, a procedural tool may be placed upon a first organ (e.g., a bladder wall, a bowel wall, a stomach wall, a kidney, a gland, a renal artery, a left renal artery, etc.) and a monitoring tool may be placed upon a second organ (e.g., an opposing renal artery, a right renal artery, a femoral artery, an iliac artery, a vagina, a uterus, a rectum, in the vicinity of a sacrum, etc.). Thus, the monitoring tool may be used to monitor one or more of the measurement locations on the second organ. The procedural tool may be used to surgically treat one or more surgical locations on the first organ. Additionally, alternatively, or in combination, the procedural tool may monitor one or more monitoring locations on the first organ, perhaps in combination with monitoring performed on the second organ by the monitoring tool.

In aspects, the method may be performed with one or more surgical tools in accordance with the present disclosure.

One or more steps of monitoring may be performed with one or more sensing tips in accordance with the present disclosure.

One or more steps of performing at least a portion of the surgical procedure may be performed with one or more sensing tips in accordance with the present disclosure.

In aspects, a method for RF ablating tissue is provided. During such a method, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored to determine an extent of completion of the procedure. Such an approach may be advantageous as the tonal measurement techniques may not be significantly affected by the local RF currents associated with the RF ablation procedure.

In aspects, an interventionalist/proceduralist may insert a catheter in accordance with the present disclosure into the urethra so as to cannulate the bladder. In aspects, a guiding catheter may be used for this purpose, and to form a stable reference through which to deliver one or more surgical tools. In aspects, a surgical tool in accordance with the present disclosure may be placed through the guiding catheter.

In aspects, an interventionalist/proceduralist may insert a surgical tool in accordance with the present disclosure via a percutaneous approach, perhaps under guidance with a visualization aid (i.e., ultrasound guidance, radiosurgical guidance, etc.) so as to approach the intended organ from an alternative direction. In aspects, a combination of urethral and percutaneous approaches may be coordinated (i.e., in the case of multi-tool procedures).

In aspects, the electrodes may be configured and dimensioned so as to penetrate into the organ wall upon biased there against. The electrodes may be forced to cause penetration of one or more of the electrodes into the intima, mucosa, submucosa, transitional epithelium, muscular layers, detrusor muscle, longitudinal muscle layer, circular muscle layer, adventitia, peritoneum, of the organ wall (i.e., bladder, uterus, etc.) or adventitia in the vicinity thereof to be measured. In aspects, one or more electrodes may be configured for microscopic or macroscopic spatial recording. In aspects, a plurality of microscopically configured electrodes may be used to generate one or more macroscopic spatial recordings from a collection of microscopic spatial recordings. Following a suitable period of recording, the device may be withdrawn into the guiding catheter and removed from the body.

In aspects, a substrate, balloon wall, microfinger, filament, etc. in accordance with the present disclosure including/supporting a penetrating electrode, may include one or more features configured so as to limit the penetration depth thereof into the wall during such a procedure. In aspects, such depth limiting features may include a partition, a flange, a bump, a collar, a step in diameter (i.e., in the case of a microfinger, or filament, etc.), combinations thereof, or the like. In aspects, a balloon wall or substrate mounted penetrating electrode may be configured so as to limit the depth of penetration into an adjacent tissue surface via the embossed height of the electrode beyond the balloon wall or substrate itself (i.e., the needle height, embossed height, etc.).

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A surgical tool for neuromodulating bladder function, comprising:
    an elongate delivery member configured and dimensioned to be inserted into a bladder through a urethra;
    a therapy delivery element coupled with the elongate delivery member, configured to interface with a tissue in a target region of a bladder wall to provide therapy to the target region;
    a plurality of sensing tips electrically and mechanically coupled with the elongate delivery member, configured to interface with one or more tissue surfaces of at least one of the bladder wall and the urethra, wherein one or more of the sensing tips are configured to convey one or more electrophysiological signals associated with the tissue surfaces at least one of before, during, and after the therapy; and
    a controller coupled to the elongate delivery member, the controller configured to independently adjust a bias force of a first one of the plurality of sensing tips and at least a second one of the plurality of sensing tips to maintain a first position of the first sensing tip and a second position of the second sensing tip while the therapy is provided to the target region.

2. The surgical tool in accordance with claim 1, wherein the electrophysiological signals are related to one or more of water concentration, tissue tone, evoked potential, remotely stimulated nervous activity, a pressure stimulated nervous response, an electrically stimulated movement, sympathetic nervous activity, an electromyographic signal, [EMG], a mechanomyographic signal [MMG], a local field potential, an electroacoustic event, vasodilation, bladder wall stiffness, muscle sympathetic nerve activity [MSNA], central sympathetic drive, nerve traffic, or combinations thereof.

3. The surgical tool in accordance with claim 1, wherein one or more of the plurality of sensing tips comprise the therapy delivery element.

4. The surgical tool in accordance with claim 3, wherein at least one of the tissue surfaces is substantially coincident with the target region.

5. The surgical tool in accordance with claim 1, wherein at least one of the plurality of sensing tips comprises one or more electrodes configured to interface with the one or more tissue surfaces.

6. The surgical tool in accordance with claim 5, wherein one or more of the electrodes comprises at least one of an embossed, a plated, and a filament loaded structure thereupon configured to protrude into the one or more tissue surfaces when biased there against.

7. The surgical tool in accordance with claim 1, wherein one or more of the plurality of sensing tips are electrically coupled with a microcircuit, the microcircuit configured to condition the one or more electrophysiological signals.

8. The surgical tool in accordance with claim 7, wherein the microcircuit is embedded into the surgical tool and at least a portion of the electrical coupling is provided via the elongate delivery member.

9. The surgical tool in accordance with claim 1, wherein one or more of the plurality of sensing tips comprise at least one of one or more needle electrodes and one or more whiskers arranged so as to extend from the one or more of the plurality of sensing tips into the one or more tissue surfaces.

10. The surgical tool in accordance with claim 1, wherein one or more of the plurality of sensing tips comprise a mechanomyographic (MMG) sensing element configured to generate a mechanomyographic signal (MMG) from the one or more tissue surfaces.

11. The surgical tool in accordance with claim 1, wherein one or more of the plurality of sensing tips comprise a compliance sensor, configured to generate a tissue tone signal.

12. The surgical tool in accordance with claim 1, wherein one or more of the plurality of sensing tips comprise a microelectrode configured to interface with the associated tissue surface, the microelectrode having an area of less than 5000 micrometers squared.

13. The surgical tool in accordance with claim 1, wherein at least one of one or more of the plurality of sensing tips and the therapy delivery element are configured to at least one of stimulate and ablate the one or more tissue surfaces and the target region, respectively.

14. The surgical tool in accordance with claim 1, wherein at least one of one or more of the plurality of sensing tips and the therapy delivery element are configured to at least one of electrically stimulate and electrically ablate the one or more tissue surfaces and the target region, respectively.

15. The surgical tool in accordance with claim 1, wherein at least one of one or more of the plurality of sensing tips and the therapy delivery element are configured to at least one of mechanically stimulate and ultrasonically ablate the one or more tissue surfaces and the target region, respectively.

16. The surgical tool in accordance with claim 13, wherein one or more of the plurality of sensing tips are configured so as to monitor an effect of the stimulation the ablation on the one or more tissue surfaces and the target region.

17. The surgical tool in accordance with claim 1, wherein the therapy delivery element configured to deliver a therapeutic substance to the target region.

18. The surgical tool in accordance with claim 17, wherein one or more of the plurality of sensing tips are configured to monitor an effect of the therapeutic substance on the target region.

19. The surgical tool in accordance with claim 18, wherein the therapeutic substance is selected from a chemical, a drug substance, a neuromodulating substance, a neuroblocking substance, an acid, a base, a denervating agent, or a combination thereof.

20. The surgical tool in accordance with claim 19, wherein the therapeutic substance is a selected from a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, capsaicin, an anesthetic, lidocaine, tetanus toxin, quaternary ammonium salts, a pachycurare, a leptocurare, acetylcholine, aminosteroids, or a combination thereof.

\* \* \* \* \*